US 12,246,052 B2
(12) United States Patent
Powell et al.

(10) Patent No.: US 12,246,052 B2
(45) Date of Patent: *Mar. 11, 2025

(54) ANTIMICROBIAL HEVAMINE A-RELATED COMPOSITIONS AND METHODS

(71) Applicant: MOREHOUSE SCHOOL OF MEDICINE, Atlanta, GA (US)

(72) Inventors: Michael Powell, Douglasville, GA (US); Erick Vidjin' Agnih Gbodossou, Dakar-Etoile (SN)

(*) Notice: Subject to any disclaimer, the term of this patent is extended or adjusted under 35 U.S.C. 154(b) by 0 days.

This patent is subject to a terminal disclaimer.

(21) Appl. No.: 18/432,324

(22) Filed: Feb. 5, 2024

(65) Prior Publication Data
US 2024/0325481 A1 Oct. 3, 2024

Related U.S. Application Data

(63) Continuation of application No. 17/805,753, filed on Jun. 7, 2022, now Pat. No. 11,925,670.

(60) Provisional application No. 63/208,698, filed on Jun. 9, 2021.

(51) Int. Cl.
| A61K 36/42 | (2006.01) |
| A01N 63/50 | (2020.01) |
| A01P 1/00 | (2006.01) |
| A61K 31/352 | (2006.01) |
| A61K 33/30 | (2006.01) |
| A61K 38/47 | (2006.01) |
| A61P 31/18 | (2006.01) |
| C12N 15/10 | (2006.01) |
| C12N 15/82 | (2006.01) |
| C12P 19/34 | (2006.01) |

(52) U.S. Cl.
CPC ............. *A61K 36/42* (2013.01); *A01N 63/50* (2020.01); *A01P 1/00* (2021.08); *A61K 31/352* (2013.01); *A61K 33/30* (2013.01); *A61K 38/47* (2013.01); *A61P 31/18* (2018.01); *C12N 15/1096* (2013.01); *C12N 15/8283* (2013.01); *C12P 19/34* (2013.01); *C07K 2319/01* (2013.01)

(58) Field of Classification Search
CPC ......... A01N 63/50; A01P 1/00; A61K 31/352; A61K 33/30; A61K 38/47; A61P 31/18; C12N 15/8283
See application file for complete search history.

(56) References Cited

U.S. PATENT DOCUMENTS

| 4,535,060 | A | 8/1985 | Comai |
| 5,405,765 | A | 4/1995 | Vasil et al. |
| 5,472,869 | A | 12/1995 | Krzyek et al. |
| 5,508,468 | A | 4/1996 | Lundquist et al. |
| 5,538,877 | A | 7/1996 | Lundquist et al. |
| 5,538,880 | A | 7/1996 | Lundquist et al. |
| 5,545,818 | A | 8/1996 | McBride et al. |
| 5,550,318 | A | 8/1996 | Adams et al. |
| 5,563,055 | A | 10/1996 | Townsend et al. |
| 5,641,664 | A | 6/1997 | D'Halluin et al. |
| 5,668,085 | A | 9/1997 | Forbes et al. |
| 5,683,958 | A | 11/1997 | Berger et al. |
| 5,703,015 | A | 12/1997 | Berger et al. |
| 5,736,369 | A | 4/1998 | Bowen et al. |
| 6,063,733 | A | 5/2000 | Berger et al. |
| 6,121,199 | A | 9/2000 | Berger et al. |
| 6,121,200 | A | 9/2000 | Berger et al. |
| 6,184,182 | B1 | 2/2001 | Gillespie et al. |
| 6,245,713 | B1 | 6/2001 | Brinker et al. |
| 6,365,551 | B1 | 4/2002 | Wright et al. |
| RE37,866 | E | 10/2002 | Wright et al. |
| 6,566,587 | B1 | 5/2003 | Lebrun et al. |
| 8,937,214 | B2 | 1/2015 | Gilbertson et al. |
| 10,329,580 | B2 | 6/2019 | Schultheiss et al. |
| 2003/0104943 | A1 | 6/2003 | Lennon et al. |
| 2018/0290804 | A1 | 10/2018 | Aldaous et al. |
| 2022/0135997 | A1 | 5/2022 | Schultink et al. |

FOREIGN PATENT DOCUMENTS

| EP | 4019032 | 8/2021 |
| WO | 2010112968 | 10/2010 |
| WO | 2020132062 | 6/2020 |
| WO | 2022039822 | 2/2022 |

OTHER PUBLICATIONS

Zhou et al, "Single Asparagine- Linked Glycosylation Site of the Severe Acute Respiratory Syndrome Coronavirus Spike Glycoprotein Facilitates Inhibition by Mannose-Binding Lectin through Multiple Mechanisms", Journal of Virology, 2010 pp. 8753-8764.

Akkouh, et al. "Lectins with Anti HIV Activity: Review", Molecules, 2015, vol. 20, pp. 648-668.

(Continued)

*Primary Examiner* — Kade Ariani

(74) *Attorney, Agent, or Firm* — Ping Wang; Kalos Athena Wang PLLC

(57) ABSTRACT

In one aspect, nutraceutical compositions, methods of preparation and methods of use comprise a nutraceutical composition comprising an antimicrobial hevamine A-related protein from *Momordica balsamina* alone or in combination with one or more nutraceutical ingredients. In another aspect, a method of preventing or treating a microbial infection in a plant comprises applying an effective amount of a composition containing the hevamine A-related protein to a whole plant, plant part, or media in which the plant is growing. In a further aspect, the present application provides a transgenic plant stably transformed with a polynucleotide encoding the hevamine A-related protein.

3 Claims, 23 Drawing Sheets

Specification includes a Sequence Listing.

(56) References Cited

OTHER PUBLICATIONS

Mani, et al. "Natural Product-derived Phytochemicals as Potential Agents Against Coronaviruses: A Review" Virus Research, 2020 pp. 1-16.

Raman et al. "Glycan-Protein Interactions in Viral Pathogenesis", Current Opinion in Structural Biology, 2016, vol. 40, pp. 153-162.

Di Veroli, et al. "An Automated fitting procedure and softball for dose response curves with multiphasic features", Scientific Reports, 2015, pp. 1-11.

He, et al. "Potent HIV Fusion Inhibitors against Enfuvirtide- resistant HIV-1 Strains" The National Academy of Science of the USA, 2008 vol. 105 pp. 16332-16337.

Kelly, et al. "The Phyre2 Web Portal for Protein Modeling, Prediction and Analysis" Natural Protocols, 2015 vol. 10 pp. 845-858.

Khan et al. "Restoration of Wild Type Infectivity to Human Immunodeficiency Virus Type 1 Strains Lacking nef by intravirion Reverse Transcription", Journal of Virology, 2001, vol. 75, pp. 12081-12087.

Kimpton et al. "Detection of Replication Competent n pseudotyped human immunodeficiency virus with a sensitive cell line on the basis of activation of an integrated beta galactosidase gene" Journal of Virology 1992, vol. 66 pp. 2232-2239.

Romero-Romero et al. "The Stability Landscape of de novo TIM Barrels Explored by a Modular Design Approach", Journal of Molecular Biology, 2021, vol. 433, pp. 1-20.

Punja et al. "Plant Chitinases and Their Roles in Resistance to Fungal Diseases", Journal of Nematolgy, 1993, vol. 25, pp. 526-540.

Raymond et al. "HIV Type-1 Nef is Released from Infected Celled in CD45+ Microvesicles and is Present in the Plasma of HIV Infected Individuals" AIDS Research and Human Retroviruses 2011, vol. 27, pp. 167-178.

Sahai et al. , "Chitnases of fungi and plants: their in morphogenesis and host parasite involvement interaction" FEMS Microbiology Reviews 1993, vol. 11, pp. 317-338.

Scanlan et al. "The Broadly Neutralizing Anti Human Immunodeficiency Virus Type1 Antibody 2G12 Recognizes a Cluster of a1 -2 Mannose Residues on the outer Face of gp120" Journal of Virology, 2002, vol. 76, pp. 7306-7321.

Simek et al. "Human Immunodeficiency Virus Type 1 Elite Neutralizers: Individuals with Broad and Potent Neutralizing Activity Identified by using a High Throughput Neutralization Assay together with an Analytical Selection Algorithm" Journal of Virology, 2009, vol. 83, pp. 7337-7348.

Wierenga et al. "The TIM-barrel Fold: a versatile framework for efficient enzymes" FEBS Letters, 2001 vol. 492, pp. 193-198.

International Search Report and Written Opinion, Issued in International Patent Application PCT/US2022/032463, mail date: Sep. 28, 2022.

U.S. Appl. No. 18/432,324, filed Feb. 5, 2024.

U.S. Appl. No. 17/805,753, filed Jun. 7, 2022.

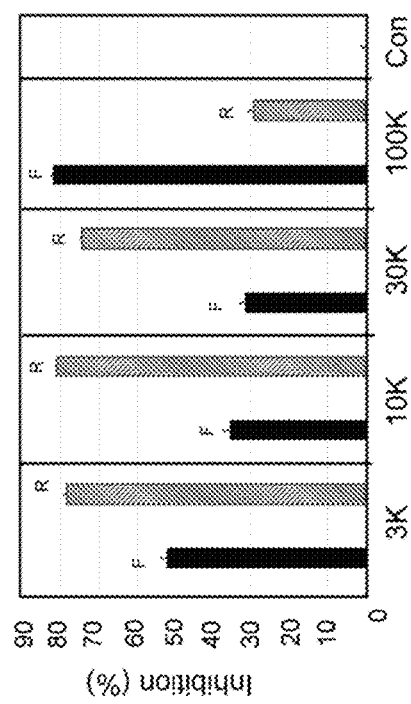
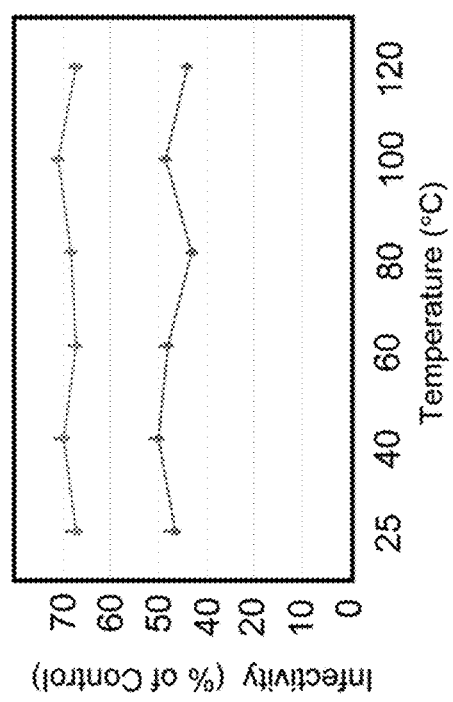
FIG. 4A
FIG. 4B

M. balsamina MoMo30 = SEQ ID NO: 1
M. charantia Hev A = SEQ ID NO: 5
M. charantia MAP30 = SEQ ID NO: 17

GGIATYWGQDTREGRLTAACATGKFQIINIGFLSTFGNGRPPQVNLTRHCSPISNGCRNVSVGVLNCRN
DGVKVMLSIGGPHGSYSLSSAAEAIDLADYIWNNFLGGRSTSLRPFGDVPLDGVDFRIERGQFSHYYTM
VARRLHDYGRQCSRKVYLTAAPGCRFPDKYLTELLHTGLFDYVWRFFDDROCQYNSVNPSGFWWSW
MRWINSIPARKFVGIPASEEAGDGYVAPEVLIKEVLPFTKKFTNYGGVMLFDLSNDVQTNYSSIISNRV
SEQ ID NO: 4

| | | | | |
|---|---|---|---|---|
| Momordica balsamina | 73 | VMI_I__ ... | _GIDF_I_ | 127 | SEQ ID NO: 7 |
| Momordica charantia | 73 | VLI_I__ ... | _GVDF_I_ | 127 | SEQ ID NO: 8 |
| Hevea | 73 | VMI_I__ ... | _GIDF_I_ | 127 | SEQ ID NO: 9 |
| Cucumis | 98 | VLI_I__ ... | _GVDF_I_ | 152 | SEQ ID NO: 10 |
| Nicotana | 89 | TFI_I__ ... | _GLDL_W_ | 138 | SEQ ID NO: 11 |
| Saccharomyces | 102 | VLI_I__ ... | _GFDF_I_ | 157 | SEQ ID NO: 12 |
| Alteromonas | 265 | ILE_I__ ... | _GVDI_W_ | 313 | SEQ ID NO: 13 |
| Bacillus A1 | 158 | TII_V__ ... | _GVDL_W_ | 204 | SEQ ID NO: 14 |
| Manduca sextaipsum | 257 | FMV_V__ ... | _GLDL_W_ | 146 | SEQ ID NO: 15 |

FIG. 8

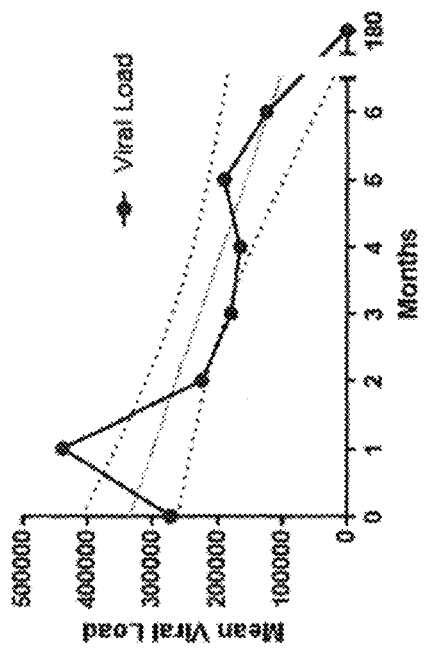
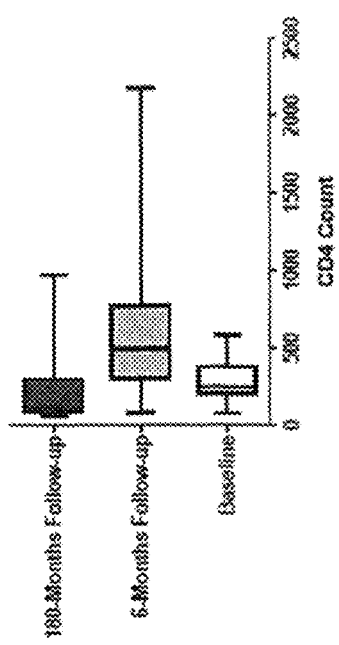
FIG. 21A
FIG. 21B

SEQUENCE LISTING

```
Sequence total quantity: 17
SEQ ID NO: 1            moltype = DNA  length = 921
FEATURE                 Location/Qualifiers
misc_feature            1..921
                        note = MISC_FEATURE - M. balsamina MOMO30 nucleotide coding
                         region sequence for preprotein
source                  1..921
                        mol_type = genomic DNA
                        organism = Momordica balsamina
SEQUENCE: 1
atggaatctc aattttgttc ttcatttcca tgttttattc tcctcgtaat tttccctttt   60
atgggctatt attccgaagc aataattacc ggcggcggaa ttgcgactta ttggggccag  120
```

-continued

```
gacacgagag agggccgact gaccgccgcc tgcgccaccg gaaaatttca gatcatcaac  180
atagggttcc tctctacatt cggcaacggc cggccgccgc aagtgaacct aacgcgccac  240
tgcagtccca tctccaacgg ttgccggaat gtgagcgtcg gcgtcctcaa ctgccgaaac  300
gacggcgtta aagtcatgct ctccatcggt ggccctcatg gaagctactc cctctcctcc  360
gccgccgaag ccattgacct tgctgactac atctggaaca attttctcgg tggccgctcc  420
acgtcactac gaccattcgg tgatgtgcca ttggacggcg tagatttcag gattgaacga  480
ggtcagtttt cccactatta cactatggtt gctcggcggc tacacgacta tggtcgacaa  540
tgtagtcgta aagtgtacct aacggcggct ccaggttgcc gttttccaga caagtaccta  600
accgaattgc ttcacactgg acttttcgac tatgtttggg ttagattttt tgacgatcga  660
caatgccaat ataattctgt taacccgtct ggcttttggt ggtcgtggat gcggtggata  720
aattcaattc cggcgaggaa attttacgtg ggaattcctg catctgaaga agccggagat  780
gggtacgtgg caccagaggt gttgataaag gaagtattgc cctttactaa gaagtttacc  840
aattacggtg gcgttatgct tttcgacttg tcgaatgatg ttcaaactaa ctacagttct  900
ataattagca atagggtttg a                                            921

SEQ ID NO: 2            moltype = DNA  length = 829
FEATURE                 Location/Qualifiers
misc_feature            1..829
                        note = MISC_FEATURE - M. balsamina MOMO30 nucleotide coding
                         sequence for mature/secreted protein
source                  1..829
                        mol_type = genomic DNA
                        organism = Momordica balsamina
SEQUENCE: 2
cggcggaatt gcgacttatt ggggccagga cacgagagag ggccgactga ccgccgcctg  60
cgccaccgga aaatttcaga tcatcaacat agggttcctc tctacattcg gcaacggccg  120
gccgccgcaa gtgaacctaa cgcgccactg cagtcccatc tccaacggtt gccggaatgt  180
gagcgtcggc gtcctcaact gccgaaacga cggcgttaaa gtcatgctct ccatcggtgg  240
ccctcatgga agctactccc tctcctccgc cgccgaagcc attgaccttg ctgactacat  300
ctggaacaat tttctcggtg gccgctccac gtcactacga ccattcggtg atgtgccatt  360
ggacggcgta gatttcagga ttgaacgagg tcagttttcc cactattaca ctatggttgc  420
tcggcggcta cacgactatg gtcgacaatg tagtcgtaaa gtgtacctaa cggcggctcc  480
aggttgccgt tttccagaca agtacctaac cgaattgctt cacactggac ttttcgacta  540
tgtttgggtt agattttttg acgatcgaca atgccaatat aattctgtta acccgtctgg  600
cttttggtgg tcgtggatgc ggtggataaa ttcaattccg gcgaggaaat tttacgtggg  660
aattcctgca tctgaagaag ccggagatgg gtacgtggca ccagaggtgt tgataaagga  720
agtattgccc tttactaaga agtttaccaa ttacggtggc gttatgcttt tcgacttgtc  780
gaatgatgtt caaactaact acagttctat aattagcaat agggtttga             829

SEQ ID NO: 3            moltype = AA  length = 306
FEATURE                 Location/Qualifiers
REGION                  1..306
                        note = MISC_FEATURE - M. balsamina MOMO30 amino acid
                         sequence for preprotein
source                  1..306
                        mol_type = protein
                        organism = Momordica balsamina
SEQUENCE: 3
MESQFCSSFP CFILLVIFPF MGYYSEAIIT GGGIATYWGQ DTREGRLTAA CATGKFQIIN  60
IGFLSTFGNG RPPQVNLTRH CSPISNGCRN VSVGVLNCRN DGVKVMLSIG GPHGSYSLSS  120
AAEAIDLADY IWNNFLGGRS TSLRPFGDVP LDGVDFRIER GQFSHYYTMV ARRLHDYGRQ  180
CSRKVYLTAA PGCRFPDKYL TELLHTGLFD YVWVRFFDDR QCQYNSVNPS GFWWSWMRWI  240
NSIPARKFYV GIPASEEAGD GYVAPEVLIK EVLPFTKKFT NYGGVMLFDL SNDVQTNYSS  300
IISNRV                                                             306

SEQ ID NO: 4            moltype = AA  length = 275
FEATURE                 Location/Qualifiers
REGION                  1..275
                        note = MISC_FEATURE - M. balsamina MOMO30 amino acid
                         sequence for mature/secreted protein
source                  1..275
                        mol_type = protein
                        organism = Momordica balsamina
SEQUENCE: 4
GGIATYWGQD TREGRLTAAC ATGKFQIINI GFLSTFGNGR PPQVNLTRHC SPISNGCRNV  60
SVGVLNCRND GVKVMLSIGG PHGSYSLSSA AEAIDLADYI WNNFLGGRST SLRPFGDVPL  120
DGVDFRIERG QFSHYYTMVA RRLHDYGRQC SRKVYLTAAP GCRFPDKYLT ELLHTGLFDY  180
VWVRFFDDRQ CQYNSVNPSG FWWSWMRWIN SIPARKFYVG IPASEEAGDG YVAPEVLIKE  240
VLPFTKKFTN YGGVMLFDLS NDVQTNYSSI ISNRV                             275

SEQ ID NO: 5            moltype = DNA  length = 921
FEATURE                 Location/Qualifiers
misc_feature            1..921
                        note = MISC_FEATURE - M. charantia MOMO30 nucleotide coding
                         region sequence for preprotein
source                  1..921
                        mol_type = genomic DNA
                        organism = Momordica charantia
SEQUENCE: 5
```

-continued

```
atggaatctc aattttgttc ttcatttcca cgtttttctt ccctcataat tctcgcttct    60
atattgggtt gttattcgga agcaattacc ggcggcggaa ttgccactta ctggggccag   120
aacacgagag agggccggct gaccgccgcc tgcgccaccg gaaaatttca gatcatcaac   180
ataggggttcc tctctacatt cggcaacggc cggccgccgc aagtgaacct aacgcgccac   240
tgcagtcccg tctccaacgg ctgccggaat gtgagcgttg gcgtcctcaa ctgccgaaac   300
gatggcgtta aagtcatgct ctccattggt ggccctcacg gaagctactt cctctcctcc   360
gccgccaag ccgttgacct tgctgactac atctggaaca acttcctcgg cggccactcc   420
acgtcactac gaccgtttgg tgatgtacca ttggacggtg tagatttcag gattgagcga   480
gtcgagttct cccactacta cgccatggtt gctcggcggc tacacgacta tggccggcaa   540
agtaaccgta aagtgtactt aacggccgcg ctgcc gttttcccga caaatacctca   600
actgaatcgc ttcacactgg acttttcgac tatgttgggg ttagattttt tgacgaccgg   660
caatgccgtt atgattccgt taacccgtcg ggcttttggt ggtcgtggat gcggtggaca   720
cattcaattc cggcgaggaa attttacttg ggaattccgg catccgaaga agccggagat   780
gggtacgtgg caccggaggt gctgataaag gaagtgctgc cgtttgttaa gaggttcaca   840
agttatggcg gcgttatgct tttcgacttg tcgaatgatg ttcaaactaa ctacagttct   900
ataattagca ataggttttg a                                             921

SEQ ID NO: 6                moltype = AA   length = 306
FEATURE                     Location/Qualifiers
REGION                      1..306
                            note = MISC_FEATURE - M. charantia MOMO30 amino acid
                              sequence for preprotein
source                      1..306
                            mol_type = protein
                            organism = Momordica charantia
SEQUENCE: 6
MESQFCSSFP RFLLLIILAS ILGCYSEAIT GGGIATYWGQ NTREGRLTAA CATGKFQIIN    60
IGFLSTFGNG RPPQVNLTRH CSPVSNGCRN VSVGVLNCRN DGVKVMLSIG GPHGSYFLSS   120
AAEAVDLADY IWNNFLGGHS TSLRPFGDVP LDGVDFRIER VEFSHYYAMV ARRLHDYGRQ   180
SNRKVYLTAA PGCRFPDKYL TESLHTGLFD YVWVRFFDDR QCRYDSVNPS GFWWSWMRWT   240
HSIPARKFYL GIPASEEAGD GYVAPEVLIK EVLPFVKRFT SYGGVMLFDL SNDVQTNYSS   300
IISNRV                                                              306

SEQ ID NO: 7                moltype = AA   length = 17
FEATURE                     Location/Qualifiers
REGION                      1..17
                            note = Synthetic: Hevamine A-like
source                      1..17
                            mol_type = protein
                            organism = synthetic construct
SEQUENCE: 7
KVMLSLGGLD GIDFDIE                                                   17

SEQ ID NO: 8                moltype = AA   length = 17
FEATURE                     Location/Qualifiers
REGION                      1..17
                            note = Synthetic: Hevamine A-like
source                      1..17
                            mol_type = protein
                            organism = synthetic construct
SEQUENCE: 8
KVLLSIGGLD GVDFDIE                                                   17

SEQ ID NO: 9                moltype = AA   length = 17
FEATURE                     Location/Qualifiers
REGION                      1..17
                            note = Synthetic: Hevamine A-like
source                      1..17
                            mol_type = protein
                            organism = synthetic construct
SEQUENCE: 9
KVMLSLGGLD GIDFDIE                                                   17

SEQ ID NO: 10               moltype = AA   length = 17
FEATURE                     Location/Qualifiers
REGION                      1..17
                            note = Synthetic: Hevamine A-like
source                      1..17
                            mol_type = protein
                            organism = synthetic construct
SEQUENCE: 10
KVLLSIGGLD GVDFDIE                                                   17

SEQ ID NO: 11               moltype = AA   length = 17
FEATURE                     Location/Qualifiers
REGION                      1..17
                            note = Synthetic: Hevamine A-like
source                      1..17
                            mol_type = protein
```

```
                         organism = synthetic construct
SEQUENCE: 11
KTFLSIAGFH GLDLDWE                                                       17

SEQ ID NO: 12            moltype = AA   length = 17
FEATURE                  Location/Qualifiers
REGION                   1..17
                         note = Synthetic: Hevamine A-like
source                   1..17
                         mol_type = protein
                         organism = synthetic construct
SEQUENCE: 12
KVLLSLGGVD GFDFDIE                                                       17

SEQ ID NO: 13            moltype = AA   length = 17
FEATURE                  Location/Qualifiers
REGION                   1..17
                         note = Synthetic: Hevamine A-like
source                   1..17
                         mol_type = protein
                         organism = synthetic construct
SEQUENCE: 13
KILPSIGGYD GVDIDWE                                                       17

SEQ ID NO: 14            moltype = AA   length = 17
FEATURE                  Location/Qualifiers
REGION                   1..17
                         note = Synthetic: Hevamine A-like
source                   1..17
                         mol_type = protein
                         organism = synthetic construct
SEQUENCE: 14
KTIISVGGFD GVDLDWE                                                       17

SEQ ID NO: 15            moltype = AA   length = 17
FEATURE                  Location/Qualifiers
REGION                   1..17
                         note = Synthetic: Hevamine A-like
source                   1..17
                         mol_type = protein
                         organism = synthetic construct
SEQUENCE: 15
KFMVAVGGFD GLDLDWE                                                       17

SEQ ID NO: 16            moltype = AA   length = 16
FEATURE                  Location/Qualifiers
REGION                   1..16
                         note = Synthetic: MOMO30 N-terminal amino acid sequence
VARIANT                  12
                         note = Xaa can be any naturally occurring amino acid
source                   1..16
                         mol_type = protein
                         organism = synthetic construct
SEQUENCE: 16
GPIVTYWGQN VXEGEL                                                        16

SEQ ID NO: 17            moltype = DNA   length = 861
FEATURE                  Location/Qualifiers
misc_feature             1..861
                         note = M. charantia MAP30 nucleotide coding region sequence
                          for preprotein
source                   1..861
                         mol_type = genomic DNA
                         organism = Momordica charantia
SEQUENCE: 17
atggtggtat gcttactact ttcttttta attatcgcca tcttcattgg tgttcctact      60
gccaaaggcg atgttaactt cgatttgtcg actgccactg caaaaaccta cacaaaattt    120
atcgaagatt tcagggcgac tcttccattt agccataaag tgtatgatat acctctactg    180
tattccacta tttccgactc cagacgtttc atactcctca atctcacaag ttatgcatat    240
gaaaccatct cggtggccat agatgtgacg aacgtttatg ttgtggccta tcgcacccgc    300
gatgtatcct acttttttaa agaatctcct cctgaagctt ataacatcct attcaaaggt    360
acgcggaaaa ttacactgcc atataccggt aattatgaaa tcttcaaac tgctgcacac    420
aaaataagag agaatattga tcttggactc cctgccttga gtagtgccat taccacattg    480
tttattacca atgcccaatc tgctccttct gcattgcttg tactaatcca gacgactgca    540
gaagctgcaa gatttaagta tatcgagcga cacgttgcta gtatgttgc cactaacttt    600
aagccaaatc tagccatcat aagcttggaa atcaatggt ctgctctctc caaacaaata    660
```

```
tttttggcgc agaatcaagg aggaaaattt agaaatcctg tcgaccttat aaaacctacc    720
ggggaacggt ttcaagtaac caatgttgat tcagatgttg taaaaggtaa tatcaaactc    780
ctgctgaact ccagagctag cactgctgat gaaaacttta tcacaaccat gactctactt    840
ggggaatctg ttgtgaattg a                                              861
```

ANTIMICROBIAL HEVAMINE A-RELATED COMPOSITIONS AND METHODS

This present application is a Continuation application of U.S. application Ser. No. 17/805,753, filed Jun. 7, 2022, which claims priority to U.S. Provisional Patent Application Ser. No. 63/208,698, filed on Jun. 9, 2021. The entirety of the aforementioned applications is incorporated herein by reference.

The application contains a Sequence Listing which has been submitted electronically in .XML format and is hereby incorporated by reference in its entirety. Said .XML copy, created on Feb. 12, 2024, is named "1013-764 CONT.xml" and is 27,387 bytes in size. The sequence listing contained in this .XML file is part of the specification and is hereby incorporated by reference herein in its entirety.

FIELD

The present application generally relates to a hevamine A-related protein and methods of use thereof. More particularly, the present application relates to the use of the hevamine A-related protein in nutraceutical compositions for a subject. The present application also discloses methods for preventing or treating microbial infections in plants, and transgenic plants.

BACKGROUND

The surfaces of host cells and microorganisms are decorated by complex glycans, which play multifaceted roles in the dynamic interplay between the microorganisms and the host. Such lectins are known to facilitate microbial infections by specific multivalent interactions between cell surfaces decorated by complex glycans and their cognate protein lectins (see e.g., Raman, R. et al., Curr. Opin. Struct. Biol., 40:153-162, 2016).

Lectin proteins are sugar-binding proteins that bind specifically and reversibly to carbohydrate groups. They are typically anchored on the surfaces of cells and are found in all groups of living organisms including plants, animals, *fungi*, and bacteria, as well as viruses and mycoplasmas. Depending on their broad sugar-binding specificity, they have been classified as mannose-, galactose-, N-acetylglucosamine-, fucose- and sialic acid-binding lectins, according to the simple sugars that inhibit their carbohydrate-binding properties.

The complex glycans displayed on host cell surfaces typically function as attachment factors, co-receptors or primary receptors that are specifically recognized by microbial surface glycoprotein similarly decorated by a variety of glycans. For example, complex glycans terminated by α2-3 or α2-6-linked sialic acid (N-acetyl neuraminic acid) function as receptors for several different viruses. Linear sulfated glycosaminoglycans such as heparan sulfate act as co-receptors for a variety of viruses, including dengue virus, hepatitis C virus, and foot-and-mouth disease virus. The display of specific glycan motifs on surfaces of different cells and tissues contributes to the host restriction and cell/tissue tropism of microorganisms.

A wide variety of lectins from animals, plants, algae, cyanobacteria, and other sources have been shown to possess antimicrobial activity against a wide variety of bacteria and *fungi*. Such lectins are also found on the surfaces of viruses, including coronaviruses, human immunodeficiency viruses (HIVs), influenza viruses, herpes simplex viruses, Ebola viruses, and others. See e.g., Mani et al., Virus Res., Apr. 30, 2020, pp. 197989; Akkouh et al., Molecules, 20:648-668, 2015). For example, the influenza virus hemagglutinin is one of the most well-studied examples of a viral glycan-binding protein and is known to bind to sialic acid-containing glycans on the host cell surface. Additionally, mannose binding lectin (MBL), a serum protein in humans important in host defenses has been shown to selectively bind to the SARS COV Spike(S) protein in a SARS-COV pseudotyped virus and potently inhibit SARS-COV infection of susceptible cell lines at concentrations below those observed in the serum of healthy individuals (Zhou, Y et al., J. Virol., 84 (17): 8753-8764, 2010). Exemplary lectins with broad spectrum antiviral activity against multiple viruses include Concanavalin A from jack bean, Griffithsin from red algae, and Cyanovirin-N from cyanobacteria.

Similarly, lectins mediate adhesion of bacteria to host cells or tissues, which is a prerequisite for infection and/or symbiosis to occur. Consequently, lectin-deficient microbial mutants are often unable to initiate infection. Glycans recognized by microbial surface lectins have been shown to block the adhesion of bacteria to animal cells in vitro and in vivo, and thus may protect animals against infection by bacteria.

In view of the wide range of microorganisms containing various glycans on their cell surface, there is a need to identify natural broad spectrum antimicrobial agents having properties characteristic of lectins for binding and neutralizing microorganisms in microbial infections in both humans and plants. The present application addresses this need and provides a plant-derived broad spectrum antimicrobial hevamine A-related protein for use in nutraceutical compositions, methods for preventing or treating microbial infections in both humans and plants, and in the construction of disease-resistant transgenic plants.

SUMMARY

In one aspect, the present application provides a nutraceutical composition comprising an antimicrobial hevamine A-related protein comprising an amino acid sequence at least 95% identical to SEQ ID NO: 3 or SEQ ID NO: 4, and at least one nutraceutically acceptable carrier.

In one embodiment, the nutraceutical composition, further comprising one or more nutraceutical ingredients selected from the group consisting of antimicrobial agents, immune-stimulating agents, anti-inflammatory agent, antioxidant agent, and combinations thereof, wherein the one or more nutraceutical ingredients comprise zinc and quercetin.

In another embodiment, the nutraceutical composition formulated for oral, intravenous or intramuscular administration.

In another embodiment, the nutraceutical composition is formulated in the form of a capsule, a tablet or a lozenge.

Another aspect of the present applicant discloses a method of preparing the nutraceutical composition, comprising the steps of: drying a plant comprising a protein comprising an amino acid sequence at least 95% identical to SEQ ID NO:4; extracting the dried plant in an aqueous medium; and separating the aqueous medium from solid material to form an aqueous extract, wherein the aqueous extract comprises the protein.

In one embodiment, the method further comprises the step of purifying the protein from the aqueous extract by immunoaffinity purification to generate a purification product.

In another embodiment, the method further comprising the step of adding one or more nutraceutical ingredients to the purification product, wherein the one or more nutraceutical ingredients are selected from the group consisting of antimicrobial agents, immune-stimulating agents, anti-inflammatory agent, antioxidant agent, and combinations thereof, and wherein the one or more nutraceutical ingredients comprise zinc and quercetin.

In another embodiment, the method further comprises the step of: passing the aqueous extract through a molecular weight cut-off filter; collecting a retentate comprising the protein; and purifying the protein from the retentate to generate a purification product.

In another embodiment, the method further comprises further comprising the step of adding one or more nutraceutical ingredients to the purification product, wherein the one or more nutraceutical ingredients are selected from the group consisting of antimicrobial agents, immune-stimulating agents, anti-inflammatory agent, antioxidant agent, and combinations thereof, and wherein the one or more nutraceutical ingredients comprise zinc and quercetin.

Another aspect of the present application discloses a method for preventing or reducing symptoms of a condition in a subject, comprising administering to the subject an effective amount of the nutraceutical composition.

In one embodiment, the condition is microbial infection diseases, abnormal high energy metabolism or low energy metabolism.

In another embodiment, the higher energy metabolism is anemia, pregnancy, growth, exercise, cancers, recovery from surgical and other injuries.

In another embodiment, the low energy metabolism comprises malnutrition, anorexia, or aging.

In another embodiment, the microbial infection is caused by a virus, wherein the virus is HIV, influenza Type 1 virus, SARS-COV-2, SARS-COV-2 or MERS-COV.

In another embodiment, nutraceutical composition is administered to the subject orally, intravenously or intramuscularly.

Another aspect of the present application discloses a method of preventing or treating a microbial plant infection, comprising applying an effective amount of a composition, either pre- or post-infection, to a plant, plant part, or media in which a plant is growing, wherein the composition comprises an antimicrobial hevamine A-related protein comprising an amino acid sequence at least 95% identical to SEQ ID NO:3 or SEQ ID NO:4, wherein the plant part is selected from the group consisting of leaves, roots, stems, fruit, seeds, tubers, bulbs, flowers, pods, stems, shoots, and combinations thereof.

In one embodiment, the composition is applied by spraying a liquid or powder formulation to the plant, plant part, or a medium in which the plant is growing.

The present application further discloses a transgenic plant, transgenic plant part, or transgenic plant cell, comprising: a stably integrated DNA expression construct comprising: a polynucleotide comprising a nucleotide sequence at least 95% identical to SEQ ID NO: 1 or SEQ ID NO: 2, or a polynucleotide encoding a protein comprising an amino acid sequence at least 95% identical to SEQ ID NO:3 or SEQ ID NO:4, wherein the transgenic plant, transgenic plant part, or transgenic plant cell exhibits increased resistance to at least one bacterial, fungal or viral infection as compared to a control plant, plant part, or plant cell lacking the DNA expression construct.

In another embodiment the transgenic plant, transgenic plant part, or transgenic plant cell is derived from a crop plant selected from the group consisting of wheat, corn, rice, barley, cotton, canola, alfalfa, sugarbeet, potato and tomato.

The present application also describes a method of producing a transgenic plant, comprising the steps of: (a) stably transforming into a host plant a recombinant DNA expression construct comprising: a polynucleotide comprising a nucleotide sequence at least 95% identical to SEQ ID NO:1 or SEQ ID NO:2, or a polynucleotide encoding a protein comprising an amino acid sequence at least 95% identical to SEQ ID NO:3 or SEQ ID NO:4; and (b) isolating a transgenic plant expressing the stably transformed polynucleotide in an amount sufficient to provide increased resistance to a fungal, bacterial or viral infection as compared to a control plant lacking the polynucleotide under the same condition, wherein the host plant is a crop plant selected from the group consisting of wheat, corn, rice, barley, cotton, canola, alfalfa, sugarbeet, potato and tomato.

BRIEF DESCRIPTION OF THE DRAWINGS

FIG. 4A shows the results from using different size molecular weight cutoff filters to either retain (retentate) or pass through (filtrate) the inhibitory product in the plant extract. The plant extract (2 mg/ml stock) was passed through Amicon Ultra cutoff filters (3K, 10K, 30K, 100K and control (virus alone) and then mixed with 1 ng of p24 equivalent of virus before testing by MAGI assay. In each case the portion that flowed through the filter (solid bars) and a portion retained by the filter (hashed bars) was tested by the MAGI infectivity assay. F=filtrate (passes through filter) and R=retentate (retained by filter).

FIG. 4B shows that MoMo30 is heat stable and stays bound to virus for long periods of time. In FIG. 4B, HIV-1NL43 in an amount comprising 1 ng p24 was incubated with MoMo30 at concentrations of 1 nm (bottom curve) and 5 nm (top curve) sufficient to cause 50% or 70% inhibition, respectively. MoMo30 was pre-treated for 30 min at temperatures from 15 to 120° C. prior to mixing.

SDS-PAGE gel. The band is reactive with an N-terminal antibody to MoMo30.

FIG. 6 shows a Clustal Omega alignment of DNA sequences from *M. balsamina* MoMo30, the Hevamine A-like protein from *M. charantia*, and the MAP30 protein from *M. charantia*. Residues that are different are shaded. MoMo30 is 92% identical to the *M. charantia* hevamine A-like gene coding region and 26% identical to the *M. charantia* MAP30 protein.

FIG. 7A shows the MoMo30 coding region aligned with the hevamine A-related amino acid sequence from *Momordica charantia*, along with structural domain predictions thereof. Amino acids highlighted in red show differences between the two sequences. Arrows denote predicted beta sheet structures and hatched boxes denote areas of predicted alpha helical structure. The two yellow shaded boxes denote areas of conservation in this class of proteins. Asterisks denote highly conserved catalytic residues. FIG. 7B shows the amino acid sequence of the mature MoMo30 (i.e., secreted) protein.

FIG. 8 shows an alignment of two conserved regions from the MoMo30 protein against other hevamine A-related proteins.

FIG. 13A shows MoMo30 binding to purified gp120. In FIG. 13B, Gp120 pre-treated with PNGase F (an N-linked glycosylase) dramatically reduces binding. The three lines represent triplicate measurements.

FIG. 14A shows that mannose blocks the activity of MoMo30. HIV-1NL4-3, 400 ng of MoMo30 and different concentrations of D-mannose were incubated for 5 min at 37° C. and tested by a MAGI cell assay for inhibition of infection. Jurkat cells (1×107) were infected with 300 ng of HIV-1NL4-3 with or without 20 mg of MoMo30.

FIGS. 21A-21B show the results of a clinical study (n=61) in which HIV-1 infected patients were orally administered an herbal tea daily for 6 months containing Extracts A-E above. The results of this study showed a decrease in patients' HIV viral loads following a 6-month treatment with MoMo30 plant extract (FIG. 21A). FIG. 21B shows an increase in CD4+ lymphocytes following treatment with the MoMo30 plant extract.

In FIG. 22, panel C, a subset of the originally treated patients (n=13) were re-tested at 180 months. The results of this analysis showed that CD4 counts in most of the re-tested patients returned to near baseline levels. In addition, viral loads in ten of these re-tested patients had decreased to undetectable (<20 copies/ml); two patients had very low levels (~3000 copies/ml) and one was reported as (20 copies/ml) at 180 months post-treatment.

FIG. 23, panels A and B show the results of patients' serum being tested for neutralizing activity against HIV-1 pseudotyped with an HIV-1NL4-3 env or an aMLV env, respectively. FIG. 23, panel C shows a table depicting examples of antibody titers against 10 primary strains and 3 lab strains of HIV-1. The table summarizes reciprocal dilutions of the inhibitory dose to induce 50% reduction in replication of virus (ID 50). Darker shaded areas depict higher titers, while the lighter shaded areas depict lower titers.

Figure 1:
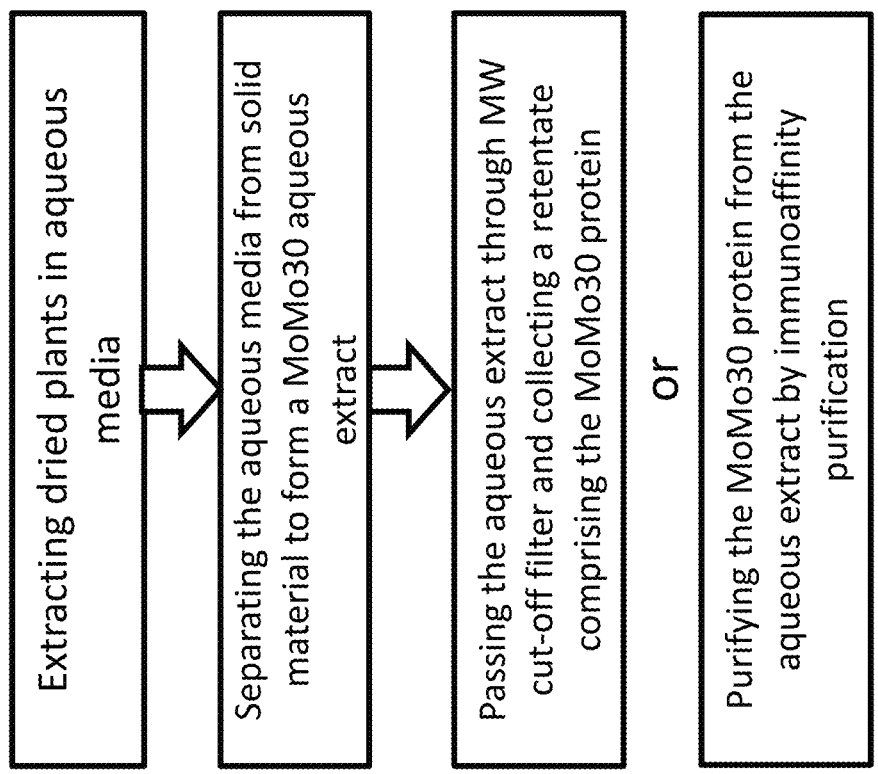
FIG. 1 shows an exemplary process for producing an aqueous plant extract from dried *Momordica balsamina* leaves.

While the present disclosure will now be described in detail, and it is done so in connection with the illustrative embodiments, it is not limited by the particular embodiments illustrated in the figures and the appended claims.

DETAILED DESCRIPTION

The invention and accompanying drawings will now be discussed in reference to the numerals provided therein to enable one skilled in the art to practice the present invention. The skilled artisan will understand, however, that the inventions described below can be practiced without employing these specific details, or that they can be used for purposes other than those described herein. Indeed, they can be modified and can be used in conjunction with products and techniques known to those of skill in the art considering the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

It will be appreciated that reference throughout this specification to aspects, features, advantages, or similar language does not imply that all the aspects and advantages may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but do not necessarily, refer to the same embodiment.

The described aspects, features, advantages, and characteristics of the present application may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention.

Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

Definitions

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used herein, the terms "hevamine A-related protein" and "MoMo30 protein" are used interchangeably with reference to an antimicrobial protein that can be isolated from e.g., *Momordica balsamina* leaves. In preferred embodiments, this protein comprises an amino acid sequence at least 95% identical to SEQ ID NO: 3 or SEQ ID NO: 4. In certain embodiments, the MoMo30 protein is obtained from a plant of the *Momordica* genus or a species therefrom, such as *Momordica balsamina* and others described herein, or any plant comprising a homolog thereof.

The term "hevamine A-related composition" refers to a composition comprising a hevamine A-related protein or MoMo30 protein.

As used herein, the term "MoMo30 homolog" refers to a MoMo30-related protein that is at least 90%, at least 91%, at least 92%, at least 93%, at least 94%, at least 95%, at least 96%, at least 97%, at least 98%, at least 99%, or 100% identical to the amino acid sequence of the *Momordica balsamina* MoMo30 protein set forth in SEQ ID NO: 3 or SEQ ID NO: 4.

The phrase "antimicrobial agent", "antimicrobial product" or "antimicrobial protein" are used interchangeably with reference to protein or small molecule compound that can inhibit the progression of a microbial infection, including those caused by viruses, bacteria, and *fungi*, or induce or mediate the death (e.g., necrosis or apoptosis) of infected cells in a subject (e.g., a human).

As used herein, the "subject is mammal or human."

As used herein, the term "nutraceutical composition" refers to a composition containing hevamine A-related protein or MoMo30 protein, optionally with one or more nutraceutical ingredients. The phrases "nutraceutical composition comprises" and "nutraceutical composition comprising" should be interpreted such that the "comprises" or "comprising" components are included in a single nutraceutical composition or in one or more independent nutraceutical compositions.

As used herein, the term "nutraceutical ingredient" is used with reference to any natural compound, substance, extract, or food that acts as a pharmaceutical agent alternative exhibiting at least one medical or health benefit when administered to a subject. Preferably, the medical or health benefit corresponds to an antimicrobial and/or immune-stimulating property. As used herein, the nutritional ingredient is added to a nutraceutical composition containing MoMo30. Exemplary nutraceutical ingredients include but are not limited to, antimicrobial agents, immune-stimulating agents, anti-inflammatory agent, antioxidant agent, and combinations thereof. The natural ingredients thereof may be prepared from natural sources, or they may be synthetically synthesized. The nutraceutical ingredients and MoMo30 protein can be contained in a medicinal format such as a capsule, tablet, or powder in a prescribed dose, or in a liquid or beverage.

As used herein, the phrase "nutraceutically acceptable carrier," refers to a substance that is not biologically or otherwise undesirable, i.e., the substance may be incorporated into a nutraceutical composition administered to a patient without causing any undesirable biological effects or interacting in a deleterious manner with any of the other components of the composition in which it is contained. Further, the nutraceutically acceptable carrier is used with reference to a nontoxic, inert solid, semi-solid, diluent, encapsulating material or formulation auxiliary of any type.

As used herein, the term "antioxidant" refers to natural substance that prevents or delays the oxidative deterioration of a compound.

The terms "treat" and "treatment" refer to the amelioration of one or more symptoms associated with a coronavirus infection; prevention or delay of the onset of one or more symptoms of a viral infection; and/or lessening of the severity or frequency of one or more symptoms of the infection.

The term "effective amount" is used with reference to the amount(s) of one or nutraceutical ingredients needed to provide a threshold level of active ingredients in the bloodstream or target tissue to provide a prophylactic or therapeutic effect. A "prophylactically effective amount" refers to an amount effective, at dosages and for periods of time necessary, to achieve the desired prophylactic result. A "therapeutically effective amount" refers to an amount effective, at dosages and for periods of time necessary, to achieve the desired therapeutic result. The precise amount of nutraceutical ingredients will depend upon numerous factors, e.g., the particular active agent, the components and physical characteristics of the composition, intended patient population, patient considerations, and the like, and can readily be determined by one skilled in the art, including based upon the information provided herein or otherwise available in the relevant literature.

The terms "codon optimized" and "codon optimization" refer to a process for modifying a nucleic acid sequence according to one or more of the following: (1) to match codon frequencies in a host organism target; (2) to promote increased expression; (3) to ensure proper folding; (4) to provide a GC content suitable for increasing mRNA stability or reducing secondary structures; (5) to minimize tandem repeat codons or base runs that may impair gene construction or expression; (6) to customize transcriptional and translational control regions; (7) to insert or remove protein trafficking sequences; (8) to remove/add post translation modification sites in an encoded protein (e.g. glycosylation sites); (9) to add, remove or shuffle protein domains; (10) to insert or delete restriction sites; (11) modify ribosome binding sites and mRNA degradation sites; (12) to adjust translational rates to allow the various domains of the protein to fold properly; or (13) to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

The term "control individual" is an individual who is not afflicted with the same microbial infection as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human.

Further, it should be understood that any reference to "HIV" or "HIV-1" should be construed as applying to any isolate or clade of HIV-1 or HIV-2.

I. Nutraceutical Compositions and Methods

The present application is directed to a nutraceutical composition comprising an antimicrobial hevamine A-related protein from plants, which has been found to possess antiviral, antibacterial and antifungal properties. The hevamine A-related protein may be orally administered alone, or preferably in combination with one or more nutraceutical ingredients further descried below.

In one aspect, the present application relates to a nutraceutical composition comprising an antimicrobial hevamine A-related protein comprising an amino acid sequence at least 90%, at least 95% identical, at least 99%, or 100% identical to SEQ ID NO: 3 or SEQ ID NO: 4, and at least one nutraceutically acceptable carrier for oral administration.

The MoMo30 product from *Momordica balsamina* is characterized by multiple properties, including: (1) an amino acid sequence of SEQ ID NO: 3 or SEQ ID NO: 4; (2) a size of about 30 kDa; (3) soluble in aqueous solutions; (4) high heat resistance or high stability as reflected in no appreciable loss of activity following autoclaving at 120° C. for 30 min; (5) mannose-sensitive binding to HIV gp120; (6) insensitive to digestion with trypsin following denaturation in 8M urea and overnight treatment and partially sensitive to subtilisin after overnight treatment; (7) an IC50 of about 32 pM in a MAGI cell indicator assay; (8) hemagglutinin activity; (9) capable of activating and stimulating T cell proliferation; (10) having chitinase activity; and (11) capable of preventing infection by HIV-1 or alleviating symptoms in an HIV-1 infected patient.

Without wishing to be bound by theory, MoMo30 is believed to be a carbohydrate binding agent with two distinct modes of action: (1) inhibition of virus by blocking entry into cells; (2) selecting for mutations in the viral envelope that allow the host to produce a broadly neutralizing antibody response. MoMo30 inhibits virus through binding carbohydrates. The more carbohydrates on the gp120, the more targets will be available for inhibiting virus. Under such pressure, the presence of the MoMo30 selects for virus with fewer glycosyl groups. Fewer glycosyl groups on gp120 allow more epitopes to be exposed and allows the production of neutralizing antibodies. Consequently, patients treated with MoMo30 in the short-term exhibit the production of a broadly neutralizing antibody response. The same patients should also develop a broadly neutralizing antibody response to control their infection in the long term.

In some embodiments, the MoMo30 protein (or homolog thereof) is encoded by a plant species of the *Momordica* genus. Exemplary *Momordica* species include, but are not limited to, *M. aculeata, M. acuminate, M. acutangula, M. adoensis, M. affinis, M. amaniana, M. angolensis, M. angulate, M. angustisepala, M. anigosantha, M. anthelmintica, M. argillicola, M. aspera, M. auriculata, M. balsamina, M. bequaertii, M. bicolor, M. boivinii, M. brachybotrys, M. bracteata, M. brevispinosa, M. bricchettii, M. cabraei, M. calantha, M. calcarata, M. camerounensis, M. cardiospermoides, M. carinata, M. casea, M. charantia, M. chinensis, M. cirrhiflora, M. cissoides, M. clarkeana, M. clematidea, M. cochinchinensis, M. cochinchinensis, M. cogniauxiana, M. cordata, M. cordatifolia, M. coriacea, M. corymbifera, M. covel, M. crinocarpa, M. cucullata, M. cylindrica, M. cymbalaria, M. dasycarpa, M. denticulata, M. denudata, M. dictyosperma, M. dioica, M. diplotrimera, M. dissecta, M. eberhardtii, M. echinata, M. echinocarpa, M. ecirrhata, M. elastica, M. elaterium, M. elegans, M. enneaphylla, M. erinocarpa, M. fasciculata, M. foetida, M. friesiorum, M. gabonii, M. garipensis, M. garriepensis, M. gilgiana, M. glabra, M. glauca, M. gracilis, M. grandibracteata, M. grosvenorii, M. guttata, M. hamiltoniana, M. hamiltoniana, M. henriquesii, M. heterophylla, M. heyneana, M. hispida, M. huberi, M. humilis, M. hystrix, M. indica, M. involucrata, M. jagorana, M. jeffreyana, M. kirkii, M. lambertiana, M. lanata, M. laotica, M. laurentii, M. leiocarpa, M. littorea, M. luffa, M. luffa, M. macrantha, M. macropetala, M. macrophylla, M. macropoda, M. macrosperma, M. maculata, M. mannii, M. marlothii, M. martinicensis, M. meloniflora, M. microphylla, M. missionis, M. mixta, M. monadelpha, M. morkorra, M. mossambica, M. multicrenulata, M. multiflora, M. muricata, M. obtusisepala, M. officinarum, M. operculata, M. ovata, M. paina, M. palmata E, M. papillosa, M. parvifolia, M. pauciflora, M. pedata, M. pedisecta, M. peteri, M. procera, M. pterocarpa, M. punctata, M. purgans, M. pycnantha, M. quinquefida, M. quinqueloba, M. racemiflora, M. racemosa, M. renigera, M. repens, M. reticulata, M. rostrata, M. rotunda, M. roxburghiana, M. rumphii, M. runssorica, M. rutshuruensis, M. sahyadrica, M. sativa, M. schimperiana, M. schinzii, M. schliebenii, M. senegalensis, M. sessilifolia, M. sicyoides, M. silvatica, M. sinensis, M. somalensis, M. sphaeroidea, M. spicata, M. spinosa, M. stefaninii, M. subangulata, M. surculata, M. suringarii, M. thollonii, M. tonkinensis, M. trifolia, M. trifoliata, M. trilobata, M. tuberosa, M. tubiflora, M. tubulosa, M. umbellata, M. verticillata, M. vogelii, M. wallichii, M. welwitschii, M. wildemaniana, M. zeylanica, and M. zeylanica*. In some embodiments, the MoMo30 protein may be obtained from any of the foregoing *Momordica* leaf extracts, fruit extracts, root extracts, bark extracts, seed extracts and/or any flower thereof.

In preferred embodiments, the nutraceutical composition is obtained from *Momordica balsamina* leaf extracts. In other embodiments, the nutraceutical composition is obtained from *Momordica balsamina* fruit extracts, root extracts, bark extracts, seed extracts and/or any flower thereof.

In one embodiment, the nutraceutical composition contains a MoMo30 protein or MoMo30 homolog comprising an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO: 3 or SEQ ID NO: 4 and contains at least one amino acid substitution relative SEQ ID NO:3 or SEQ ID NO: 4, respectively.

In some embodiments, the MoMo30 protein is a variant containing one or more mutations relative to the wild-type sequence. "Variants" include protein sequences having one or more amino acid additions, deletions, stop positions, or substitutions, as compared to a wild-type protein. An amino acid substitution can be a conservative or a non-conservative substitution. Variants of MoMo30 proteins can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that affect the structure of the peptide backbone in the area of alteration (e.g., the alpha-helical or beta-sheet structure); the charge or hydrophobicity of the molecule at the target site; or the bulk of the side chain. Non-conservative substitutions which in general are expected to produce the greatest changes in a protein's properties may include those in which e.g., (i) a hydrophilic residue (e.g., S or T) is substituted for (or by) a hydrophobic residue (e.g. L, I, F, V, or A); (ii) a C or P is substituted for (or by) any other residue; (iii) a residue having an electropositive side chain (e.g. K, R, or H) is substituted for (or by) an electronegative residue (e.g., Q or D); or (iv) a residue having a bulky side chain (e.g., F) that is substituted for (or by) one not having a bulky side chain, (e.g., G).

MoMo30 mutants may be generated by random mutagenesis or site-directed mutagenesis using methods known to those of ordinary skill in the art with or without selection methodologies employing MAGI indicator cell assays, apoptosis assays and the like.

In one embodiment, the MoMo30 protein or MoMo30 homolog comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO: 3 or SEQ ID NO: 4 and contains at least one amino acid substitution relative SEQ ID NO:3 or SEQ ID NO: 4, respectively.

In another aspect, the present application provides an expression vector comprising a MoMo30-encoded nucleic acid or a codon-optimized nucleic acid for expressing a MoMo30 protein. In certain embodiments, the expression vector encodes a MoMo30 protein containing at least one amino acid substitution relative SEQ ID NO:3 or SEQ ID NO: 4.

The MoMo30 protein may be derived from bacterial, fungal, plant, insect, or animal cells transformed with a MoMo30 expression vector to express the protein. The transformed cells may be stably transformed, or they may be transiently transformed. The MoMo30 protein or extract may be prepared, and its composition may be modified in accordance with any of the methods of preparation outlined below or known to those of ordinary skill in the art.

In some embodiments, the bacterial, fungal, plant, insect, or animal cells are transformed with a MoMo30 expression vector containing a MoMo30 encoded nucleic acid that is at least 95% identical to the nucleotide sequence of SEQ ID NO: 1 or SEQ ID NO: 2. In some embodiments, the nucleotide sequence comprises at least nucleotide substitution relative the nucleotide sequence of SEQ ID NO: 1 or SEQ ID NO: 2. In some embodiments, the MoMo30-encoded nucleic acid includes a codon-optimized nucleic acid coding region.

In some embodiments, the MoMo30 protein of the present application is expressed from a MoMo30 expression vector containing a codon-optimized nucleic acid coding region. In certain embodiments, the nucleic acid is codon optimized for expression in plant cells. In certain embodiments, the nucleic acid is codon optimized for expression in mammalian or human cells. In certain embodiments, the nucleic acid is codon optimized for expression in insect cells. In certain embodiments, the nucleic acid is codon optimized for expression in bacteria. In certain embodiments, the nucleic acid is codon optimized for expression in fungal cells.

Codon optimization methods are known in the art and may be used as provided herein. In some embodiments, the open reading frame (ORF) sequence in a polynucleotide is optimized using optimization algorithms as described herein and known in the art.

In some embodiments, the codon optimized MoMo30 polynucleotide sequence shares less than 95%, less than 90%, less than 85%, less than 80%, less than 75%, less than 70%, less than 65%, less than 60%, less than 55% or less than 50% sequence identity to SEQ ID NO: 1 or SEQ ID NO: 2.

In some embodiments, the codon optimized polynucleotide sequence shares between 50% and 95%, between 50% and 90%, between 50% and 85%, between 50% and 80%, between 50% and 75%, between 50% and 70%, between 50% and 65%, between 50% and 60%, between 50% and 55%, between 55% and 95%, between 55% and 90%, between 55% and 85%, between 55% and 80%, between 55% and 75%, between 55% and 70%, between 55% and 65%, between 55% and 60%, between 60% and 95%, between 60% and 90%, between 60% and 85%, between 60% and 80%, between 60% and 75%, between 60% and 70%, between 60% and 65%, between 65% and 95%, between 65% and 90%, between 65% and 85%, between 65% and 80%, between 65% and 75%, between 65% and 70%, between 70% and 95%, between 70% and 90%, between 70% and 85%, between 70% and 80%, between 70% and 75%, between 75% and 95%, between 75% and 90%, between 75% and 85%, between 75% and 80%, between 80% and 95%, between 80% and 90%, between 80% and 85%, between 85% and 95%, between 85% and 90%, or between 90% and 95% sequence identity to SEQ ID NO: 1 or SEQ ID NO: 2.

Nutraceutical Ingredients

In certain embodiments, the nutraceutical composition includes a MoMo30 protein or MoMo30-containing extract that is combined with one or more additional nutraceutical ingredients, particularly those exhibiting antimicrobial, antiviral, antibacterial, antifungal, immune boosting, anti-inflammatory, and/or antioxidant properties. Such nutraceuticals may include one or more phytochemicals, minerals and metals, vitamins, salts, amino acids, fatty acids, proteins, and other nutraceutically acceptable excipients.

Plants provide a prominent source of bioactive phytochemicals. Phytochemicals are produced during the natural course of plant growth and development that provide protection against microorganisms, insects or herbivores and serve as plant defense mechanisms against environmental stressful conditions, and. Phytochemicals such as carotenoids, phenolics, alkaloids, and organosulfur compounds are currently marketed for various medical or health benefits. Phytonutrients from many indigenous plants have been evaluated for antimicrobial, immune stimulating, anticancer, cardioprotective and brain enhancing effects. Many plants contain several distinct phytochemicals which may interact with multiple biological targets and provide numerous medical and health benefits for humans.

Phytochemicals extracted from plants or herbs include e.g., flavonoids, flavonols, terpenoids, lignans, sulfides, phenols, polyphenols, coumarins, saponins, furyl compounds, alkaloids, thiophenes, essential oils, alkaloids, lectins, proteins and peptides, and are present in volatile essential oils plants, herbs, spices, and herbal teas.

In some embodiments, the nutraceutical composition includes one or more herbs or herbal ingredients selected from the group consisting of oregano (including oregano oil and carvacrol), sage (including safficinolide and sage one), basil (including apigenin and ursolic acid), fennel (including trans-anethole), garlic, goldenseal, lemon balm, peppermint (including menthol and rosmarinic acid), rosemary (including oleanolic acid), *Echinacea, Sambucus*, black cumin seed, tea tree oil, olive leaf, myrrh extract, turmeric, licorice, *Astragalus*, ginger, ginseng, dandelion, berberine, and combinations thereof. Preferably the herbs and herbal ingredients have antimicrobial and/or immune-boosting properties.

In certain embodiments, the present application relates to the methods in treating the conditions by administering a subject in need an effective amount of the nutraceutical composition.

Conditions included but not limited to, i.e., microbial infection, abnormal high energy metabolism, i.e., anemia, pregnancy, growth, exercise, cancers; infectious disease and recovery from surgical and other injuries; low energy metabolism, i.e., malnutrition, anorexia, and aging.

In some embodiments, the nutraceutical composition includes one or more plant extracts or plant substances therefrom. Exemplary plant extracts or sources of MoMo30 homologs may be obtained from one or more members selected from the group consisting of *Acacia arabia, Afromomum melegueta, Agrimonia eupatoria, Ajuga decumbens, Allium cepa, Allium sativum, Aloe vera, Alternanthera philoxeroides* or *sessiles, Ammi maius, Andographis paniculata, Apium graveolens, Apium leptophyllum, Arachis hypogaea, Arctium lappa, Artemesia Judaica, Amebia euhcroma, Asparagus racemosus, Astragalus spinosus, Astragalus lentingosis swainsonine, Azadirachta indica, Balanites aegyptiaca, Bauhinia rufescens, Bersama tysoniana, Blumea alata, Brucea antidysenterica, Buchenavia capita, Butyrospermum parkii, Bryonia cretica* ssp. *Dioica, Bryonia angustifolia, Calotropis procera, Camellia sinensis* (green tea extract), *Camellia theifera, Casia sieberiana, Catha edulis. Cedrela toona, Chrysanthemum morifolium, Cinnamomum verum, Citrus limonia, Clausena anisata, Clivia miniata, Cochlospermum planchonii, Coffea arabica, Cola nitida, Combretum glutinosum, Combretum micranthum, Coptis chinesis, Coptis teetoides, Coptis japonica, Coraria nepalensis, Coriandrum sativum, Cryptolepis sanguinolenta, Curcuma longa, Cyperus articulatus, Cyperus domestus, Cyperus rigidifolius, Datura metel syn alba, Daucus carota, Diospyros mespiliformis, Echinacea angustiflora, Echinacea purpurea, Echinacea simulata, Echinacea pallida, Elettaria cardamomum, Entada abyssinica, Epimedium grandiflorum, Epimedium sagittatum, Epimedium sinense, Epilobium angustifolium, Erigeron Canadensis, Eugenia* or *Syzygium claviflorum, Euphorbia hirta, Faidherbia albida, Fagara xanthox, Ficus iteophylla, Ficus platphylla, Foeniculum vulgarel, Garcinia afzelii, Garcinia epundata, Gardenia coronaria, Gaultheria trichophylla, Glycine max, Glycyrrhiza glabra, Gossypium herbaceum, Guiera senegalensis, Heracleum sphondylium, Hypericum perforatum, Hypericum japonicum, Hyssopus officinalis, Jasminum officinale, Khaya senegalensis, Lippia javanica, Lithospermum erythrorhizon, Lonicera japonica, Lophira lanceolate, Luffa, Lycopus europaeus, Magnolia officinalis, Mallotus repandus, Mallotus philippinesis, Matricaria chamomil, Matricaria recutitia, Melissa parviflora, Melissa officinalis, Momordica* species, including *Momordica balsamina, Momordica charantia* and others; *Morus nigra* (black mulberry), *Morus rubra, Morinda lucida, Narcissus tazetta, Narcissus pseudonarcissus, Nigella sativa, Ocimum tenuiflorum, Ocimum gratissimum, Oenthera rosea, Paeonia* spec., *Panax ginseng, Papaver somniferum, Parkia biglobosa, Perilla frutescens, Persea americana, Phyllanthus amarus, Phyllanthus emblica, Phyllanthus niruri, Pimpinella anisum, Pinus koraicenis, Pinus maritima, Pinus parviflora, Piper nigrum, Plumeria rubra, Polyantha suberosa, Prosopis* sp., including *P. africana* and others; *Prunus africans, Prunella vulgaris, Prunus bakariensis, Prunus amygdalus, Psoralea corylifolia, Randia dunatorum, Raphanus sativus, Rheum palmatum, Rhus coriaria, Rhus chinesis, Ricinus communis, Rosmarinus officinalis, Salic mucronata, Salvia miltiorhiza, Salvia officinalis, Salvadora persica, Sambucus canadensis, Sambucus ebulus, Sambucus nigra* (elderberry), *Saussurea lappa, Scilla griffithii, Scutellaria baicalensis baiealein, Sedum sediforme, Senecio scandens, Senecio aereus, Senna alata, Silybum marianum, Skimmia laureola, Solarium niporum, Stevia rebaudiana, Swertia franchetiana, Syzygium aromaticum, Syzygium cumini, Tamarindus indica, Terminalia alata, Terminalia catappa, Terminalia chebula, Terminalia glaucescens, Thula occidentalis, Tinospora cordifoila, Trapalaponica* spec., *Trichosanthes dioica, Trichosanthes kirilowii, Uncaria tomentosa, Urtica dioica, Viola yeodensis, Vitellaria paradoxa, Voacanga africana, Withania somnifera, Woodfordia fruticosa, Woodwardia* spec., *Zanoxylum nitidum, Zanthoxylum zanthoxyloides, Zingiber officinale,* and *Ziziphus mauritania*, including extracts and polyphenols therefrom. Plant extracts and polyphenols therefrom may be included in powders and liquids of the present application, and may be extracted from leaves, bark, seeds, roots, fruits and/or flowers of plants. In some instances, the polyphenols and other natural nutraceutical ingredients described herein may be synthetically produced.

Exemplary plant-derived substances for inclusion in the nutraceutical compositions of the present application include lentinan, a polysaccharide isolated from the fruit body of shiitake mushroom (*Lentinula edodes* mycelium) and various ribosome inactivating proteins (RIPs) from e.g., *M. balsamina* and *Trichosanthis kirilowii*, such as Momordin I and Momordin II, as well as ribosome inactivating proteins (RIPs) from any of the foregoing plant extracts. It is believed that the addition of the nutraceutical ingredients may further increase the prophylactic and/or therapeutic efficacy of the MoMo30 protein, especially in patients with microbial infections or susceptible to microbial infections, such as the microbial infections described herein.

In some embodiments, the nutraceutical composition includes one or more natural substances with antimicrobial and/or immune-enhancing activity selected from the group consisting of quercetin, kaempferol, curcumin, hesperidin, resveratrol, lactoferrin, cinnamaldehyde, allicin, piperine, phycocyanobilin, astaxanthin, propolis, acetyl-L-carnitine, luteolin, apigenin, glycyrrhizin, caffeic acid, chlorogenic acid, epigallocatechin gallate (EGCG), Coenzyme Q10, omega-3 fatty acids, N-acetyl cysteine, colloidal silver, baicalin, linalool, eugenol, β-caryiphyllene, p-cymene, gingerol, allylisothiocyanate, carvacrol, o-cymophenol, capsaicin, carnosic acid, carnosol, rosmarinic acid, cineol, eucalyptol, thymol, nisin, β,β dimethylacryl shikonin and acetyl shikonin from *Achillea nobilis*; ursolic acid from e.g., rosemary and thyme; vasicine from e.g., *Adhatoda vasica*; sitosterol-D-glucopyranoside from e.g., *Desmostachya bipinnata*; probiotics (e.g., *Lactobacillus* sp., such as *L. paracasei, L. plantarum, L. rhamnosus, L. acidophilus; Lactococcus lactis, L. reuteri, B. bifidum*, and *L. bulgaricus; Bifidobacterium bifidum* and *Streptococcus thermopholis*).

In some embodiments, the nutraceutical composition includes one or more immune-stimulating agents selected from vitamin C, vitamin D, green tea extract, zinc, quercetin, elderberry, N-acetyl cysteine, baicalin, ferulic acid, lipoic acid, Brewer's yeast beta-glucan, and glucosamine.

In some embodiments, the nutraceutical composition includes one or more micronutrients or minerals, such as zinc, zinc citrate, zinc oxide, selenium, calcium, manganese gluconate, copper, copper gluconate, folate, iron, magnesium, boron sulfate, glucosamine sulfate, and chromium polynicotinate, including salts thereof.

In some embodiments, the nutraceutical composition includes one or more vitamins. Exemplary vitamins include, but are not limited to vitamin A, vitamin B1, vitamin B2, vitamin B5, vitamin B6, vitamin B7 (biotin), vitamin B9 (folate), vitamin B12, vitamin C, vitamin D, vitamin E, and vitamin K.

In some embodiments, the nutraceutical composition includes one or more fatty acids selected from the group consisting of linoleic acid (LA), gamma linoleic acid (GLA), eicosapentaneoic acid (EPA), docosapentaneoic Acid (DPA), docosahexaenoic acid (DHA), palmitoylethanolamide, short-chain fatty acids (SCFA), medium-chain fatty acids (MCFA), and D-alpha-tocopherol.

In some embodiments, the nutraceutical composition includes one or more antioxidants. As used herein "antioxidant" refers to any substance which inhibits, suppresses, or reduces oxidative damage to cells and biomolecules. Examples of suitable antioxidants for embodiments of this application include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, vitamin A, vitamin C, vitamin E, ubiquinone, mineral selenium, manganese, melatonin, a-carotene, β-carotene, lycopene, lutein, zeanthin, crypoxanthin, reservatol, eugenol, quercetin, glutathione, catechin, gossypol, hesperetin, curcumin, ferulic acid, thymol, hydroxytyrosol, spirulina, turmeric, thyme, olive oil, lipoic acid, glutathione, glutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyanidin, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-a-lipoic acid, N-acetyl cysteine, emblicanin, apple extract, apple skin extract (applephenon), rooibos extract red, rooibos extract, green, hawthorn berry extract, red raspberry extract, green coffee antioxidant (GCA), *aronia* extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, *Citrus* bioflavonoids, black currant, ginger, acai powder, green coffee bean extract, green tea extract, and phytic acid, or combinations thereof.

In some embodiments, the nutraceutical composition is in dried form. In particular embodiments, the dried form is a powdered form, granulated form, capsule, tablet, lozenge, or herbal tea extract.

In some embodiments, the present application provides a liquid containing a dried form of the nutraceutical composition in beverage, such as water, carbonated water, juice, herbal tea, soft drinks, energy drinks, or milk. In certain embodiments, the beverage provides one or more natural sweeteners.

Liquid preparations for oral administration can take the form of, for example, elixirs, solutions, syrups or suspensions, or they can be presented as a dry product for constitution with water or other suitable liquids described herein before use. Such liquid preparations can be prepared by conventional means with nutraceutically acceptable additives such as suspending agents (e.g., sorbitol syrup, cellulose derivatives or hydrogenated edible fats); emulsifying agents (e.g., lecithin or *Acacia*); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Nutraceutical Composition Formulations and Methods of Preparation

Another aspect of the application relates to a method of preparing a MoMo30 containing nutraceutical composition or purified MoMo30 protein, including but not limited to plants of the *Momordica* genus, such as *Momordica balsamina*. In preferred embodiments, the MoMo30 protein is obtained from *Momordica balsamina* leaf extracts. In other embodiments, the nutraceutical composition is obtained from *Momordica balsamina* fruit extracts, root extracts, bark extracts, seed extracts and/or any flower thereof.

In one embodiment, the method includes one or more steps including: harvesting the plants; drying the plants; extracting the dried plants in water or aqueous media to form an aqueous extract; and centrifuging the aqueous extract to remove debris and particulates.

Given that MoMo30 retains its activity in a MoMo30-containing extract after boiling, in some embodiments, the MoMo30 protein is purified by boiling the extract for 20 min to inactivate other proteins in the extract.

In some embodiments, the aqueous MoMo30 extract is passed through a molecular weight cutoff (MWCO) filter (e.g., Amicon 30 kDa or 50 kDa); the retentate containing MoMo30 protein is collected; the MoMo30 protein eluted from the retentate; drying the protein in the retentate or resuspending the protein in buffer for further analysis, purification and/or storage. The MoMo30 protein may be further purified from the plant extract by immunoaffinity chromatography and other conventional methodologies known to those of skill in the art. In some embodiments, plant leaves comprising a MoMo30 protein are obtained from members of the *Momordica* genus, such as *Momordica balsamina*.

In a particular embodiment, a method for preparing a MoMo30-containing plant extract comprises the steps of: (a) drying a plant comprising an MoMo30 protein; (b) extracting the dried plant in aqueous media; (c) separating the aqueous media from solid material to form an aqueous MoMo30 extract; and (d1) passing the aqueous extract through a molecular weight cut-off filter and collecting a retentate comprising the protein, or (d2) purifying the protein from the aqueous extract by immunoaffinity purification using an antibody directed against the protein.

In another embodiment, a method for preparing a MoMo30-containing plant extract comprises the steps of: (a) drying a plant comprising an MoMo30 protein; (b) extracting the dried plant in boiling water; and (c) separating the aqueous media from solid material to form an aqueous MoMo30 extract.

The MoMo30 protein may be dried for storage or resuspended in an appropriate buffer for further use or storage following e.g., quantification of MoMo30 yield and/or characterization of MoMo30 purity. In practice, the extracts are highly stable and have been stored freeze dried for years without significant loss of anti-viral activity.

In addition, the extract, purified extract and/or purified MoMo30 protein may be characterized by HPLC and/or tested for functional activity via infectivity assays and the like. For example, in some embodiments, the MoMo30-containing plant extract or purified protein may be evaluated for functional activity by testing their ability to inhibit infection by HIV using a MAGI cell infectivity assay (or "indicator assay"). This assay involves the use of genetically modified CD4-expressing HeLa cell line (MAGI) containing an HIV LTR-driven cassette placed upstream of the E. coli β-gal encoded reporter gene (HeLa-CD4-LTR-β-gal). See Kimpton and Emerman, J. Virol., 66:2232, 1992. Expression of the reporter gene is activated in the presence of HIV Tat, which is expressed upon infection by HIV, such as HIV-1NL4-3 and activates the HIV-1 LTR. Cells infected by HIV turn blue and can be counted under a microscope.

The nutraceutical compositions of the present application can be manufactured by methods of conventional mixing, dissolving, granulating, dragee-making levigating, emulsifying, encapsulating, entrapping or lyophilization processes. The compositions can be formulated in conventional manner using one or more nutraceutically acceptable carriers, including excipients, binders, diluents, antiadherents, coatings, disintegrants, flavors, colors, lubricants, glidants, sorbents, preservatives, sweeteners or auxiliaries that facilitate processing of the compositions into preparations that can be used.

Exemplary excipients include, but are not limited to binders, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, hydroxypropylmethylcellulose. hypromellose, rice flour, rice bran oil, gelatin, vegetable glycerin, lecithin, magnesium stearate, cellulose, inulin, and silicon dioxide.

As used herein, the term "binder" refers to substances that are added to powdered particles, generally prior to granulation or direct compression, to achieve the requisite flow property and/or compressibility necessary for effective compression of the powdery particles and/or granules into a tablet, lozenge, or capsule, or to improve certain physical properties of the powdered particles including but not limited to increasing the cohesive nature of the powdered particles in forming granules, tablets, lozenges, capsules, and other solid dosage forms.

Exemplary binders include, but are not limited to cellulose and cellulose derivatives (e.g. microcrystalline cellulose, methylcellulose (MC), sodium carboxymethyl cellulose (CMC), hydroxypropyl methylcellulose (HPMC, hypromellose), hydroxyethyl cellulose (HEC), and hydroxypropylcellulose (HPC); cellulose ethers; starch derivatives (including pregelatinized and granulated starches, dextrin, and maltodextrin); arabogalactan; sugars (e.g., glucose, dextrose, lactose, and sucrose); sugar alcohols (e.g., mannitol, sorbitol, xylitol, erythritol, maltitol, and isomalt); polymers (e.g., like polyvinylpyrrolidone (PVP, povidone), polyvinyl alcohol (PVA), polyacrylamides, poly-methyacrylamides, polyoxazolines (POZ), polyphosphates, and polyethylene glycol (PEG)); copolymers (e.g., divinyl ether-maleic anhydride); vegetable waxes (e.g., camauba wax), gelatins and gelatin-like products (e.g., agar); pectins; oligosaccharides or polysaccharides (e.g., inulin and xanthan gum); and dietary fiber (e.g., chicory root and chicory root extracts); gelatin, molasses, Acacia gum, panwar gum, ghatti gum, sodium alginate, Irish moss extract, mucilage of isapgol husks, Veegum and combinations thereof. Exemplary lubricants include, but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the hevamine A-related protein composition. Also, glidants, such as but not limited to, colloidal silicon dioxide or talc may be added to improve the flow characteristics of a powdered ingredient. Finally, disintegrants, such as but not limited to, starches, clays, celluloses, algins, gums, crosslinked polymers (e.g., croscarmelose, crospovidone, and sodium starch glycolate), Veegum, methylcellulose, agar, bentonite, cellulose and wood products, natural sponge, cation-exchange resins, alginic acid, guar gum, Citrus pulp, carboxymethylcellulose, or sodium lauryl sulfate with starch may also be added to facilitate disintegration of the active ingredients in the intestine.

In some embodiments, the nutraceutical composition is in dried form. In particular embodiments, the dried form is a powdered form, granulated form, capsule, tablet, lozenge, or herbal tea extract.

In certain embodiments, the dried form is agitated or dissolved in a liquid, such as water, carbonated water, juice, herbal tea, soft drinks, energy drinks, or milk. The nutraceutical ingredients described herein may be powdered or granulated prior to being incorporated into the nutraceutical composition.

In certain embodiments, one or more of the nutraceutical ingredients may be powdered or granulated to a particle size between about 10 microns and about 300 microns, and more particularly between about 100 microns and about 200 microns. However, one of ordinary skill in the art may select other suitable particle sizes, including particle sizes adapted to facilitate water solubility of the nutraceutical compositions as further described herein, as desired. Furthermore, each of these nutraceutical ingredients may be substantially evenly mixed together according to conventional techniques to provide the nutraceutical composition for convenient end use.

In particular embodiments, the ingredients are provided in a dosage form suitable for oral administration, including one or more tablets or artificial capsules, a manufactured or compounded liquid or slurry form, or as a manufactured powder or granulate.

As a nonlimiting example, the powder or granulate form of the nutraceutical formulation may be water soluble. In particular, the nutraceutical formulation may be ground to, or otherwise provided in, a particle size that is adapted to naturally dissipate and dissolve within an aqueous medium. It should be appreciated that where the powdered or granulated ingredients of the nutraceutical formulation are dehydrated, the ingredients will furthermore more readily absorb water and dissolve in the aqueous medium, especially in comparison to synthetic vitamin alternatives. One of ordinary skill in the art may also select other suitable dosage forms within the scope of the present disclosure.

It should be appreciated that the capsule dosage form for the nutraceutical formulation may be preferred. Where provided in a capsule dosage form, the artificial capsules may be single-piece or two-piece manufactured bodies for encapsulation of the formulation. Suitable ingredients for the manufactured capsules may include, but are not limited to wax, cellulose (including, for example, Hypromellose or HPMC, and sometimes referred to as "veggie capsule"), starches, gelatin, pullulan/tapioca, and combinations thereof. Other suitable ingredients for capsules of the present disclosure may also be employed, as desired.

One of ordinary skill in the art may also select other suitable dosage forms and capsule types within the scope of the present application.

In some embodiments, a dried nutraceutical composition is enclosed within an edible film which dissolves upon agitation or contact with a beverage, such as water, carbonated water, juice, herbal tea, soft drinks, energy drinks, or milk. In some embodiments, the edible film comprises one or more ingredients selected from the group consisting of polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium aginate, polyethylene glycol, xanthan gum, tragancanth gum, guar gum, *Acacia* gum, arabic gum, polyacrylic acid, methylmethacrylate copolymer, carboxyvinyl copolymers, starch, modified food starch, gelatin, ethyl cellulose, hydroxypropyl ethyl cellulose, cellulose acetate phthalate, or hydroxypropyl methyl cellulose phthalate, and combinations thereof.

In some embodiments, the method of encapsulating the nutraceutical powder compositions may include forming a cavity in the film; filling the cavity with the nutritional powder composition; and sealing the film. Another method of encapsulating the nutritional powder composition may include creating a back and bottom seal with the film; filling the film with the nutritional powder composition; and creating a top seal with the film. Compositions and methods for enclosing nutritional compositions within an edible film are described in U.S. Patent Publication No. 2018/0290804, the disclosure of which is incorporated by reference in its entirety.

In some embodiments, the present application provides a liquid containing a dried form of the nutraceutical composition in a beverage, such as water, juice, herbal tea, soft drinks, energy drinks, or milk. In certain embodiments, the beverage provides one or more natural or synthetic sweeteners.

In certain embodiments, the natural sweetener is a high intensity sweetener selected from one or more *Stevia* extracts (i.e., from *Stevia rebaudiana*) and steviol glycosides therefrom including e.g., rebaudioside A and rebaudioside D; monk fruit extracts (from *Siraitia grosvenorii*) and mogrosides therefrom; sweet tea extracts (from *Rubus suavissimus*) and suaviosides therefrom; and combinations thereof.

In other embodiments, the beverage provides one or more natural or synthetic sweeteners selected from the group consisting of aspartame (e.g., NutraSweet), sucralose (Splenda), acesulfame potassium (also known as acesulfame K, or Ace-K), advantame, sorbitol, xylitol, mannitol, neotame, erythritol, trehalose, raffinose, cellobiose, tagatose, allulose, inulin, N—[N-[3-(3-hydroxy-4-methoxyphenyl) propyl]-alpha-aspartyl]-L-phenylalanine 1-methyl ester, glycyrrhizin, sodium cyclamate, brazzein, miraculin, curculin, pentadin, mabinlin, NHDC, thaumatin, naringin dihydrochalcone, maltol, ethyl maltol, advantame, and combinations thereof.

Liquid preparations for oral administration can take the form of, for example, solutions, elixirs, syrups or suspensions, or they can be presented as a dry product for constitution with water or other suitable liquids described herein before use. Such liquid preparations can be prepared by conventional means with nutraceutically acceptable additives such as suspending agents (e.g., sorbitol syrup, cellulose derivatives or hydrogenated edible fats); emulsifying agents (e.g., lecithin or *Acacia*); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

In some embodiments, the nutraceutical composition includes a MoMo30 protein expressed from an expression vector by recombinant DNA technology.

An "expression vector" is used herein with reference to a non-viral or viral vector containing a polynucleotide encoding an antimicrobial MoMo30 protein of the present application in a form suitable for expression of MoMo30 in a host cell. The expression vectors include one or more regulatory sequences, selected based on the host cells used for expression, and operably linked to the polynucleotide sequence to be expressed. It will be appreciated by those skilled in the art that the design of the expression vector can depend on such factors as the choice of the host cell to be transformed, the level of expression of protein desired, and the like.

As used herein, the term "control sequences" or "regulatory sequences" refers to DNA sequences necessary for the expression of an operably linked coding sequence in a particular host organism. The term "control/regulatory sequence" is intended to include promoters, enhancers, and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences). An expression vector may be designed to facilitate expression of an antimicrobial MoMo30 protein-encoding polynucleotide in one or more cell types. Tissue-specific regulatory elements may be used to restrict expression to a particular cell type.

A nucleic acid sequence is "operably linked" to another nucleic acid sequence when the former is placed into a functional relationship with the latter. For example, a DNA for a presequence or secretory leader peptide is operably linked to DNA for a protein if it is expressed as a preprotein that participates in the secretion of the protein; a promoter or enhancer is operably linked to a coding sequence if it affects the transcription of the sequence; or a ribosome binding site is operably linked to a coding sequence if it is positioned so as to facilitate translation. By contrast, enhancers need not be contiguous with e.g., promoters. As used herein, the term "preprotein" is used with reference to a predicted amino acid sequence including an N-terminal signal peptide, which is cleaved off during protein processing resulting in a secreted biologically active mature protein as described herein.

As used herein, the term "promoter" related to an expression control element for a structural gene and to which RNA polymerase specifically binds and initiates RNA synthesis (transcription) of that gene. The term promoter is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers and silencers) which regulate activation or repression of genes operably linked thereto in response to developmental and/or external stimuli and transacting regulatory proteins or nucleic acids. The promoter may be constitutively active, or it may be active in one or more tissues or cell types in a developmentally regulated manner. A promoter may contain a genomic fragment, or it may contain a chimera of one or more TREs combined.

Examples of promoters include: the immediate early promoter of CMV, LTR or SV40 promoter, polyhedron promoter of baculovirus, *E. coli* lac or trp promoter, phage T7 and lambda PL promoter and other promoters known to control expression of genes in prokaryotic or eukaryotic cells or their viruses. The expression vector typically also contains a ribosome binding site for translation initiation and a transcription terminator. The vector includes appropriate sequences for amplifying expression. In addition, the expression vectors comprise one or more selectable marker genes to provide a phenotypic trait for selection of transformed host cells, such as dihydrofolate reductase or neomycin resistance for eukaryotic cell culture or such as tetracycline or ampicillin resistance in *E. coli*.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a protein coding sequence or a portion thereof, is inserted, exogenous translational control signals, including an ATG initiation codon is provided for expression of an antimicrobial MoMo30 protein. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use.

Expression vectors carrying an antimicrobial MoMo30-encoding nucleic acid can be introduced into host cells by any of a variety of well-known procedures, such as electroporation, calcium phosphate precipitation liposome mediated transfection, infection, transfection, and the like, depending on the selection of vectors and host cells.

Host cells that contain antimicrobial MoMo30 protein-encoding nucleic acids are, thus, also a feature of this disclosure. Favorable host cells include prokaryotic (i.e., bacterial) host cells, such as *E. coli*, as well as numerous eukaryotic host cells, including plant (e.g., tobacco), fungal (e.g., yeast, such as *Saccharomyces cerevisiae* and *Picchia pastoris*) cells, insect cells, and mammalian cells (such as CHO cells). Recombinant antimicrobial MoMo30-encoding nucleic acids are introduced (e.g., transduced, transformed, or transfected) into host cells, for example, via a vector, such as an expression vector. As described above, the vector is most typically a plasmid, but such vectors can also be, for example, a viral particle, a phage, etc. Examples of appropriate expression hosts include bacterial cells, such as *E. coli, Streptomyces*, and *Salmonella typhimurium*; fungal cells, such as *Saccharomyces cerevisiae, Pichia pastoris* and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants or amplifying the inserted polynucleotide sequences. The culture conditions, such as temperature, pH, and the like, are typically those previously used with the host cell selected for expression and will be apparent to those skilled in the art.

In bacterial systems, a number of expression vectors can be selected depending upon the use intended for the expressed product. For example, when large quantities of a protein or fragments thereof are needed for the production of antibodies, vectors which direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with e.g., sequences for the amino-terminal translation initiating methionine and the subsequent 7 residues of beta-galactosidase producing a catalytically active beta galactosidase fusion protein in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number of expression systems, including both plasmids and viral-based systems, can be utilized.

A host cell is chosen for its ability to modulate the expression of the inserted sequences or to process the expressed protein in the desired fashion. Such modifications of the protein include, but are not limited to, glycosylation, acetylation, carboxylation, phosphorylation, lipidation, acylation etc. Post-translational processing for example, which cleaves a precursor form into a mature form of the protein (for example, by a furin protease) is performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant antimicrobial MoMo30 protein, stable expression systems may be employed. For example, polynucleotides encoding an antimicrobial MoMo30 protein can be introduced into suitable host cells using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding an antimicrobial MoMo30 protein are cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted protein product is then recovered from the culture medium. Alternatively, cells can be harvested by centrifugation, disrupted by physical or chemical means and the resulting crude extract retained for further purification. Eukaryotic or microbial cells employed in expression of proteins can be disrupted by any convenient method, including freeze-thaw cycling, sonication, mechanical disruption or use of cell lysing agents or other methods, which are well known to those skilled in the art.

Expressed antimicrobial MoMo30 proteins can be recovered and purified from recombinant cell cultures by any of a number of methods well known in the art, including ammonium sulfate or ethanol precipitation, acid extraction, anion, or cation exchange chromatography, phosphocellulose chromatography, hydrophobic interaction chromatography, affinity chromatography (e.g., using any of the tagging systems noted herein), hydroxylapatite chromatography and lectin chromatography. Since the MoMo30 protein is unusually heat stable it also suggests that application of heat to denature other proteins may be a useful approach. Protein refolding steps can be used, as desired, in completing configuration of the mature protein. Finally, high performance liquid chromatography (HPLC) can be employed in the final purification steps.

In some embodiments, the MoMo30-encoded expression vector is introduced into a suitable bacterial host. Numerous suitable strains of E. coli are available and can be selected by one of skill in the art (for example, the Rosetta and BL21 (DE3) strains).

In other embodiments, the MoMo30-encoded expression vector is introduced into insect cells using a baculovirus expression vector system (BEVS). Recombinant baculovirus capable of infecting insect cells can be generated using commercially available vectors, kits and/or systems, such as the BD BaculoGold system from BD BioScience. Briefly, the polynucleotide sequence encoding the antimicrobial product is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the antimicrobial product is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the SF9 and the High Five (Hi5) cell line derived from a cabbage looper, *Trichoplusia ni*.

Following transfection and induction of expression (according to the selected promoter and/or enhancers or other regulatory elements), the expressed proteins are recovered (e.g., purified or enriched) and renatured to ensure folding into a biologically active conformation.

Methods of Using the Nutraceutical Composition

In another aspect, the present application provides a method for preventing or treating a microbial infection. In one embodiment, the method comprises orally administering to a subject a nutraceutical composition comprising MoMo30 protein alone or in a combination formulation with or without additional nutraceutical ingredients as described above in an amount sufficient to prevent a microbial infection, reduce the symptoms associated with the infection, or cure the subject of the microbial infection or disease. The nutraceutical composition may be administered as a MoMo30 protein or MoMo30 extract alone or in combination with other nutritional ingredients, plant extracts or plant components described above.

In some embodiments, the nutraceutical composition is administered in a dried form, such as a capsule, tablet, lozenge, or powder with at least one nutraceutically acceptable carrier.

In some embodiments, the nutraceutical composition is administered as a liquid or beverage with or without one or more other nutraceuticals. The liquid may be, for example, a beverage, such as water, juice, herbal tea, soft drink, energy drink, milk, and others known in the art.

In one embodiment, the nutraceutical composition is administered as one or more herbal extracts derived from a natural plant source, such as *M. balsamina*. Further, plant extracts may be used to isolate purified or semi-purified MoMo30 protein or any of the plant nutraceutical ingredients described herein.

In some embodiments, the composition is used to prevent or treat an infection caused by a virus.

In other embodiments, the composition is used to prevent or treat an infection caused by a bacterium.

In other embodiments the composition is used to prevent or treat an infection caused by a fungus.

In other embodiments, the composition is used to prevent or treat an infection caused by a protozoa.

In certain preferred embodiments, the virus, bacterium, fungus, or protozoa includes one or more cell surface proteins containing one or more sugar residues, such as mannose, sialic acid, glucose, glucuronic acid, xylose, fucose, galactose, N-acetylglucosamine, N-acetylgalactosamine, and/or iduronic acid.

Exemplary viruses for prevention or treatment include a variety of enveloped RNA and DNA viruses, including RNA viruses, such as retroviruses, lentiviruses, coronaviruses (including subgroup 1a and 1b alphacoronaviruses, subgroup 2a, 2b, 2c and 2d betacoronaviruses, and subgroup 3 gammacoronaviruses), herpesviruses, alphaviruses, bunyaviruses, filoviruses, flaviviruses, hepatitis viruses, orthomyxoviruses (e.g., influenza Types A, -B, -C, -D), paramyxoviruses, rhabdoviruses, and togaviruses; and DNA viruses, such as herpesviruses, poxviruses, and hepadnaviruses. In certain preferred embodiments, the infection is caused by HIV, SARS-COV-2, or an influenza Type 1 virus.

Exemplary species of enveloped viruses for prophylactic or therapeutic use include retroviruses or lentiviruses, such as human immunodeficiency virus type 1 and type 2 (HIV-1 and HIV-2), human T-cell lymphotropic virus type I and type II (HTLV-I and HTLV-II); herpesviruses, including Epstein-Barr virus, human cytomegalovirus type 1 (HCMV-1), human herpes virus type 6 (HHV-6), human herpes virus type 7 (HHV-7), human herpes virus type 8 (HHV-8), influenza type A virus, including subtypes H1N1 and H5N1, as well as types-B, -C, and -D; coronaviruses, including severe acute respiratory syndrome coronavirus type 2 (SARS-CoV-2), SARS-COV-1, Middle East Respiratory Syndrome Coronavirus (MERS-COV), HCoV-229E, HCoV-OC43, HCoV-NL63, and HCoV-HKU1; RNA viruses that cause hemorrhagic fever, such as the filoviruses, Ebola virus (EBOV) and Marburg virus (MBGV); Bunyaviridae (e.g., Rift Valley fever virus (RVFV) and Crimean-Congo hemorrhagic fever virus (CCHFV)); and flaviviruses, such as Hepatitis C virus, West Nile virus (WNV), Dengue fever virus (DENV), yellow fever virus (YFV), tick-borne encephalitis virus, Saint Louis encephalitis virus, and (GB virus C (GBV-C), formerly known as Hepatitis G virus (HGV)); enteroviruses (Types A to L, including coxsackieviruses (Types A to C); echoviruses; rhinoviruses (Types A to C), poliovirus); orthomyxoviruses (e.g., influenza Types A, -B, -C, -D, including A subtypes H1N1, H5N1, H3N2); paramyxoviruses (e.g., rubulavirus (mumps), rubeola virus (measles), respiratory syncytial virus, Newcastle disease, parainfluenza); parvoviruses (e.g., parvovirus B19 virus); rhabdoviruses (e.g., Rabies virus); arenaviruses (e.g., lymphocytic choriomeningitis virus and several Lassa fever viruses, including Guanarito virus, Junin virus, Lassa virus, Lujo virus, Machupo virus, Sabia virus, Whitewater Arroyo virus); alphaviruses (e.g., Venezuelan equine encephalitis virus, eastern equine encephalitis virus; western equine encephalitis virus); hepatitis A virus, hepatitis C virus (HCV), hepatitis D virus (HDV), hepatitis E virus (HEV), including any type, subtype, clade or sub-clade of the foregoing viruses.

In certain preferred embodiments, the RNA virus for prevention or treatment is a coronavirus, such as SARS-COV-2, SARS-COV-1, MERS-COV, HCOV-229E, HCoV-OC43, HCoV-NL63, and HCoV-HKU1. In an exemplary embodiment, a method for preventing or reducing symptoms of a coronavirus infection, comprises orally administering to a subject in need thereof a composition comprising: an effective amount of a MoMo30 protein comprising an amino acid sequence that is at least 90% identical to SEQ ID NO: 4; and at least one nutraceutically acceptable carrier.

In other preferred embodiments, the RNA virus for prevention or treatment is an influenza Type A virus. Influenza A viruses are divided into subtypes on the basis of two proteins on the surface of the virus, hemagglutinin (HA) and neuraminidase (NA). There are 18 known HA subtypes and 11 known NA subtypes. Many different combinations of HA and NA proteins are possible. For example, an "H7N2 virus" designates an influenza A virus subtype that has an HA7 protein and an NA2 protein. Similarly, an "H5N1" virus has an HA5 protein and an NA1 protein. Type A influenza viruses that may be targeted for prophylactic and/or therapeutic use according to the methods and compositions of the present application include a variety of sub-types, such as HIN1, HIN2, H3N2, H5N1, H5N2, H5N3, H5N4, H5N5, H5N6, H5N7, H5N8, and H5N9, H7N1, H7N2, H7N3, H7N4, H7N5, H7N6, H7N7, H7N8, H7N9, H9N1, H9N2, H9N3, H9N4, H9N5, H9N6, H9N7, H9N8, H9N9, H17N10 and H18N11).

In another exemplary embodiment, a method for preventing or reducing symptoms of an influenza Type A virus infection, comprises orally administering to a subject in need thereof a composition comprising: an effective amount of a MoMo30 protein comprising an amino acid sequence that is at least 90% identical to SEQ ID NO: 4; and at least one nutraceutically acceptable carrier.

Exemplary species of enveloped DNA viruses for prevention or treatment include, but are not limited to, Exemplary DNA viruses for prophylactic or therapeutic treatment include herpesviruses (e.g., HSV-1, HSV-2, EBV, VZV, HCMV-1, HHV-6, HHV-7, HHV-8), papillomaviruses (e.g., human papilloma virus (HPV) Types 1, 2, 4, 6, 11, 16, 18, 26, 30, 31, 33, 34, 35, 39, 40, 41, 42, 43, 44, 45, 51, 52, 54, 55, 56, 57, 58, 59, 61, 62, 64, 67, 68, 69, 70); poxviruses (e.g., smallpox virus), hepadnaviruses (Hepatitis B virus); anelloviruses (e.g., transfusion transmitted virus or torque teno virus (TTV); as well as any type, subtype, clade or sub-clade thereof.

In some embodiments, the MoMo30 protein is used for the treatment or prevention of bacterial infection. Exemplary bacteria for treatment include, but are not limited to, *Staphylococcus* species, including *S. epidermidis*, *S. aureus*, and methicillin-resistant *S. aureus*; *Enterococcus* species, including *E. faecalis* and *E. faecium*; *Mycobacterium tuberculosis*, *Haemophilus influenzae*, *Pseudomonas* species, including *P. aeruginosa*, *P. pseudomallei*, and *P. mallei*; *Salmonella* species, including *S. enterocolitis*, *S. typhimurium*, *S. enteritidis*, *S. bongori*, and *S. choleraesuis*; *Shigella* species, including *S. flexneri*, *S. sonnei*, *S. dysenteriae*, and *S. boydii*; *Brucella* species, including *B. melitensis*, *B. suis*, *B. abortus*, and *B. pertussis*; *Neisseria* species, including *N. meningitidis* and *N. gonorrhoeae*; *Escherichia coli*, including enterotoxigenic *E. coli* (ETEC); *Vibrio cholerae*, *Helicobacter pylori*, *Chlamydia trachomatis*, *Clostridium difficile*, *Cryptococcus neoformans*, *Moraxella catarrhalis*, *Campylobacter* species, including *C. jejuni*; *Corynebacterium* species, including *C. diphtheriae*, *C. ulcerans*, *C. pseudotuberculosis*, *C. pseudodiphtheriticum*, *C. urealyticum*, *C. hemolyticum*, *C. equi*; *Streptococcus* species, including *S. pneumoniae*, *S. pyogenes*, *S. mutans*, *S. agalactiae*, *S. equi*, *S. canis*, *S. bovis*, *S. equinus*, *S. anginosus*, *S. sanguis*, *S. salivarius*, *S. mitis*; *Listeria monocytogenes*, *Nocardia asteroides*, *Bacteroides* species, *Actinomycetes* species, *Treponema pallidum*, *Leptospirosa* species, *Klebsiella pneumoniae*; *Proteus* sp., including *Proteus vulgaris*; *Serratia* species, *Acinetobacter*, *Yersinia* species, including *Y. pestis* and *Y. pseudotuberculosis*; *Francisella tularensis*, *Enterobacter* species, *Bacteroides* species, *Legionella* species, *Borrelia burgdorferi*, and the like.

In some embodiments, the MoMo30 protein is used for the treatment or prevention of a fungal infection. Exemplary fungi for treatment include, but are not limited to, *Aspergillus* species, Dermatophytes, *Blastomyces derinatitidis*, *Candida* species, including *C. albicans* and *C. krusei*; *Malassezia furfur*, *Exophiala werneckii*, *Piedraia hortai*, *Trichosporon beigelii*, *Pseudallescheria boydii*, *Madurella grisea*, *Histoplasma capsulatum*, *Sporothrix schenckii*, *Histoplasma capsulatum*, *Tinea* species, including *T. versicolor*, *T. pedis*, *T. unguium*, *T. cruris*, *T. capitus*, *T. corporis*, *T. barbae*; *Trichophyton* species, including *T. rubrum*, *T. interdigitale*, *T. tonsurans*, *T. violaceum*, *T. yaoundei*, *T. schoenleinii*, *T. megninii*, *T. soudanense*, *T. equinum*, *T. erinacei*, and *T. verrucosum*; *Microsporum* species, including *M. audouini*, *M. ferrugineum*, *M. canis*, *M. nanum*, *M. distortum*, *M. gypseum*, *M. fulvum*, and the like.

In certain embodiments, the MoMo30 protein may be useful for preventing or treating a variety of conditions including, for example, infections of the skin, infections of the urogenital tract, infections of the digestive system (e.g., the gut), infections of the lung, and/or infections of the sinus. For example, the antimicrobial compositions may be useful for the treatment of a condition, such as, for example, rosacea, atopic dermatitis (e.g., eczema), a Candida infection (e.g., vaginal, diaper, intertrigo, balanitis, oral thrush), *Tinea versicolor*, Dermatophytosis (e.g., *Tinea pedis* (athlete's foot)), *Tinea unguium*, Onychomycosis (e.g., toe nail fungus), *Tinea cruris*, *Tinea capitus*, *Tinea corporis*, *Tinea barbae*, seborrheic dermatitis, antibiotic-resistant skin infections, impetigo, ecthyma, erythrasma, burn wounds (e.g., reduction of infections, improved healing), diabetic foot/leg ulcers (e.g., reduction of infections, improved healing), prevention of central catheter-related blood stream infections, oral mucositis, warts (e.g., common, flat, plantar, genital), and molluscum contagiosum. In some embodiments, the condition is acne, often acne vulgaris and sometimes acne conglobate.

In some embodiments, the MoMo30 protein may be useful for treating or preventing a protozoan infection. Exemplary protozoan infections include, but are not limited to those caused by *Cryptosporidium*, *Isospora belli*, *Toxoplasma gondii*, *Trichomonas vaginalis*, and *Cyclospora* species.

Administration of Nutraceutical Composition

The nutraceutical ingredients of the present application are generally introduced with one or more nutraceutically acceptable carriers. A "nutraceutically acceptable carrier" is intended to include any and all solvents, solubilizers, fillers, stabilizers, binders, absorbents, bases, buffering agents, lubricants, controlled release, vehicles, diluents, emulsifying agents, humectants, lubricants, dispersion media, coatings, antibacterial or antifungal agents, isotonic and absorption delaying agents, and the like, compatible with nutraceutical administration. The use of such media and agents for nutraceutically active substances is well-known in the art. Except as far as any conventional media or agent is incompatible with the active compound, use thereof in the compositions is contemplated. Supplementary agents can also be incorporated into the compositions. In certain embodiments, the nutraceutically acceptable carrier comprises serum albumin.

In preferred embodiments, the nutraceutical composition is orally administered. Oral compositions generally include an inert diluent or an edible carrier. They can be enclosed in gelatin capsules or compressed into tablets. For oral therapeutic administration, the active compound may be incorporated with excipients and used in the form of tablets, troches, or capsules. Nutraceutically compatible binding agents, and/or adjuvant materials can be included as part of the composition. The tablets, pills, capsules, lozenges, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the nutraceutical ingredients may be delivered in the form of an aerosol spray from pressured container or dispenser which contains a suitable propellant, e.g., a gas such as carbon dioxide, or a nebulizer.

In some embodiments, local administration of the nutraceutical compositions of the present application may be carried out by topical administration.

Systemic administration can also be administered by transmucosal and transdermal administration. Penetrants appropriate to the barrier to be permeated may be used in such formulations. Such penetrants are known in the art, and include, for example, for detergents, bile salts, and fusidic acid derivatives. In some embodiments, transmucosal administration is accomplished using nasal sprays or suppositories. For transdermal administration, the nutraceutical compositions may be formulated into ointments, salves, gels, or creams as generally known in the art.

In certain embodiments, the nutraceutical composition is formulated for sustained or controlled release of the active ingredients. Biodegradable, biocompatible polymers can be used, such as ethylene vinyl acetate, polyanhydrides, polyglycolic acid, collagen, polyorthoesters, and poly lactic acid. Methods for preparation of such formulations are well known to those skilled in the art. The materials can also be obtained commercially from e.g., Alza Corporation and Nova Pharmaceuticals, Inc. Liposomal suspensions (including liposomes targeted to infected cells with monoclonal antibodies to viral antigens) can also be used as nutraceutically acceptable carriers.

It is especially advantageous to formulate the nutraceutical composition in dosage unit form for ease of administration and uniformity of dosage. Suitable unit dosage forms include, but are not limited to powders, tablets, pills, capsules, liquids, teas, lozenges, suppositories, patches, nasal sprays, lipid complexes, etc.

A dosage unit form as used herein includes physically discrete units suited as unitary dosages for the subject; each unit containing a predetermined quantity of nutraceutical ingredients determined to produce the desired therapeutic effect in association with the any nutraceutically acceptable carrier(s). The specific dosage unit forms of the present application may be dictated by or directly dependent on the unique characteristics of the nutraceutical ingredients and the particular effects to be achieved, and the limitations inherent in the art of compounding such an active compound for the treatment of individuals. The nutraceutical composition according to the present application may be administered orally, sublingually, topically or transmucosally.

As a general proposition, the nutraceutical ingredient(s) are administered or formulated for administration, in a weight range of about 1 ng/kg body weight/day to about 100 mg/kg body weight/day whether by one or more administrations. In more particular embodiments, the nutraceutical ingredient(s) are administered or formulated for administration, in a weight range from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, the nutraceutical ingredient(s) are administered or formulated for administration, individually or collectively, at a dosage range of 1 ng-10 ng per dose, 10 ng-100 ng per dose, 100 ng-1 µg per dose, 1 µg-10 µg per dose, 10 µg-100 µg per dose, 100 µg-1 mg per dose, 1 mg-10 mg per dose, 10 mg-100 mg per dose, and 100 mg-1000 mg per dose. The MoMo30 protein or MoMo30-containing formulation may be injected once daily, twice daily, three times daily, and/or every 2, 3, 4, 5, 6 or 7 days. In addition, the MoMo30 protein or MoMo30-containing formulation may be administered over a period of one month, two months, six months, 12 months, 2 years, 5 years, 10 years, 20 years, or more.

In other embodiments, the nutraceutical ingredient(s) are administered, individually or collectively, in a range from about 1 ng/kg to about 100 mg/kg. In more particular embodiments, the nutraceutical ingredient(s) are administered or formulated for administration, individually or collectively, in a dosage range from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the nutraceutical ingredient(s) may be administered or formulated for administration, individually or collectively, in a dose of 0.0006, 0.001, 0.003, 0.006, 0.01, 0.03, 0.06, 0.1, 0.3, 0.6, 1, 3, 6, 10, 30, 60, 100, 300, 600 or 1000 mg/day.

For prophylactic or therapeutic use, the nutraceutical composition may be administered once, twice, three times or four times per day with the doses given at equal intervals throughout the day and night to maintain a constant presence of the drug to provide sufficient antimicrobial activity.

In some embodiments, the treatment may be carried out for as long a period as necessary, i.e., until the infection is cleared or no longer a threat to the host. In some cases, the treatment may be continued indefinitely while the disease state persists, although discontinuation might be indicated if the antimicrobial compositions no longer produce a beneficial effect. For example, in some instances the treatment may be carried out for 1 month, 2 months, 4 months or 6 months and then discontinued.

II. Treatment of Plants with the Hevamine A-Related Composition

In another aspect, the present application provides a hevamine A-related composition for plant disease control, prevention or treatment. As used herein, the term "plant" includes whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same.

In one embodiment, plant disease control, prevention or treatment is accomplished by applying an effective amount of the hevamine A-related composition either pre- or post-infection, to the whole plant or a portion of the plant such as the roots, stems, foliage, fruit, seeds, tubers or bulbs, or to the media (e.g., soil, sand or water) in which the plants to be protected are growing. In one aspect, the hevamine A-related protein is translocated through the vascular system in plants and therefore the entire plant is not required to be contacted. Thus, in one aspect a portion of a plant may be treated with a hevamine A-related composition so that a plant disease is prevented, treated, or controlled in the treated portion, as well as in untreated portions of the plant, such as untreated leaves, stems, or roots.

In one embodiment, untreated leaves of wheat plants have decreased disease infection when lower leaves are treated with hevamine A-related composition. In another embodiment, disease control, prevention or treatment corresponds to the concentration of MoMo30 protein in the tissue of the untreated leaf. In another embodiment, the hevamine A-related composition is be applied to the seed to protect the seed and seedling.

In one embodiment, a plant or plant part is contacted with the hevamine A-related composition either directly on a crop plant, or immediately adjacent to the crop plant where the MoMo30 protein can be taken-up into the crop plant's vascular system. In methods where the composition is directly contacted with the crop plant, the composition may be contacted with the entire crop plant or with only a portion of the plant. Additionally, a plant pathogen may be contacted with the hevamine A-related composition by e.g., direct contact on a plant surface. In a preferred aspect, a plant is contacted with the hevamine A-related composition by overhead spraying of the composition. Exemplary plant parts include leaves, roots, stems, fruit, seeds, tubers, bulbs, seeds, pollen, ovules, flowers, pods, stems, shoots, and combinations thereof.

Application of the hevamine A-related composition to the foliage of plants is preferably accomplished by spraying, using any conventional means for spraying liquids, such as spray nozzles or spinning-disk atomizers. The hevamine A-related composition is preferably dilute enough to be readily sprayed using standard agricultural spray equipment. Suitable application rates for the present invention vary depending upon a number of factors, including e.g., the concentration of MoMo30 protein and the plant species involved. Useful rates for applying an aqueous composition to a field of foliage can range from about 25 to about 1,000 liters per hectare (1/ha), preferably about 50 to about 300 l/ha, by spray application.

Suitable carriers for MoMo30 treatment of plants or plant parts include water, aqueous solution, slurries, granules, or powders.

The plant treatment methods of the present invention find use in the control, prevention or treatment of a wide variety of plant pathogens. The treatment methods include prophylactic inhibition and therapeutic treatment of infection by plant pathogens. Preferably, the methods of the present invention inhibit or treat plant pathogenic *fungi*, bacteria and viruses, including any of those described herein.

Plant pathogens can be classified by their life cycle in relation to a plant host, these classifications include obligate parasites, facultative parasites, and facultative saprophytes. Obligate parasites can only survive and reproduce by obtaining nutrition from living plant cells and are in direct contact with these cells. Examples of obligate fungal parasites of plants include, but are not limited to members of Uredinales (rusts), Ustilaginales (smuts and bunts), Erysiphales (powdery mildews), and Oomycetes (water molds and downy mildews). Facultative parasites are organisms that generally survive as saprophytes on the products of other organisms or dead organisms but can become parasitic when the conditions are favorable. Facultative saprophytes are organisms that generally survive as parasites of plants but can survive as saprophytes when a susceptible plant host is not available.

In particular embodiments, the hevamine A-related compositions for disease control is applied to the crop plant at a later growth stage, for example, when the plant is flowering or in the process of producing seeds or fruit, it is at these stages of development that plant diseases can have the greatest effect on crop yield. Leaves are the source tissues that provide the products of photosynthesis needed for plant growth, seed, fruit and storage organ development. Protecting these leaves from disease due to fungal infection is important to protect yield of the crop. The flag leaf of monocot crops contributes substantially to the yield of the crop, protecting this leaf from disease is particularly important in protecting monocot crop yield. Leaves of dicot crops generally provide the products of photosynthesis to the closely associated fruiting structures of the plant, protecting these leaves from disease is particularly important in protecting dicot crop yields. Roots provide water and mineral nutrients to the plants, protecting roots from disease is also particularly important in maintaining yield of the crop plant.

Enhanced formulations for systemic (includes both locally systemic and whole plant systemic) uptake may include the addition of adjuvants, for example, alkoxylated fatty amines, organosilicones, nonyl phenol ethylene oxide condensate, and others known in the art. Examples of suitable adjuvants that enhance the uptake and efficacy of glyphosate include polyoxyalkylene alkylamines, polyoxyalkylene alkylammonium salts, polyoxyalkylene alkylamine oxides, polyoxyalkylene tertiary and quaternary etheramines, polyoxyalkylene etheramine oxides, mono- and di-(polyoxyalkylene alcohol) phosphates, polyoxyalkylene alkylethers and combinations thereof. Preferred adjuvants are polyoxyethylene coco and tallow amines, polyoxyethylene C8-18 alkyl oxypropyl amines, polyoxyethylene C16-22 alkylethers and combinations thereof. Examples of these adjuvants can be found in U.S. Pat. Nos. 5,668,085, 5,683, 958, 5,703,015, 6,063,733, 6,121, 199, 6,121,200, 6,184, 182, 6,245,713, 6,365,551, RE37,866 and U.S. Patent Application Pub. No. US2003/0104943 A1 (all of which are herein incorporated by reference in their entirety).

In some embodiments, the hevamine A-related composition is applied to a crop plant. In certain embodiments, the crop plant is a food crop for human consumption, such as a fruit, vegetable, grain or tuber, such as potatoes.

In other embodiments, the crop plant is a feed crop for producing e.g., cereal grains (e.g., oats), corn, alfalfa, barley, and various kinds of grasses and hay.

In other embodiments, the crop plant is a fiber crop, such as cotton, flax, hemp, and bamboo.

In other embodiments, the crop plant is an oil crop for producing e.g., corn, sunflower, canola, safflower, and olive oils.

In other embodiments, the crop plant is an ornamental crop, such as shade trees, flowering trees, shrubs, flowers, and grasses.

In other embodiments, the crop plant is an industrial crop, such as a Hevea tree for producing rubber.

Exemplary plants that can be used for prophylaxis or treatment with MoMo30 compositions include the class of higher and lower plants, including angiosperms (monocotyledonous and dicotyledonous plants), gymnosperms, ferns, horsetails, psilophytes, lycophytes, bryophytes, and multicellular algae. Preferably, plants for use in the methods of the present invention include any vascular plant, for example monocotyledons or dicotyledons or gymnosperms, including, but not limited to alfalfa, apple, Arabidopsis, banana, barley, canola, castor bean, *Chrysanthemum*, clover, cocoa, coffee, cotton, cottonseed, corn, crambe, cranberry, cucumber, dendrobium, dioscorea, eucalyptus, fescue, flax, gladiolus, liliacea, linseed, millet, muskmelon, mustard, oat, oil palm, oilseed rape, papaya, peanut, pineapple, ornamental plants, Phaseolus, potato, rapeseed, rice, rye, ryegrass, safflower, sesame, sorghum, soybean, sugarbeet, sugarcane, sunflower, strawberry, tobacco, tomato, turfgrass, wheat and vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, crambe, flax, linseed, mustard, oil palm, oilseed rape, peanut, potato, rice, safflower, sesame, soybean, sugarbeet, sunflower, tobacco, tomato, and wheat preferred. More preferably, plants for use in the methods of the present invention include any crop plant, for example, forage crop, oilseed crop, grain crop, fruit crop, vegetable crop, fiber crop, spice crop, nut crop, turf crop, sugar crop, beverage crop, and forest crop. In a highly preferred aspect, the crop plant used in a method is a soybean plant. In another highly preferred aspect, the crop plant is wheat. In another highly preferred aspect, the crop plant is corn. In another highly preferred aspect, the crop plant is cotton. In another highly preferred aspect, the crop plant is alfalfa. In another highly preferred aspect, the crop plant is sugarbeet. In another highly preferred aspect, the crop plant is rice. In another highly preferred aspect, the crop plant is potato. In another highly preferred aspect, the crop plant is tomato.

In some embodiments, the prevention and reduction of pathogen infections or related disease symptoms are reduced at least about 10% from a plant untreated by the hevamine A-related composition. Preferably, the infection, symptoms or both are prevented or reduced at least about 20%, 30%, 40%, 50%, 60%, 70%, 80% compared to infection, symptoms or both on a plant not treated with a MoMo30 composition. A disease infection may be measured by any reproducible means of measurement. In one aspect, infection may be measured by counting lesions or pustules visible to the naked eye, or at a specified magnification. In a preferred aspect, the specified magnification is 2×, 3×, 4×, 5×, 10×, or 50×.

In some embodiments, methods of preventing disease in a plant are provided where only a portion of the plant is contacted with the hevamine A-related composition, yet untreated portions of the plant are also protected from disease. In one aspect, only about 5%, 10%, 20%, 30%, 50%, 75% or 90% of the plant is contacted with the hevamine A-related composition. The percentage of plant contacted by the hevamine A-related composition may be measured by any reproducible means of measurement.

In some embodiments, the plant pathogen is a fungus. The method of the present invention can be used to control, prevent or treat infection from a wide array of plant pathogens that include obligate parasites, facultative parasites, and facultative saprophytes, which include, but are not limited to the following: Ascomycete *fungi* such as of the genera *Venturia, Podosphaera, Erysiphe, Monolinia, Mycosphaerella*, and *Uncinula*; Basidiomycete *fungi* such as from the genera *Hemileia, Rhizoctonia*, and *Puccinia; fungi imperfecti* such as the genera *Botrytis, Helminthosporium, Rhynchosporium, Fusarium* (i.e., *F. monoliforme*), *Septoria, Cercospora, Alternaria, Pyricularia*, and *Pseudocercosporella* (i.e., *P. herpotrichoides*); Oomycete *fungi* such as from the genera *Phytophthora* (i.e., *P. parasitica. P. medicaginis, P. megasperma*), *Peronospora* (i.e, *P. tabacina*), *Bremia, Pythium*, and *Plasmopara*; as well as other *fungi* such as *Sclerophthora macrospora, Sclerophthora rayissiae, Sclerospora graminicola, Peronosclerospora sorghi, Peronosclerospora philippinensis, Peronosclerospora sacchari* and *Peronosclerospora maydis, Physopella zeae, Cercospora zeaemaydis, Colletotrichum graminicola, Gibberella zeae, Exserohilum turcicum, Kabatiellu zeae*, and *Bipolaris maydis*.

Exemplary fungal pathogens include e.g., genera *Alternaria* (e.g., *A. solani*); *Fusarium* (e.g., *F. culmorum, F. graminearum, F. culmorum, F. graminearum, F. oxysporum, F. roseum*); *Microdochium* (e.g. *M. nivale*); *Magnaporthe; Monilia* (e.g. *M. fructigenae, M. laxa*); *Aspergillus* (e.g., *A. paraciticus*); *Penicillium; Aspergillus; Austropuccinia; Hemileia* (e.g., *H. vastatrix*); *Botrytis* (e.g. *B. cinerea, B. fabae, B. ricini, B. elliptica*); *Cronartium; Eutypa; Phaeomoniella; Phaeoacremonium; Phomopsis; Cercospora; Mycosphaerella; Bipolaris; Sclerotinia; Pythium* (e.g., *P. aphanidermatum, P. irregulare, P. ultimum*); *Phytophthora* (e.g. *P. infestans, P. fragariae, P. cactorum, P. sojae, P. cinnamomi, P. citricola, P. citrophthora, P. cryptogea, P. drecshsleri, P. infestans, P. nicotianae*); *Rhizoctonia* (e.g. *R. solani, R. cerealis*); *Puccinia* (rusts; e.g., *P. striiformis, P. graminis tritici, P. recondite, P. hordei, P. triticina, P. triticiduri*); *Leveillula; Microsphaera* (e.g. *M. vaccinia*); *Podosphaera; Odium; Sphaerotheca; Peronospora; Cercospora; Erysiphe; Uncinula; Phomopsis* (e.g. *P. viticola, P. rachis, P. vaccinii*); *Monilinia* (e.g. *M. vaciniicormbosi, M. fructicola*); *Phragmidium* (e.g. yellow rust); *Drepanopeziza* sp. (e.g. anthracnose); *Erysiphe* (e.g., *E. graminis*); *Kuehneola* (e.g. cane and leaf rust); *Sphaerulina* (e.g. orange rust); *Arthuriomyces* (e.g. powdery mildew); *Mycosphaerella* sp. (leaf spot; e.g. *M. pinodes, M. graminicola*); *Dendrophoma* (e.g., *D. obscurans*); *Diplocarpon* (e.g., *D. earliana*); *Godronia* (e.g., *G. cassandrac*); *Exobasidium* (e.g., *E. vaccinii*); *Gymnosporangium* (e.g., apple rust); *Leucostoma* (e.g., *L. cincta* or *L. persoonii*); *Apiosporina* (e.g.,

*A. morbosa*); *Melampsora* (e.g., *M. lini*); *Sclerotium* (e.g., *S. rolfsii*); *Septoria* sp. (e.g., *S. tritici, S. nodorum, S. passerinii*); *Phaeosphaeria* (e.g., *P. nodorum*); *Tapesia* (e.g., *T. yallundae, T. acuiformis*); *Thielaviopsus* (e.g., *T. basicola*); *Gaeumannomyces* (e.g., *G. graminis*); *Erysiphe* (e.g., *E. graminis, E. cichoracearum, E. beticola*); *Drechslera* (e.g., *D. triticirepentis*); *Phakopsora* (e.g., *Phakopsora pachyrhizi, Phakopsora meibomiae, Phakopsora euvitis*); *Pyrenophora* (e.g., *P. teres*); *Cochliobolus* (e.g., *C. sativus anamorphe: Bipolaris sorokiniana*); *Rhynchosporium* (e.g., *R. secalis*); *Ascochyta* (e.g., *A. pisi*); *Peronospora* (e.g., *P. pisi, P. manchurica*); *Rhizopus; Trichoderma; Magnaporthe* (e.g., *M. grisea, M. oryzae*); *Sphaerotheca* (e.g., *S. fuliginea* and *S. macularis*); *Leveillula* (e.g., *L. taurica*); *Cladosporium; Colletotrichum* (e.g., *C. acutatum*); *Venturia* (*V. inaequalis*); *Podosphaera* (e.g., *P. leucotricha*); *Uncinula* (e.g., *U. necator*); *Guignardia* (e.g., *G. bidwellii*); *Plasmopara* (e.g., *P. viticola*); *Ramularia* (e.g., *R. beticola*); *Cercospora* (e.g., *C. beticola*); *Stagonospora* (e.g., *S. nodorum*); *Ustilago* (e.g., *U. maydis*); *Uromyces; Verticillium; Drechslera teres* f. *maculate; Ramularia collo cygni; Ophiocladium horde*; and *Blumeria graminis*.

Particularly preferred pathogens include, but are not limited to: *Puccinia, Rhizoctonia*, GGT, stripe rust, Asian soybean rust (*Phakopsora pachyrhizi*), *Fusarium* species, *Verticillium* species, gray leaf spot, *Phytophthora* species and corn rust.

Diseases controlled, prevented or treated with the MoMo30 compositions of the present application include, for example, diseases of alfalfa plants such as root rot (*Phytophora medicaginis, P. megasperma*); rice plant such as rice blast (*Pyricularia oryzae*), *Helminthosporium* leaf blight (*Helminthosporium oryzae, Cochliobolus miyabeanus*), Bakanae disease (*Gibberella fujikuroi*), seedling blight (*Rhizopus oryzae*), sheath blight (*Rhizoctonia solani*), and so on, those of oat such as crown rust (*Puccinia coronata*), and so on, those of barley such as powdery mildew (*Erysiphe graminis*), scald (*Rhynchsporium secalis*), spot-blotch (*Cochliobolus sativus*), yellow mottleaf (*Helminthosporium gramineum, Pyrenophora gramineum*), net blotch (*Pyrenophra teres*), stinking smut (*Tilletia caries*), loose smut ((*Istilago nuda*), and so on, those of wheat such as powdery mildew (*Erysiphe graminis*), glume-blotch (*Leptosphaeria nodorum, Septoria nodorum*), stripe rust (*Puccinia striiformis*), *Typhula* snow blight (*Typhula incarnata*), eye spot (*Pseudocercosporella herpotrichoides*), snow mold ((*Calonectria graminicola, Fusarium nivale*), stem rust (*Puccinia graminis*), black snow blight (*Typhula ishikariensis*), scab (*Gibberella zeae*), leaf rust (*Puccinia recondita, Puccinia triticina*), stripe (*Helminthosporium gramineum*), stinking smut (*Tilletia caries*), speckled leaf blight (*Septoria tritici*), loose smut ((*Istilago tritici*), and so on, those of corn such as damping-off (*Pythium debaryanum*), and so on, those of rye such as purple snow mold (*Fusarium nivale*), and so on, those of potato such as late blight (*Phytophthora infestans*), and so on, those of tobacco plant such as downy mildew (*Peronospora tabacina*), foot rot (*Phytophthora parasitica* var), *Septoria* blight (*Cercospora nicotianae*), and so on, those of sugar beet such as leaf spot (*Cercospora beticola*), damping-off (*Pythium debaryanum, Rhizoctonia solani, Pythium aphanidermatum*), and so on, those of paprika such as gray mold (*Botrytis cinerea*), and so on, those of kidney bean such as gray mold (*Botrytis cinerea*), *Sclerotinia* seed rot (sclerotial rot) (*Sclerotinia sclerotiorum*), southern blight (*Corticium rolfsii*), and so on, those of broad bean such as powdery mildew (*Erysiphe polygoni, Sphaerotheca fuliginea*), rust (*Uromyces fabae, Uromyces phaseoli*), gray mold (*Botrytis cinerea*), and so on, those of peanut such as *Ascochyta* spot (*Mycosphaerella arachidicola*), and so on, those of cabbage such as damping blight (*Rhizoctonia solani*), and so on, those of cucumber such as powdery mildew (*Sphaerotheca fuliginea*), stem rot (*Fusarium oxysporum*), gummy stem blight (*Mycosphaerella melonis*), downy mildew (*Pseudoperonospora cubensis*), gray mold (*Botrytis cinerea*), sclerotial seed rot (*Sclerotinia sclerotiorum*), anthracnose (*Colletotrichum lagenarium*), damping blight (*Fusarium oxysporum, Pythium aphanidermatum, Rhizoctonia solani*), and so on, those of KOMATSUNA such as *Alternaria* sooty spot (*Alternaria brassicicola*), club root (Plasmodiophora brassicae), and so on, those of celery such as speckled leaf blotch (*Septoria apii*), and soon, those of radish such as yellows (*Fusarium oxysporum*), and so on, those of tomato such as *Fusarium* wilt (*Fusarium oxysporum*), foot rot (*Phytophthora infestans*), ring leaf-spot (*Alternaria solani*), gray mold (*Botrytis cinerea*), leaf blight (*Phytophthora capsici*), black rot (*Alternaria* tomato), and so on, those of eggplant such as brown rot (*Phytophthora capsici*), vascular wilt pathogens, e.g. *Verticillium* wilt (*Verticillium alboatrum. V. dahliae*), and so on, those of Chinese cabbage such as black rot (*Alternaria japonica*), club root (Plasmodiophora brassicae), and so on, those of sweet pepper such as foot rot (*Phytophthora capsici*), gray mold (*Botrytis cinerea*), and so on, those of lettuce such as gray mold (*Botrytis cinerea*), and so on, those of *Citrus* fruits such as pod and stem blight (*Diaporthe citri*), and so on, those of pear such as scab (*Venturia nashicola*), black rot (*Alternaria kikuchiana*), brown-spot (*Gymnosporangium haraeanum*), and so on, those of grape such as downy mildew (*Plasmopara viticola*), gray mold (*Botrytis cinerea*), *Sphaceloma* scab (*Elsinoe ampelina*), and so on, those of peach such as leaf curl (*Taphrina deformans*), shot hole (*Mycosphaerella cerasella*), and so on, those of apple such as powdery mildew (*Podosphaera leucotria*), scab (*Cladsporium carpophilum*), gray mold (*Botrytis cinerea*), black rot (*Venturia inaegualis*), brown spot (*Gymnosporangium yamadae*), white root rot (*Rosellinia nectrix*), *Alternaria* leaf spot (*Alternaria mali*), and so on, and other diseases of grains, fruits and vegetables such as oil-seed rape, sunflower, carrot, pepper, strawberry, melon, kiwi fruit, onion, leek, sweet potato, fig, ume, *Asparagus*, persimmon, soybean, adzukibean, watermelon, crown daisy, spinach, tea and so on. Additional fungal pathogens and plant diseases are described in U.S. Pat. No. 10,329,580, which is expressly incorporated herein by reference in its entirety.

In some embodiments, the plant pathogen is a bacterium. Bacteria can cause a number of diseases on ornamental and agronomic crops. These include leaf spotting on English ivy, fireblight on apples and pears, crown gall on stone fruits, and wilts in geraniums and cucurbits (cucumbers, squash and melons). Common plant pathogenic bacteria include, but are not limited to *Erwinia* spp., *Dickeya* spp., *Pseudomonas* spp., *Xanthomonas* spp., and *Clavibacter* spp. These pathogens may attack plant root systems, foliage, or a combination of both.

Exemplary *Erwinia* species include, but are not limited to *E. amylovora, E. aphidicola, E. billingiae, E. mallotivora E. papayae, E. persicina, E. psidii, E. pyrifoliae, E. rhapontici, E. stewartia, E. toletana*, and *E. tracheiphila*. Exemplary *Dickeya* species include, but are not limited to *D. chrysanthemi, D. dadantii, D. solani*. Exemplary *Pseudomonas* species include, but are not limited to *P. amygdale, P. avellanae, P. caricapapayae, P. cichorii, P. coronafaciens, P. ficuserectae, P. helianthi, P. meliae, P. savastanoi, P. syrin-* gae, *P. tabaci, P. tomato, P. viridiflava*. Exemplary *Xanthomonas* species include, but are not limited to pathovars of *X. albilineans, X. alfalfae, X. ampelina, X. arboricola, X. axonopodis, X. boreopolis, X. badrii, X. bromi, X. campestris, X. cassayae, X. citri, X. codiaei, X. cucurbitae, X. cyanopsidis, X. cynarae, X. euvesicatoria, X. fragariae, X. gardneri, X. holcicola, X. hortorum, X. hyacinthi, X. malvacearum, X. maltophilia, X. manihotis, X. melonis, X. oryzae, X. papavericola, X. perforans, X. phaseoli, X. pisi, X. populi, X. sacchari, X. theicola, X. translucens, X. vasicola, X. vesicatoria*. Exemplary *Clavibacter* species include, but are not limited to *Clavibacter michiganensis* and *Clavibacter michiganensis* subsp. *insidiosus*.

Additional bacterial pathogens include *mycoplasma* and *mycoplasma*-like (phytoplasma) bacteria, such as Xylella fastidiosa, which causes Pierce's disease and Phony Peach diseases, several Phytoplasma causing Aster Yellows disease, Peach X disease, and Peach Yellow disease; *S. kunkelii*, causing corn stunt disease), as well as various rickettsia and rickettsia-like bacteria.

In some embodiments, the plant pathogen is a plant virus. In some cases, the plant virus is Tobacco mosaic virus, Tomato spotted wilt virus, Tomato yellow leaf curl virus, Cucumber mosaic virus, Potato virus Y, Cauliflower mosaic virus, African cassava mosaic virus, Plum pox virus, Brome mosaic virus, Potato virus X, *Citrus tristeza* virus, Barley yellow dwarf virus, Alfalfa dwarf virus Potato leafroll virus, or Tomato bushy stunt virus.

III. Genetically Modified Plants

In another aspect, the present application provides a transgenic plant expressing the MoMo30 protein of the present application. In one embodiment, the present disclosure relates to a transgenic plant, plant part, or plant cell, wherein the transgene comprises a polynucleotide encoding an amino acid sequence at least 95% identical to SEQ ID NO: 4 and exhibits resistance or tolerance to a plant pathogen.

As used herein, the term "transgenic plant" refers to a plant that contains genetic material not found (i.e. "exogenous") in a wild-type plant of the same species, variety or cultivar. In accordance with the present application, the genetic material comprises a MoMo30 expression cassette introduced into the plant by human manipulation. The transgenic plant may additionally contain sequences which are native to the plant being transformed, but wherein the "exogenous" gene has been altered in order to alter the level or pattern of expression of the gene, for example, by use of one or more heterologous regulatory elements and the like.

As further described below, the expression cassette typically comprises a polypeptide-encoding sequence operably linked (i.e., under regulatory control of) to appropriate inducible or constitutive regulatory sequences that allow for the expression of the polypeptide. The expression cassette can be introduced into a plant by transformation or by breeding after transformation of a parent plant.

The plant or plant part for use in the present invention include plants of any stage of plant development. Exemplary plant parts include leaves, roots, stems, fruit, seeds, tubers, bulbs, seeds, pollen, ovules, flowers, pods, stems, shoots, and combinations thereof. Preferably, the application occurs during the stages of germination, seedling growth, vegetative growth, and reproductive growth. More preferably, applications of the present invention occur during vegetative and reproductive growth stages. The stages of vegetative and reproductive growth are also referred to herein as "adult" or "mature" plants.

Methods of producing transgenic plants or transgenic plant cells are well known to those of ordinary skill in the art. A transgenic plant cell or transgenic plant is obtained by either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant. As used herein, the term "R0 transgenic plant" refers to a plant that has been genetically transformed or has been regenerated from a plant cell or cells that have been genetically transformed.

Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369, 8,937,214, 10,329,580, and U.S. Patent Publication No. 2022/0135997; each of which is expressly incorporated herein by reference in their entirety.

In one aspect, the present application provides a transgenic plant, transgenic plant part, or transgenic plant cell, comprising: a stably integrated DNA expression construct comprising a polynucleotide comprising a polynucleotide containing a nucleotide sequence at least 95% identical to SEQ ID NO: 1 or SEQ ID NO: 2, or a polynucleotide encoding a protein comprising an amino acid sequence at least 95% identical to SEQ ID NO: 3 or SEQ ID NO: 4, wherein the transgenic plant exhibits increased resistance to at least one bacterial, fungal, or viral infection as compared to a control plant lacking the recombinant DNA expression construct under the same condition.

The MoMo30 transgene may be introduced in any plant susceptible to a plant pathogen, including any of the plants described above. In certain preferred embodiments, the transgenic plant is a crop plant. Exemplary crop plants include, but are not limited to wheat, corn, rice, barley, cotton, canola, alfalfa, sugarbeet, potato and tomato.

The MoMo30 transgene may be introduced in any plant susceptible to a plant pathogen, including any of the plants described above. In certain preferred embodiments, the transgenic plant is a crop plant. Exemplary crop plants include, but are not limited to a forage crop, oilseed crop, grain crop, fruit crop, vegetable crop, fiber crop, spice crop, nut crop, turf crop, sugar crop, beverage crop, and forest crop. In certain preferred embodiments, crop plant is wheat, corn, rice, barley, cotton, canola, alfalfa, sugarbeet, potato and tomato.

Preferred components likely to be included with vectors used in the present application are as follows.

i. Regulatory Elements

Exemplary promoters for expression of a transgene include plant promoters, such as the Cauliflower Mosaic Virus (CaMV) 35S promoter, or other promoters, such as CaMV 19S, nopaline synthase (Nos), alcohol dehydrogenase (Adh), sucrose synthase, α-tubulin, actin, chlorophyll a/b-binding protein (Cab), phosphoenolpyruvate carboxylase (PEPCKase) or those associated with the R gene complex. Tissue specific promoters such as root cell promoters and tissue specific enhancers are also contemplated to be particularly useful, as are inducible promoters such as ABA- and turgor-inducible promoters. In certain aspects, a promoter for use according to the application is an ePCISV, TubA, eFMV, FMV, e35S, 35S or Ract1 promoter.

In certain aspects, transformation events comprised in transgenic plants according to the application comprise a plurality of promoter sequences. In certain aspects, a promoter sequence is repeated no more than about 2, 3, 4, or 5 times in a single transformation event. In other embodiments, identical or highly homologous promoter sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different promoter sequences.

In further embodiments, identical or highly homologous promoter sequences are linked to transgenes that confer similar traits (e.g., transgenes that confer insect resistance). In certain aspects, two or more identical or highly homologous promoter sequences are separated by at least 1, 2 or 3 expression cassettes within a single transformation event. In other embodiments, identical or highly homologous promoter sequences are linked to two or more contiguous expression cassettes in a single transformation event.

The DNA sequence between the transcription initiation site and the start of the coding sequence, i.e., the untranslated leader sequence, can also influence gene expression. One may thus wish to employ a particular leader sequence with a transformation construct of the application. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

In another aspect, the present application provides a method for producing foregoing transgenic plant, comprising the steps of: (a) stably transforming a host plant or plant cell with a polynucleotide comprising a polynucleotide containing a nucleotide sequence at least 95% identical to SEQ ID NO: 1 or SEQ ID NO: 2, or a polynucleotide encoding a protein comprising an amino acid sequence at least 95% identical to SEQ ID NO: 3 or SEQ ID NO: 4; and (b) producing the transgenic plant or plant cell, where the transgenic plant or transgenic plant cell is identified that expresses the expression construct in an amount sufficient to provide increased resistance to at least one bacterial or fungal infection as compared to a control plant lacking the recombinant DNA expression construct under the same condition.

A. Plant Transformation and Transgene Expression Constructs

Certain embodiments of the present application relate to the construction and use of plant transformation constructs. Generally, the MoMo30 coding sequences are provided operably linked to a promoter (e.g., a heterologous promoter). Expression constructs are also provided comprising these sequences, as are plants and plant cells transformed with the sequences.

The construction of vectors which may be employed in conjunction with plant transformation techniques using these or other sequences according to the application will be known to those of skill of the art in light of the present disclosure. The techniques of the present application are thus not limited to any particular nucleic acid sequences.

Particularly useful for transformation are expression cassettes which have been isolated from such vectors. DNA segments used for transforming plant cells will, of course, generally comprise the RNA coding sequence, cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present application also encompasses transgenic plants incorporating non-expressed transgenes. Preferred components likely to be included with vectors used in the present application are as follows.

i. Regulatory Elements

Exemplary promoters for expression of a transgene include plant promoters, such as the Cauliflower Mosaic Virus (CaMV) 35S promoter, or other promoters, such as CaMV 19S, nopaline synthase (Nos), alcohol dehydrogenase (Adh), sucrose synthase, α-tubulin, actin, chlorophyll a/b-binding protein (Cab), phosphoenolpyruvate carboxylase (PEPCKase) or those associated with the R gene complex. Tissue specific promoters such as root cell promoters and tissue specific enhancers are also contemplated to be particularly useful, as are inducible promoters such as ABA- and turgor-inducible promoters. In certain aspects, a promoter for use according to the application is an ePCISV, TubA, eFMV, FMV, e35S, 35S or Ract1 promoter.

In certain aspects, transformation events comprised in transgenic plants according to the application comprise a plurality of promoter sequences. In certain aspects, a promoter sequence is repeated no more than about 2, 3, 4, or 5 times in a single transformation event. In other embodiments, identical or highly homologous promoter sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different promoter sequences.

In further embodiments, identical or highly homologous promoter sequences are linked to transgenes that confer similar traits (e.g., transgenes that confer insect resistance). In certain aspects, two or more identical or highly homologous promoter sequences are separated by at least 1, 2 or 3 expression cassettes within a single transformation event. In other embodiments, identical or highly homologous promoter sequences are linked to two or more contiguous expression cassettes in a single transformation event.

The DNA sequence between the transcription initiation site and the start of the coding sequence, i.e., the untranslated leader sequence, can also influence gene expression. One may thus wish to employ a particular leader sequence with a transformation construct of the application. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that transgene coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters that direct specific or enhanced expression in certain plant tissues are known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α-tubulin gene that also directs expression in roots.

ii. Terminators

Transformation constructs prepared in accordance with the application will typically include a 3' end DNA sequence that acts as a signal to terminate transcription and allow for the poly-adenylation of the mRNA produced by coding sequences operably linked to a transgene. Terminators which are deemed to be particularly useful in this context include those from the nopaline synthase gene of *Agrobacterium tumefaciens* (nos 3' end), the terminator for the T7 transcript from the octopine synthase gene of *Agrobacterium tumefaciens*, and the 3' end of the protease inhibitor I or II genes from potato or tomato. Regulatory elements such as an Adh intron, sucrose synthase intron or TMV omega element, may further be included where desired. In certain aspects, a terminator for use according to the application is a Hsp17, TubA, Ara5, 35S, nos or Tr7 terminator.

In certain aspects, transformation events comprised in transgenic plants according to the application comprise a plurality of terminator sequences. In certain aspects, a terminator sequence is repeated no more than about 2, 3, 4, or 5 times in a single transformation event. In other embodiments, identical or highly homologous terminator sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different terminator sequences. In further embodiments, identical or highly homologous terminator sequences are linked to transgenes that confer similar traits (e.g., transgenes that confer insect resistance). In certain aspects, two or more identical or highly homologous terminator sequences are separated by at least 1, 2 or 3 expression cassettes with a single transformation event. In other embodiments, identical or highly homologous terminator sequences are linked to two or more contiguous expression cassettes in a single transformation event.

iii. Intron Sequences

In certain aspects, intron sequences are included an expression cassette and may enhance transgene expression. In certain aspects, an intron for use according to the application is a Ract1, TubA, Sus1 or Hsp70 intron.

In certain aspects, transformation events comprised in transgenic plants according to the application comprise a plurality of intron sequences. In certain aspects, an intron sequence is repeated no more than about 2, 3, 4, or 5 times in a single transformation event. In other embodiments, identical or highly homologous intron sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different intron sequences. In further embodiments, identical or highly homologous intron sequences are linked to transgenes that confer similar traits (e.g., transgenes that confer insect resistance). In certain aspects, two or more identical or highly homologous intron sequences are separated by at least 1, 2 or 3 expression cassettes within a single transformation event. In other embodiments, identical or highly homologous intron sequences are linked to two or more contiguous expression cassettes in a single transformation event.

iv. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

v. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the application.

Included within the terms "selectable" or "screenable" markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present application including, but not limited to, neo, which provides kanamycin resistance and can be selected for using kanamycin, G418, paromomycin, etc.; bar, which confers bialaphos or phosphinothricin resistance; a mutant EPSP synthase protein conferring glyphosate resistance; a nitrilase such as bxn from *Klebsiella ozaenae* which confers resistance to bromoxynil; a mutant acetolactate synthase (ALS) which confers resistance to imidazolinone, sulfonylurea or other ALS inhibiting chemicals; a methotrexate resistant DHFR, a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues; a β-lactamase gene, which encodes an enzyme for which various chromogenic substrates are known (e.g., PADAC, a chromogenic cephalosporin); a xylE gene, which encodes a catechol dioxygenase that can convert chromogenic catechols; an α-amylase gene; a tyrosinase gene, which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a green fluorescent protein, a luciferase gene, which allows for bioluminescence detection; an aequorin gene, which may be employed in calcium-sensitive bioluminescence detection.

Another screenable marker contemplated for use in the present application is the firefly luciferase gene (lux), which allows for bioluminescence detection. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for population screening for bioluminescence, such as on tissue culture plates, or even for whole plant screening. The gene which encodes green fluorescent protein (GFP) is also contemplated as a particularly useful reporter gene. Expression of green fluorescent protein may be visualized in a cell or plant as fluorescence following illumination by particular wavelengths of light.

B. Tissue Cultures

Tissue cultures may be used in certain transformation techniques for the preparation of cells for transformation and for the regeneration of plants therefrom. As used herein, the term "regeneration" refers the process of growing a plant from a plant cell (e.g., plant protoplast, callus or explant). Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bacto™ agar (Difco-BD, Franklin Lakes, N.J.), Hazleton agar (Hazleton, Lenexa, Kans., USA), Gelrite® (Sigma, St. Louis, Mo.), PHYTAGEL (Sigma-Aldrich, St. Louis, Mo.), and GELGRO (ICN-MP Biochemicals, Irvine, Calif., USA) are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, callus, immature embryos, hairy root cultures, and gametic cells such as microspores, pollen, sperm and egg cells. Callus may be initiated from tissue sources including, but not limited to, immature embryos, seedling apical meristems, root, leaf, microspores and the like. Those cells which are capable of proliferating as callus also are candidate recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population, for example by manual selection and culture of friable, embryogenic tissue. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the application will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium and MS media.

C. Methods for Genetic Transformation

Suitable methods for transformation of plant or other cells for use with the present application are believed to include virtually any method by which DNA can be introduced into a cell, such as by direct delivery of DNA such as by PEG-mediated transformation of protoplasts, by desiccation/inhibition-mediated DNA uptake, by electroporation, by agitation with silicon carbide fibers, by *Agrobacterium*-mediated transformation, etc. Through the application of techniques such as these, the cells of virtually any plant species may be stably transformed, and these cells developed into transgenic plants.

i. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, U.S. Pat. No. 5,563,055.

*Agrobacterium*-mediated transformation is most efficient in dicotyledonous plants and is the preferable method for transformation of dicots, including Arabidopsis, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to e.g., rice, wheat, barley, alfalfa, and maize, among others.

Modern *Agrobacterium* transformation vectors are capable of replication in *E. coli* as well as *Agrobacterium*, allowing for convenient manipulations as described. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

ii. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize, wheat, tomato, soybean, and tobacco.

In some embodiments, protoplasts are employed for electroporation transformation of plants. For example, the generation of transgenic soybean plants by electroporation of cotyledon-derived protoplasts. Other examples of species for which protoplast transformation has been described include barley, sorghum, maize, wheat, and tomato.

iii. Microprojectile Bombardment

Another method for delivering transforming DNA segments to plant cells in accordance with the application is microprojectile bombardment. In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System (Dupont), which can be used to propel particles coated with DNA or cells through a screen, such as a stainless steel or nylon screen (e.g., NYTEX screen; Sefar America, Depew, N.Y. USA), onto a filter surface covered with plant cells cultured in suspension. The screen disperses the particles so that they are not delivered to the recipient cells in large aggregates. Microprojectile bombardment techniques are widely applicable and may be used to transform virtually any plant species. Examples of species for which have been transformed by microprojectile bombardment include monocot species such as maize, barley, wheat, and sorghum; as well as a number of dicots including tobacco, soybean, sunflower, peanut, cotton, tomato, and legumes in general.

iv. Other Transformation Methods

Transformation of protoplasts can be achieved using methods based on calcium phosphate precipitation, polyethylene glycol treatment, electroporation, and combinations of these treatments.

Application of these systems to different plant strains depends upon the ability to regenerate that particular plant strain from protoplasts. Illustrative methods for the regeneration of plants from protoplasts are well known in the art. Examples of the use of direct uptake transformation of protoplasts include transformation of rice, sorghum, barley, oat, and maize(.

To transform plant strains that cannot be successfully regenerated from protoplasts, other ways to introduce DNA into intact cells or tissues can be utilized. For example, regeneration of cereals from immature embryos or explants can be effected as known in the art. Also, silicon carbide fiber-mediated transformation may be used with or without protoplasting. Transformation with this technique is accomplished by agitating silicon carbide fibers together with cells in a DNA solution. DNA passively enters as the cells are punctured.

C. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the application. In this case, one would then generally assay the potentially transformed cell population by exposing the cells to a selective agent or agents, or one would screen the cells for the desired marker gene trait.

i. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism. Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide tolerance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity. The bar gene has been cloned and expressed in transgenic tobacco, tomato, potato, *Brassica*, and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the application is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, U.S. Pat. No. 6,566,587. The best characterized mutant EPSPS gene conferring glyphosate resistance comprises amino acid changes at residues 102 and 106, although it is anticipated that other mutations will also be useful (U.S. Pat. No. 6,566,587).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (U.S. Pat. No. 5,508,468).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

ii. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plantcon™ containers (MP-ICN Biomedicals, Solon, Ohio, USA). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. In one embodiment, the media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 week on media containing the above ingredients along with 10-5 M abscisic acid and then transferred to growth regulator-free medium for germination.

iii. Characterization

To confirm the presence of the exogenous MoMo30 DNA in the regenerating plants, a variety of assays may be performed. Such assays include, for example, Southern and northern blotting, and PCR; as well as detection of MoMo30 protein products, e.g., by immunological means (ELISAs and Western blots), by other assays for MoMo30 described in the Examples below; by plant part assays, such as leaf or root assays; and also, by analyzing the phenotype of the whole regenerated plant.

iv. DNA Integration, RNA Expression and Inheritance

Genomic DNA may be isolated from cell lines or any plant parts to determine the presence of the exogenous MoMo30 gene through the use of techniques well known to those skilled in the art. Note, that intact sequences will not always be present, presumably due to rearrangement or deletion of sequences in the cell. The presence of MoMo30 DNA elements introduced through the methods of this application may be determined, for example, by polymerase chain reaction (PCR). Using this technique, discreet fragments of DNA can be amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific MoMo30 DNA sequences introduced into the host genome and flanking host DNA sequences can be identified. Thus, the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Whereas DNA analysis techniques may be conducted using DNA isolated from any part of a plant, MoMo30 RNA will only be expressed in particular cells or tissue types and hence it will be necessary to prepare RNA for analysis from these tissues. Reverse transcriptase PCR (RT-PCR) techniques also may be used for detection and quantitation of RNA produced from the MoMo30 gene. By this approach it is first necessary to reverse transcribe the MoMo30 RNA into DNA, using enzymes such as reverse transcriptase, and then through the use of conventional PCR techniques to amplify the DNA. In most instances, PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

v. Gene Expression

While Southern blotting and PCR may be used to detect the MoMo30 gene, they do not provide information as to whether the corresponding protein is being expressed. Expression may be evaluated by determining expression via transcript-profiling techniques such as by use of a microarray, and by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be used as well.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and 14C-acetyl COA or for anthranilate synthase activity by following loss of fluorescence of anthranilate, to name two.

Frequently, the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

D. Plant Breeding

In addition to direct transformation of a particular plant genotype with a MoMo30 expression construct of the current application, transgenic plants may be made by crossing a plant having MoMo30 expression construct of the present application to a second plant lacking MoMo30 sequences. For example, a selected CT biosynthesis gene can be introduced into a particular plant variety by crossing, without the need for ever directly transforming a plant of that given variety. Therefore, the current application not only encompasses a plant directly transformed or regenerated from cells which have been transformed in accordance with the current application, but also the progeny of such plants. As used herein the term "progeny" denotes the offspring of any generation of a parent plant prepared in accordance with the application, wherein the progeny comprises a selected DNA construct prepared in accordance with the application. "Crossing" a plant to provide a plant line having one or more added transgenes relative to a starting plant line, as disclosed herein, is defined as the techniques that result in a transgene of the application being introduced into a plant line by crossing a starting line with a donor plant line that comprises a transgene of the application.

In some embodiments, a method for crossing a plant to provide a plant line expressing MoMo30 comprised the steps of: (a) plant seeds of the first (starting line) and second (donor plant line that comprises a transgene of the application) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

In other embodiments, a method for backcrossing a plant expressing MoMo30 for the purpose of transferring a MoMo30 sequence from a plant of a first genotype to a plant of a second genotype comprising the steps of (a) crossing a plant of a first genotype containing a desired gene, DNA sequence or element to a plant of a second genotype lacking the desired gene, DNA sequence or element; (b) selecting one or more progeny plant containing the desired gene, DNA sequence or element; (c) crossing the progeny plant to a plant of the second genotype; and (d) repeating steps (b) and (c) to transfer the MoMo30 sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

The present application is further illustrated by the following examples that should not be construed as limiting. The contents of all references, patents, and published patent applications cited throughout this application, as well as the Figures and Tables, are incorporated herein by reference in their entirety.

EXAMPLES

Example 1. Materials and Methods

1. Plant Extracts.

One hundred grams of dried leaves from *Momordica balsamina* were extracted in 1 L of distilled water overnight at 4° C. The liquid extract was separated from solid material through centrifugation at 4000×g for 30 min. at 4° C. The resulting supernatant was filtered through Whatman filter paper (Cat #3030). The extract was filter-sterilized by passing it through a 0.45-micron filter (Celltreat Cat #229703) and was kept frozen at −80° C. prior to lyophilization overnight.

2. Isolation of MoMo30.

The lyophilized powder was dissolved in nuclease-free water (Invitrogen Cat #AM9938) to create a 15 mg/mL solution. The solution was passed through 30 kD molecular weight cutoff filter at 4000×g for at least 10 minutes (Amicon ultra-15 cat #UFC903024) to remove low molecular weight contaminants. Once a retentate of 1 to 1.5 mL was obtained, the solution was passed through a 0.22-micron syringe filter (Celltreate Cat #229747) and stored at 4° C. (−20° C. for long term storage). The retentate contained one protein MoMo30 that was >95% pure as determined by SDS-PAGE and stained with Coomassie Brilliant Blue R-250 (Bio-Rad Cat #161-0400).

3. Multinuclear Activation of an Indicator (MAGI) Assay for Infectivity.

MAGI cell assays for infectivity were done as previously described (Khan M. et al. (2001) J Virol. 75:12081-7; Raymond A D et al. (2011) AIDS Res Hum Retroviruses 27:167-178). MAGI cells (AIDS reagent program cat #U373) were grown to 90% confluence. Cells were infected with 1 ng of p24 equivalent of HIV-1NL4-3 (AIDS reagent program cat #114). Infected cells were fixed and identified by cells exhibiting the development of blue color. Before staining, Cells were fixed using 1% Formaldehyde (F-79-500 Fisher Chemicals) and 0.2% Glutaraldehyde (F-02957-1 Fisher Scientific) in PBS. Staining solution was prepared to contain (14.25 ml PBS, 300 µl 0.2M potassium ferrocyanide, 300 µl 0.2M potassium ferricyanide, 15 µl 2M MgCl2 and 150 µl X-gal stock (40 mg/ml in DMSO). Two ml solution was added to each well and incubated at 37° C. for 50 min. Cells were washed twice with PBS and counted using light microscopy.

4. Determination of the Effect of MoMo30 on Infectivity.

A MoMo30 dose-response curve was carried out using MoMo30 concentrations from 1 to 100 nM. The IC50 of MoMo30 was determined by curve fitting using the Hill equation and determined using the Dr. Fit program (Di Veroli G Y et al. (2015) Scientific Reports 5:14701. For comparison, the commercially available fusion inhibitor Enfurvirtide (Sigma. SML0934). Briefly, MAGI cells were infected with 1 ng HIV-1NL4-3, Momo30+1 ng HIV-1NL4-3 and Enfuvirtide+1 ng HIV-1NL4-3 at different concentrations of MoMo30 and Enfuvirtide. After 48 hrs cells were fixed and stained.

5. Detection of MoMo30 in Serum.

To determine if the ingestion of plant extracts resulted in detectable levels of MoMo30 in the blood, two Rhesus macaques were given plant extracts using a scaled dosage to that typically given to humans. The macaques were given the plant extracts with food. Two grams of plant was given twice a day for a period of six months. Blood samples were taken at 0 days up to 183 days. Plasma was tested by SDS-PAGE and Western blot.

6. MTT Assay of MoMo30.

To determine if MoMo30 exhibits significant cellular toxicity at therapeutic levels, HEK 293 cells were exposed to concentrations of MoMo30 from 1 to 1000 nM and a mitochondrial toxicity test (MTT; Sigma Cat #CGD-1) was performed according to the manufacturer's recommendations. Percent viability was determined by comparison to an untreated control.

7. Stability Studies on MoMo30 and its Complex to Gp120.

To determine the stability of MoMo30 and its attachment to HIV-1, stock solutions of MoMo30 (4 ng/ml and 40 ng/ml) were subjected to temperatures from 25° C. to 120° C. for 30 min. After heating, the solution was mixed with 1 ng of HIV-1N14-3 and was added to a MAGI cell assay, and blue cells were counted. In a separate comparison study, 1 ng of HIV-1N1.4-3 samples were mixed with a stock solution of MoMo30 (400 ng/ml), incubated at 4° C., followed by collection of aliquots at time intervals from 5 min to 3 days, and centrifuged at 125,000 g through 20% sucrose cushion to remove free MoMo30 and then tested for infectivity by MAGI cell assay.

8. N-Terminal Sequencing of MoMo30.

Edman degradation was performed in two labs (Biosynthesis, Lewisville, TX, and Creative Proteomics, New York, NY). The analysis was performed on an ABI Procise 494HT (Thermo Fisher). The procedure determines the N-terminal amino acid sequence of proteins and peptides by the Edman degradation chemistry.

9. RNAseq to Determine the MoMo30 Gene Sequence.

RNAseq (GeneWiz) was used to determine the gene sequence of MoMo30. Total RNA was isolated from *M. balsamina* leaves by the Trizol method (~4 μg). RNAseq was done on the Illumina platform and the de novo transcriptome was assembled using Trinity software. The mRNA corresponding to the MoMo30 protein was determined by searching for the N-terminal sequence as determined by Edman degradation. Once the DNA sequence had been determined, the MoMo30 coding sequence was synthesized (Genscript) and cloned into the pGen-lenti vector which contains both a T7 promoter and a CMV promoter for expression in mammalian cells.

10. Software for Gene Assembly and Translation.

BLAST searches were done at the national center for biotechnology information (NCBI) web site. Comparisons of homology to various proteins and DNA sequences were done in SnapGene 6.0.2. Prediction of secondary structure was done at the Phyre2 structure prediction web portal (Kelley L A (2015) Nature Protocols 10:845-858).

11. Coupled Transcription/Translation of MoMo30 Gene.

The cloned version of the synthesized gene was expressed in the wheat germ coupled transcription/translation system (TNT T7 coupled Wheat Germ Extract System Promega Cat #L4140) according to the manufacturer's recommendations. Ten μl of product was resolved on a 4-20% SDS-PAGE gel and a Western blot was done using antibody to the N-terminal peptide of MoMo30. Ten μl of product was also tested in a MAGI cell infectivity assay to determine any antiviral effect. Since the pGen-lenti vector also contained a CMV promoter, HEK293 cells were transfected with the plasmid using Lipofectamine 3000 (ThermoFisher Scientific Cat #L3000008) following the manufacturers protocol and grown for 48 hrs. Conditioned medium was harvested, and cells were collected and lysed by using (Pierce RIPA buffer Cat #89901). Ten μl of cell pellet and 20 μl of conditioned medium was resolved on a 4-20% SDS-PAGE gel and blotted with N-terminal antibody to MoMo30. 100 μl of conditioned medium was used in a MAGI cell assay for evaluating antiviral effects.

12. Fluorescent Gp120 Binding Assay. P

Purified gp120 (ImmunoDX cat #1001-F) was added to a suspension of $1\times10^6$/ml Jurkat cells (AIDS reagent program ARP-177 E6-1 clone) allowed to interact for 2 h at 37° C. Free gp120 was removed by centrifugation, and the cells were resuspended in PBS. A portion was stained with Hoechst stain, and the cells were viewed under a fluorescent microscope using a neutral density filter, a blue filter, and a FITC filter.

13. Surface Plasmon Resonance (Biacore).

Surface plasmon resonance was done at the Biacore Molecular Interaction Shared Resource at Georgetown University. A Biacore T200 was used with a CM5 chip at 25° C. Purified gp120-IIIB (Immuno Dx, 1 mg/ml) in 1 mM sodium acetate buffer at pH 5.5 was used as a ligand to immobilize onto FC2, FC3, and FC4 to the levels of 8850 RU, 283RU, and 2980RU, respectively. Standard amine coupling chemistry was used. HBS-P (10 mM Hepes, pH 7.4, 150 mM NaCl, 0.05% v/v surfactant P20) was used as the immobilization running buffer. Overnight kinetics were performed for MoMo30 binding to the ligand. Injected compound concentrations were 102 μM to 0.1 μM. Three 15 second pulses of 1:250 $H_3PO_4$ (v/v, $ddH_2O$: $H_3PO_4$) were injected to regenerate the chip surface. All analyses were done in triplicate. The sensorgrams were obtained from overnight kinetics using 1:1 model fitting. In some experiments, gp120 was pre-treated with PNGase F (removes N-glycans) for 30 min at 50° C. before linkage to the chip surface. A control reaction was done with buffer alone. Three independent assays were done, each in triplicate.

14. MoMo30 Inhibition in the Presence of Mannose.

To determine the effect of mannose on the action of MoMo30, infectivity assays were carried out with 2 nM of MoMo30 in the presence of D-Mannose (Sigma cat #M6020) at concentrations from 0.002 to 2 nM, incubated at room temperature for five minutes, and added to MAGI cells for determination of infectivity inhibition by the MAGI cell assay.

15. 2G12 Antibody Blot for Changes in Gp120 Glycosylation Pattern.

The 2G12 antibody has been previously described (Scanlan C N et al., (2002) J. Virol. 76:7306-7321). This antibody recognizes a cluster of aspartate residues (N295, 332, 339, 386, 392) on the surface of gp120. The most likely epitope is likely to be N295 and 332. HIV-1$_{NL4-3}$ was produced by infecting 5×10$^6$ Jurkat cells (AIDS reagent program ARP-177 E6-1 Clone) with 300 ng HIV-1$_{NL4-3}$ (AIDS reagent program cat #114) in presence and absence of sufficient MoMo30 (60 nM) to reduce replication by >95%. Samples were collected 5, 8 and 12 days after infection and evaluated by Western blot using the 2G12 antibody to determine the effect of MoMo30 on this cluster of glycans.

16. Immunoblotting.

A rabbit antibody was produced (Genescript) from a 15-amino acid peptide with the N-terminal sequence of MoMo30. The antibody (at a dilution of 1:2000) was used to perform an immunoblot on purified protein resolved on a 4-20% SDS PAGE gel. Then were transferred to 0.2 µm Nitrocellulose membrane using Bio-Rad Trans-Blot Turbo for 20 min and blocked with 0.5% skim milk made in Tris buffer saline with 0.1% tween 20 (TBST) for 1 h and after that membrane was incubated with primary antibody 1:2000 in TBST overnight at 4° C. Three washes of ten minutes with TBST and a wash with distilled water between each wash. After which secondary antibody (G. E. Healthcare goat anti-rabbit Cat #NA934V) was added at a dilution of 1:25000 containing precision protein Strep Tectin-HRP (Bio-Rad Cat #1610380) 1:10,000 and allowed to incubate for 1 hour at room temperature. After this, the membrane was washed three times as previously, and chemiluminescent substrate (SuperSignal West Femto Thermo Scientific Cat #34096) was added and incubated for 5 min. The blot was visualized by a chemiluminescent imager (ThermoFisher iBright 1500). In some cases, the mouse monoclonal antibody 2G12 (AIDS reagent program; cat #1476) or a mouse anti-p24 antibody (AIDS reagent program; cat #6457) were used at a dilution of 1:1000 and used a mouse secondary antibody at a dilution of 1:25000.

Example 2. Preparation and Inhibitory Activity by the MoMo30 Protein

The present application is directed to compositions and methods comprising a 30 kDa MoMo30 product from *Momordica balsamina* plants. The functional activity of MoMo30 protein was originally assayed from *Momordica balsamina* plant extracts. In one non-limiting embodiment, the method comprises the steps of: (a) extracting dried *M. balsamina* leaves in water to form an aqueous extract; (b) removing solid material from the aqueous extract by centrifugation to form a supernatant; and (c) filter sterilizing the supernatant. The aqueous extract therefrom can be further frozen at −80° C. prior to lyophilization overnight.

Figure 3A:
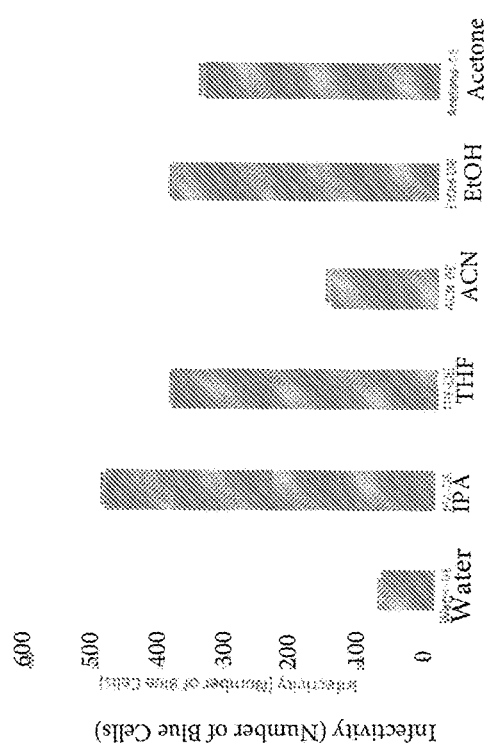
FIGS. 3A and 3B show the effects of different primary solvents (A) or extraction conditions (B) used in processing MoMo30 extracts relative to the amount of inhibition of HIV as determined by MAGI cell indicator assays. Lower bars indicate greater inhibition.
Figure 3B:
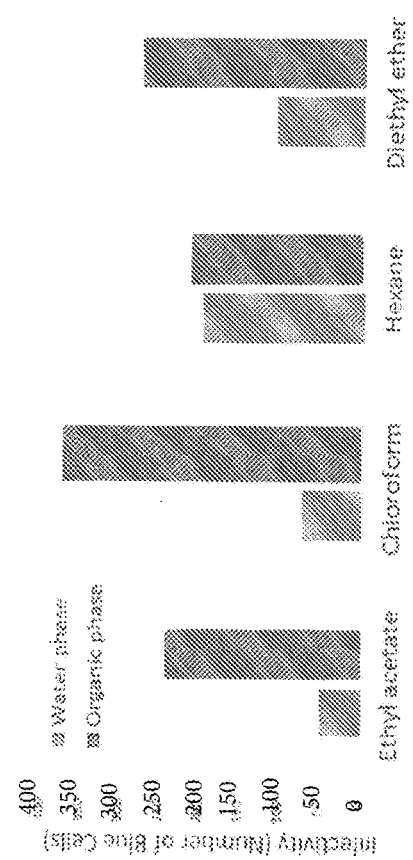

As further described below, MoMo30-containing extracts or purified proteins were tested for functional activity by testing their ability to inhibit infectivity by the MAGI cell infectivity assay (or "indicator assay") described above. The MAGI cell infectivity assay involves the use of genetically modified CD4-expressing HeLa cell line (MAGI) containing an HIV LTR-driven cassette placed upstream of the *E. coli* β-gal encoded reporter gene (HeLa-CD4-LTR-β-gal). Cells infected by HIV turn blue and can be counted under a microscope. In the figures that follow, the results depict inhibition of infectivity as a function of blue cells per nanogram of HIV-1 p24 capsid protein. In some cases, WT HIV-$1_{NL4-3}$ was used to allow multiple rounds of infectivity. By using HIV-$1_{NL4-3}$ with a deleted env gene and then supplying env in trans, the assay can test a single round of infectivity.

Example 3. *Momordica balsamina* has Anti-HIV-1 Activity

Water-soluble *M. balsamina* extracts were tested for their ability to inhibit HIV-1NL4-3 infection in a MAGI cell assay. More particularly, cell extracts were prepared and various amounts of extract (20 μg, 50 μg, 100 μg, 200 μg, 500 μg, and 1000 μg of total dry weight per milliliter of water) were mixed with 1 ng of HIV-1NL4-3 and tested for their ability to inhibit HIV-1NL4-3 infection in a MAGI cell reporter system (Khan M. et al. (2001) J Virol. 75:12081-7; Raymond A D et al. (2011) AIDS Res Hum Retroviruses 27:167-178). The results of this assay showed a dose-dependent reduction in the number of blue cells (indicating reduced infectivity), reaching 100% at 1000 μg/ml of extract (FIG. 2A). Moreover, there were no indications of cell toxicity. These data indicated that the plant extracts contained one or more antiviral agents.

As a follow-up, various concentrations of purified MoMo30 protein from 1 to 1000 nM were tested in a MAGI cell assay to determine the IC50 of MoMo30-HIV binding (FIG. 2B). Similar to the results in FIG. 2A, purified protein was able to inhibit HIV-1NL4-3 in a dose-dependent fashion. The IC50 of the protein was determined by curve fitting using the Dr. Fit program. As shown in FIG. 2B, the IC50 was determined to be 2.8 nM. The plot was curve-fit from triplicate measurements of two independently isolate purified protein preparations (top curve). For comparison, triplicate sample analysis of the commercially available HIV fusion inhibitor Enfuvirtide was conducted in parallel (FIG. 2B, bottom curve). The IC50 of Enfuvirtide was determined to be 44 nM, consistent with the previously published value of 26 nM (He Y et al. (2008) Proc. Natl. Acad. Sci. USA, 105:16332-16337).

Example 4. Physical and Chemical Properties of MoMo30

To further characterize the chemical nature of MoMo30, various extraction conditions were applied to preparation of the evaluate extraction of MoMo30 from *Momordica balsamina* plant extracts. Accordingly, *M. balsamina* leaves were directly extracted in water, isopropyl alcohol (IPA), tetrahydrofuran (THF), acetylnitrile (ACN), ethanol (EtOH), and acetone (FIG. 3A). These extracts were evaluated for their ability to inhibit HIV infection of MAGI indicator cells, where lower bars indicate greater anti-viral activity). As shown in FIG. 3A, the active agent can be extracted using water or acetylnitrile. This suggests that MoMo30 agent has both hydrophilic and hydrophobic properties, which is characteristic of larger molecules, such as proteins. The water-soluble nature of MoMo30 was further confirmed when testing the aqueous and organic phases obtained following extraction of *M. balsamina* leaves with ethyl acetate, chloroform, hexane and diethyl ether (FIG. 3B).

Example 5. The Antiviral Agent of Plant Extracts is a 30 kDa Protein

Figure 4C:
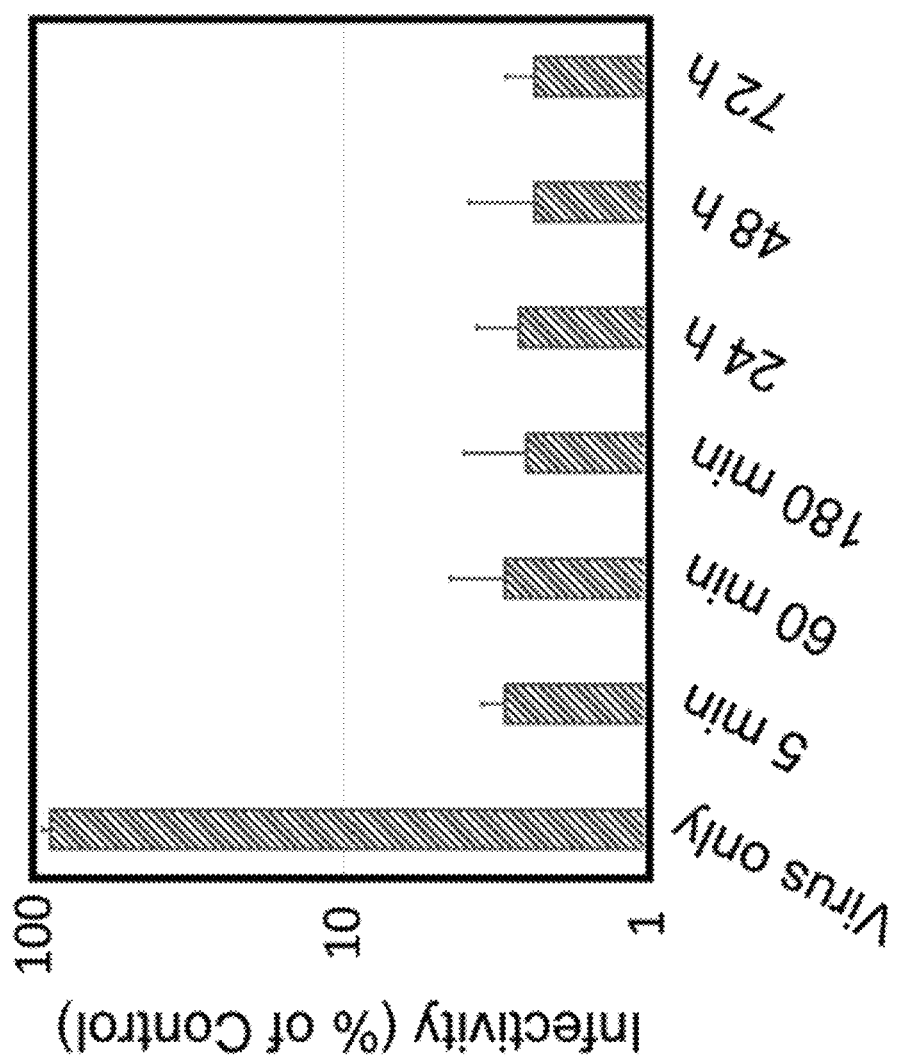
FIG. 4C shows that MoMo30 forms highly stable complexes with HIV-1. MoMo30 (3 nM) was mixed with an amount of HIV-1NL43 comprising 1 ng p24 and allowed to interact for 5 min prior to centrifugation through a 40% sucrose cushion. Virus-complexes were removed at times from 5 min to 72 h at 4° C. prior to testing for infectivity/blocking by the MAGI cell assay. All measurements were done in triplicate.

To determine the relative size of the active agent, extracts were passed through a series of molecular weight cutoff filters ranging from 3 to 100 kDa. It was determined that the antiviral activity of the extract was retained by most of the filters (see FIG. 4A). Only at the 100 kDa cutoff did more activity flow through the filter than was retained (FIG. 4A). This observation suggested that the active agent was likely a large molecule such as a protein. The extract products retained on the 30 kDa cutoff filter were electrophoresed on a 4-20% SDS-PAGE gel and a single band of approximately 30 kDa in size was detected (see FIG. 4B, Purified). Surprisingly, no other major bands were detected on the SDS-PAGE gel. Because this protein was isolated from a *Momordica* plant and was 30 kDa in size, the antiviral protein is referred to herein as "MoMo30". Molecular weight cutoff filters were henceforth used to separate MoMo30 from lower molecular weight contaminants and concentrate the protein.

Example 6. MoMo30 Stability and HIV Binding

The heat stability of MoMo30 was investigated by testing the ability of MoMo30 to inhibit HIV infectivity by the MAGI assay after incubating the protein at temperatures from 25° C. to 120° C. (autoclaving). The activity of MoMo30 was tested at concentrations of 40 ng/ml (top line) and 4 ng/ml (bottom line) over a range from 25° C. to 120° C. As shown in FIG. 4B, the percent infectivity of the purified protein remained unchanged over the broad temperature range tested.

To determine the stability of MoMo30 complexes formed with HIV-1, 100 ng/ml of MoMo30 was incubated with 1 ng of a p24 equivalent of HIV-$1_{NL4-3}$ virus. The complex of virus plus MoMo30 was then centrifuged through a 30% sucrose cushion at 125,000×g to remove any unbound MoMo30. The sucrose pellet containing virus plus bound MoMo30 was then tested for infectivity by the MAGI cell assay at time intervals from 5 min to 3 days. The results are summarized in FIG. 4C. Complexes of MoMo30 and HIV-$1_{NL4-3}$ virus retained 100% of their antiviral activity for at least 72 h suggesting that once formed, the complex of MoMo30 and virus remains stable.

Example 7. Detection of MoMo30 with Anti-MoMo30 Antibodies

Figure 5A:
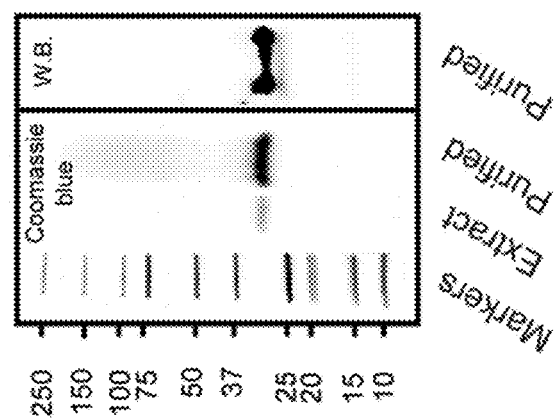
FIG. 5A shows that a *M. balsamina* extract passed through a 30 kD cutoff filter contains a prominent 30 kDa protein as visualized on a Coomasie blue stained 4-20%
Figure 5B:
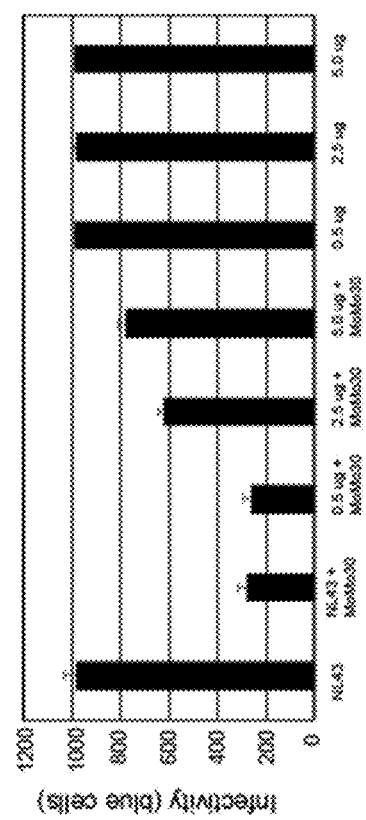
FIG. 5B shows that the anti-MoMo30 antibody blocked the ability of MoMo30 to inhibit HIV-1 infection in a dose-dependent manner (from 0.5 µg to 5.0 µg).

To provide a means for detection and immunopurification of MoMo30 protein from cells or cell extracts, a rabbit polyclonal antibody directed against the N-terminal amino acids of MoMo30 was generated. The N-terminal sequence of the first 15 amino acids was determined by Edman degradation (Creative Proteomics) to be GPIVTYWGQNVXEGEL (SEQ ID NO: 16). From this peptide, a rabbit antibody made that was used to perform Western analysis to confirm that the original 30 kDa band seen in the SDS-PAGE gel was the same protein submitted for Edman degradation (see FIG. 5A, W. B). FIG. 5B shows that in a MAGI assay, the anti-MoMo30 antibody blocked the ability of MoMo30 to inhibit HIV-1 infection in a dose-dependent manner (from 0.5 µg to 5.0 µg).

Example 8. Identification of the MoMo30 Gene

To identify the MoMo30 gene in *Momordica balsamina*, the following protocol was carried out: (1) isolate total plant RNA from *Momordica balsamina* leaves; (2) submit RNA for RNAseq de novo transcriptome analysis (GeneWiz); (3) assemble reads in Trinity 2.5 software; (4) search for open reading frames (EMBOSS); (5) translate into protein sequences (Diamond BLASTx annotation); and (6) search protein sequences for hevamine-related sequence motifs.

The Diamond BLAST search of open reading frames (ORFs) identified a Hevamine A-like sequence translated from the RNAseq data having strong homology (but not identical) to the N-terminal amino acid sequence (i.e., SEQ ID NO: 16) of MoMo30. The complete MoMo30 nucleotide coding sequence assembled from RNAseq reads is shown in FIG. 6 (SEQ ID NO: 1). A nucleic acid database search of the MoMo30 nucleotide coding sequence found the MoMo30 sequence to be 93% identical to the hevamine A-like gene from *M. chantaria* (NCBI Reference Sequence: XM_022291555.1; FIG. 6, SEQ ID NO: 5) and 26% identity to the *M. charantia* MAP30 protein. Residues that are different are shaded.

A translation of the MoMo30 nucleotide coding sequence is shown in FIG. 7, panels A and B. An alignment of the MoMo30 amino acid coding sequence in SEQ ID NO: 3 with the translation product of the *Momordica charantia* hevamine A-related nucleotide sequence in FIG. 6 (via SnapGene) shows 91% identity at the protein level. Secondary structure predictions (by Phyre2 website) of the *M. balsamina* MoMo30 and the *M. charantia* hevamine A-like ORF are shown in FIG. 7, panel A. The predicted secondary structure shows strong homology to a TIM β-barrel (a structure that is commonly found in Hevamine A-like proteins (Wierenga R K, (2001) FEBS Letters 492:193-198. The TIM structure is reported to be a very heat stable conformation (Romero-Romero S et al., (2021) J. Mol. Biol., 433:167153-167153), which is consistent with the profound heat stability of MoMo30 shown in FIG. 4B.

Hevamines are members of several families of plant chitinases and lysozymes that are important for plant defense against pathogenic bacteria and *fungi* and belong to the family 18 glycosyl hydrolases. Hevamines are known to hydrolyze linear polysaccharide chains of chitin and peptidoglycan. The MoMo30 protein was resistant to proteolysis by most proteases, including trypsin, which is used in most liquid chromatography with tandem mass spectrometry strategies. However, the MoMo30 protein was found to be sensitive to proteolysis by subtilisin (data not shown). Like other chitinases, MoMo30 was found to exhibit chitinase activity (data not shown).

Further, as shown in FIG. 6, the MoMo30 sequence of SEQ ID NO: 1 has a signal peptide-encoding sequence having an amino acid sequence present in amino acid residues 1-31 in SEQ ID NO: 7, panel A, which is removed in the secreted mature protein. FIG. 7, panel B shows the amino acid sequence of the mature MoMo30 protein (SEQ ID NO: 4) in secreted form having a predicted molecular weight of 30.9 kDa. The nucleotide sequence corresponding to the secreted form of MoMo30 is set forth in SEQ ID NO: 2.

FIG. 8 shows an alignment of two conserved regions from the MoMo30 protein relative to other hevamine A-related proteins comprising the amino acid sequences set forth in SEQ ID NOs: 7-15.

Figure 9:
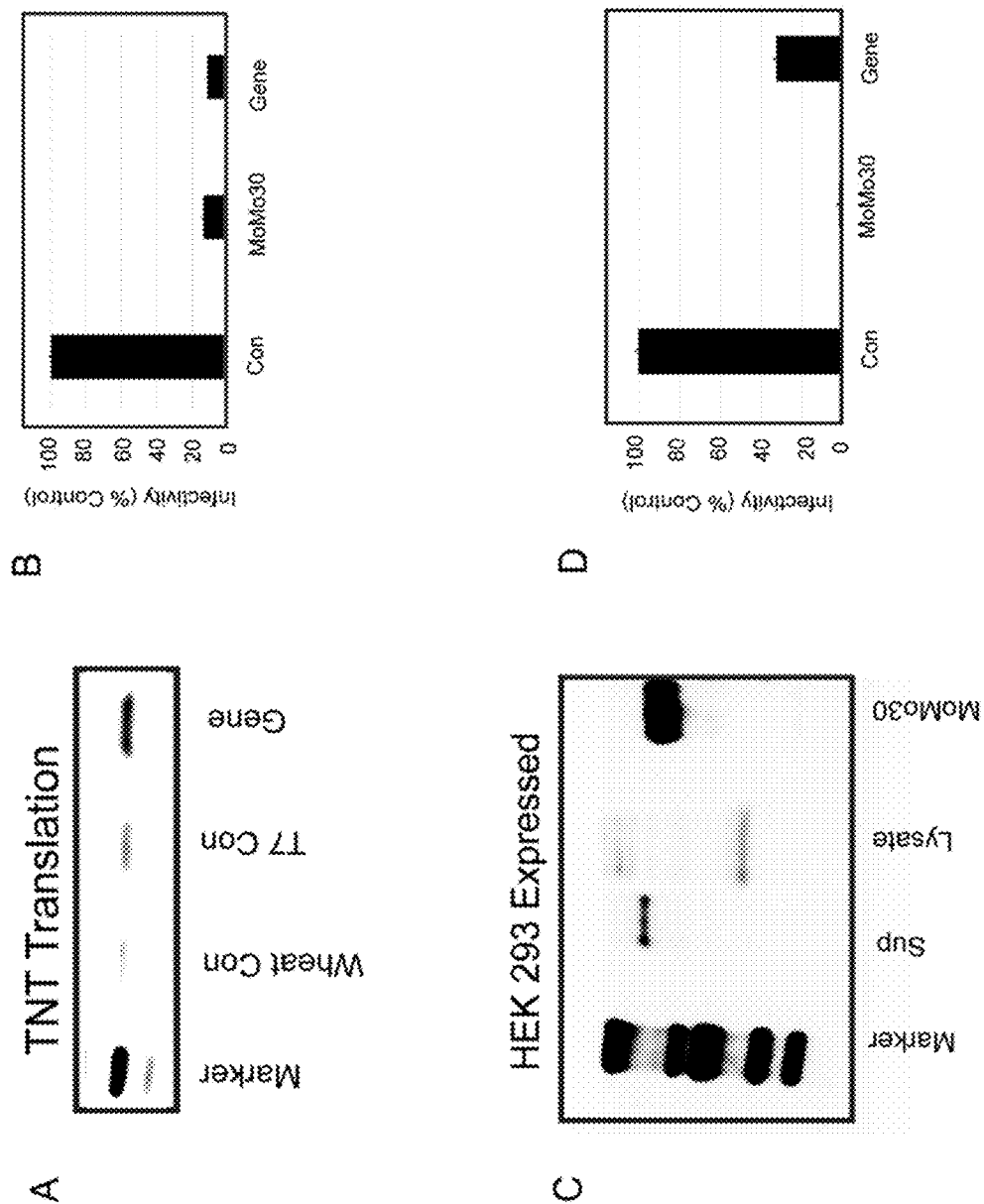
FIG. 9, panel A shows a 30 kD in vitro translated MoMo30 product. The MoMo30 gene was inserted into a pGEM vector that was used as a template for coupled transcription/translation. The reaction was run on a 20% SDS-PAGE gel and a western blot was probed with an N-terminal ab to MoMo30. A sample of purified MoMo30 is used as a marker. Panel B shows that the translation products have anti-HIV activity as determined by a MAGI assay. In panel C, the MoMo30 pGEM plasmid was transfected into HEK 293 cells, followed by collection of supernatants and cell lysates therefrom, which were run on a 20% SDS-PAGE gel and probed with the N-terminal MoMo30 ab. In panel D, 10 µl of cell-free conditioned medium was tested for HIV infectivity by the MAGI assay.

Example 9. In Vitro Transcription/Translation of the Hevamine A-Like MoMo30 Gene Produces an Antiviral Effect The MoMo30 coding sequence derived from the RNAseq data was synthesized (Genscript) and cloned into the pGen-lenti vector expression plasmid. In vitro coupled transcription and translation was carried out with the expression plasmid using the TNT wheat germ extract system (FIG. 9, panel A). A MAGI assay was performed using the reaction product to confirm that the product exhibits an antiviral effect. The synthesized product (FIG. 9, panel A) was able to inhibit HIV-1 similar to purified MoMo30 (FIG. 9, panel B). The product was also reactive with the N-terminal MoMo30 antibody (FIG. 9, panel C). Western blot analysis revealed an ~30 kDa protein in the supernatant, suggesting that the protein (synthesized with the native signal peptide sequence) was secreted, and the signal peptide was cleaved. Cell-free supernatants of HEK-293 cells transfected with the MoMo30 expression plasmid were tested for antiviral activity by the MAGI assay. As shown in FIG. 9, panel D, the tissue culture supernatants were found to significantly inhibit HIV-1 infectivity. Together, these data indicate that the MoMo30 is an *M. balsamina* hevamine A-like protein capable of inhibiting HIV-1 infection.

Example 10. MoMo30 Binds HIV-1 gp120 and Blocks its Binding to Jurkat Cells

Figure 10:
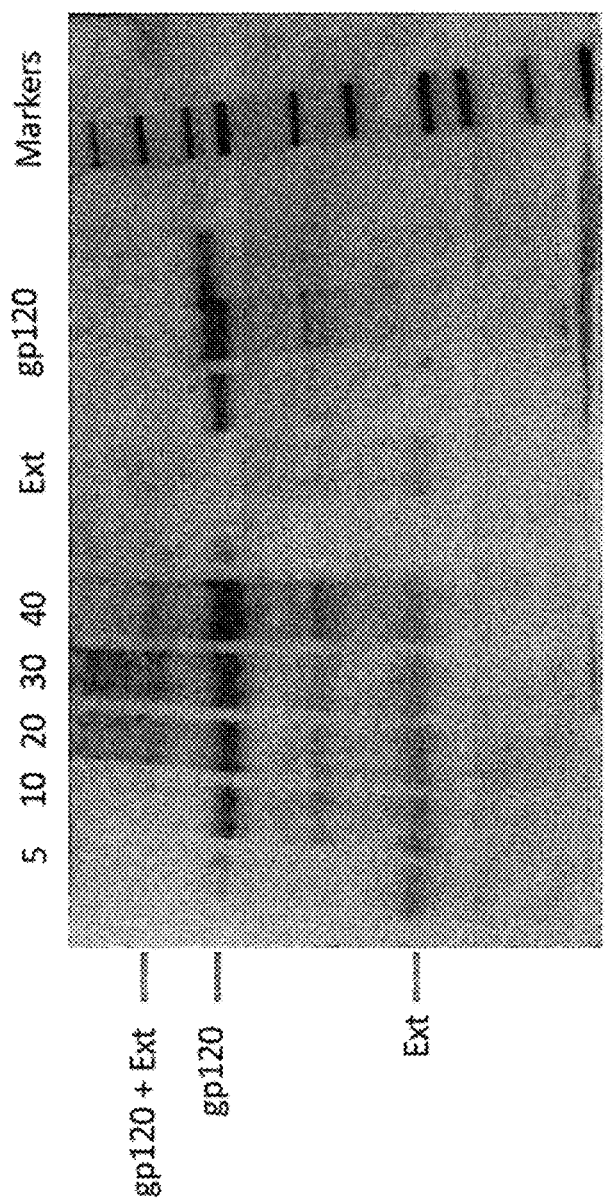
FIG. 10 is a Coomasie stained SDS-PAGE showing that the 30 kDa MoMo30 protein from extract A ("Ext") binds to increasing levels of purified HIV gp120 (in relative amounts 5, 10, 20, 30 and 40) and induces it to undergo a shift in MW (see "gp120+Ext"). Note the shift in mobility is evident even after boiling in loading buffer and despite the denaturing conditions in the gel.
Figure 11:
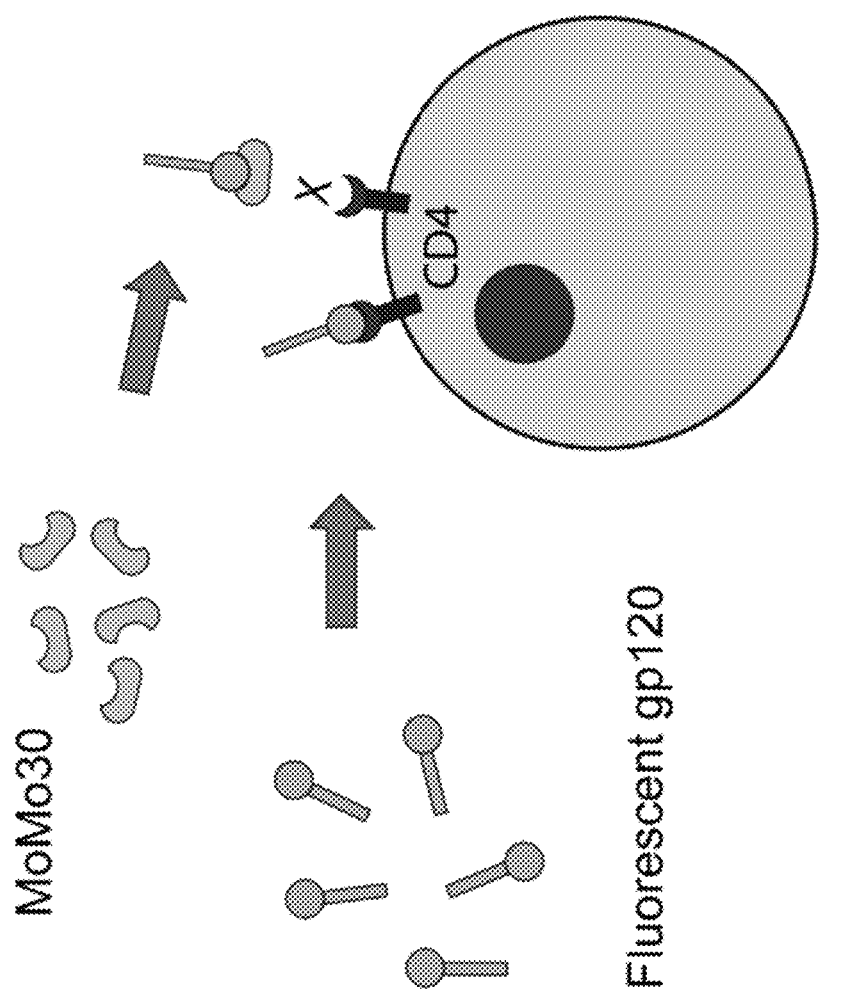
FIG. 11 is a schematic depiction of a blocking assay to examine whether MoMo30-containing extracts from *M. balsamina* inhibit the binding of purified HIV gp120 to CD4. Purified fluorescently labeled gp120 (30 µg, ImmunoDx) was added to 1×106 Jurkat T cells either with PBS or a pooled combination of extracts.

To further characterize the antiviral properties of the 30 kDa hevamine A-related protein, a *M. balsamina* plant extract was incubated with purified HIV-1 gp120 loaded on a non-denaturing polyacrylamide gel. The results of this analysis showed that the 30 kDa protein in the plant extract binds HIV-1 gp120 inducing a band-shift as shown in FIG. 10A. Further, this interaction was not disrupted by boiling or denaturing conditions of the gel (data not shown).

Figure 12:
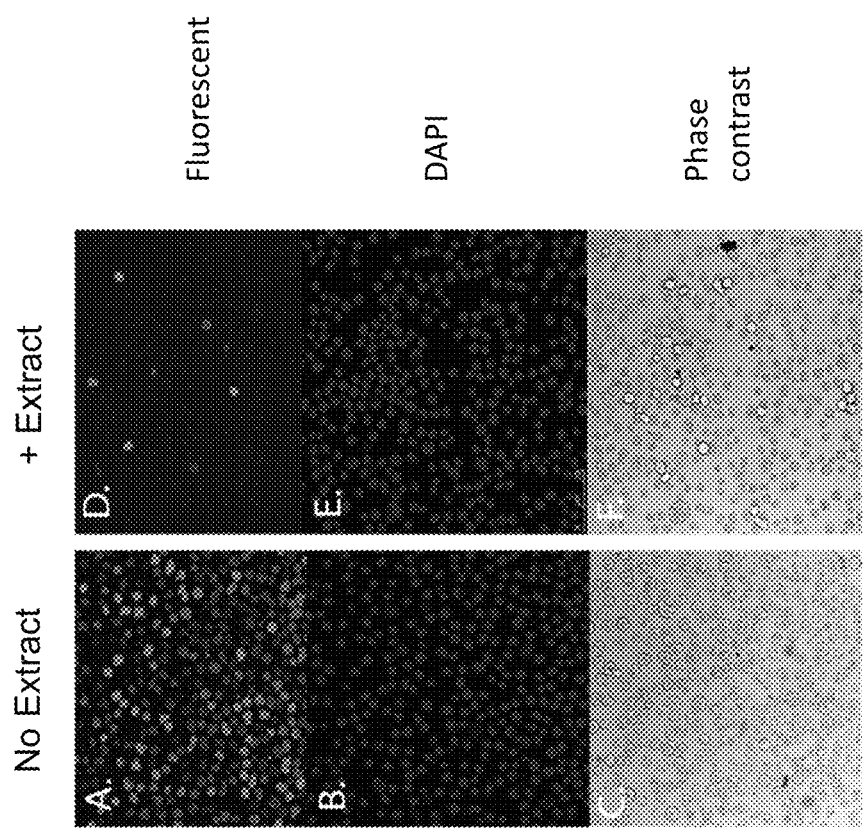
FIG. 12, panels A-F show the results of a fluorescence binding assay (as depicted in schematic in FIG. 11). Briefly, Jurkat T cells are mixed with FITC labeled gp120 either in the absence (panels A-C) or presence (panels D-F) of extract A. The results show that binding of fluorescently labeled gp120 to the surface of Jurkat T-cells (panel A) is inhibited in the presence of the MoMo30-containing plant extracts (panel D). Panels B and E are the same cells stained with DAPI and panels C and F depict the same cells under phase contrast.

To further confirm this binding in the context of live cells, a blocking assay was carried out to determine the stage of viral replication inhibited by MoMo30. To assay attachment of gp120 to susceptible cells, purified FITC labeled gp120 was mixed with Jurkat cells. FITC labeled gp120 binds the cell surface to make it visible. In the absence of MoMo30, the purified gp120 can attach to CD4 on the surface of Jurkat cells (see FIG. 12, panels A to C). A stock solution of 200 nM of MoMo30 (sufficient to completely inhibit 1 ng of virus) was pre-incubated with the gp120 before adding the Jurkat suspension. Treatment with MoMo30 blocked the interaction of gp120 with Jurkat cells (compare FIG. 12, panel A to panel D). This finding is consistent with MoMo30 blocking the initial step in replication by binding to gp120 and blocking entry.

Example 11. MoMo30 Binds to the Glycan Residues of Gp120

Figure 13A:
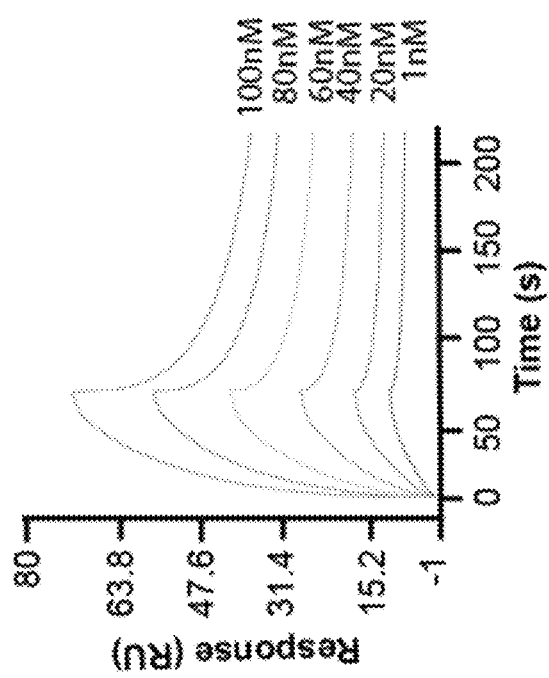
FIG. 13A shows a surface plasmon resonance (SPR) analysis (Biacore) indicating that MoMo30 protein from a cell extract attaches to HIV gp120 so as to prevent its interaction with the CD4 receptor. Gp120 was immobilized on the gold surface and MoMo30 protein was flowed across the surface at concentrations from 6 to 200 nM. The assay was done in triplicate on separate days.

To further characterize the interaction of MoMo30 with gp120, surface plasmon resonance (Biacore) experiments were carried out. Purified gp120 was bound to a chip surface, and MoMo30 at concentrations from 1 to 100 nM was allowed to flow across the surface, allowing the binding to be further characterized. Increasing concentrations of MoMo30 showed proportional reflectance increases of the chip (FIG. 13A). Three independent measurements in triplicate gave a kd of 2.42×10-3, K. D. of 6.0 µM, and ka of 400.5 1/Ms. The binding profile suggests that there is a fast on rate and a biphasic off rate. The initial dissociation is rapid, followed by a very slow dissociation.

Figure 13B:
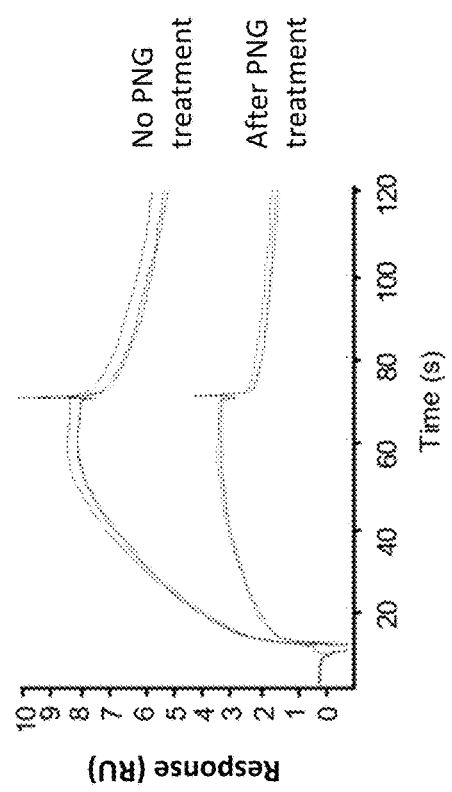
FIG. 13B shows that binding of MoMo30 to gp120 is dependent on glycosyl residues on gp120. A Biacore chip was saturated with gp120 and MoMo30 (top curves). The gp120-MoMo30 complexes were treated with PNG glycosylase to remove sugar residues from gp120 (bottom curves). Loss of sugar residues resulted in a decrease in binding.

To further characterize the binding of MoMo30 to gp120, purified gp120 was pre-treated with PNGase F. PNGase F is an amidase that works by cleaving between the innermost GlcNAc and asparagine residues of high mannose, hybrid, and complex oligosaccharides from N-linked glycoproteins and glycopeptides, resulting in a deaminated protein or peptide and a free glycan. Following treatment with PNGase F, a dramatic decrease in binding to the chip surface was observed (see FIG. 13B), the loss of sugar residues produced a decrease in reflectance units (RU), reflecting a decrease in MoMo30 binding to gp120, suggesting that MoMo30 binds to glycan residues in gp120.

Example 12. Effect of Mannose Monosaccharide and Glycan Specific mAbs on Inhibition of Infection by MoMo30

Figure 14A:
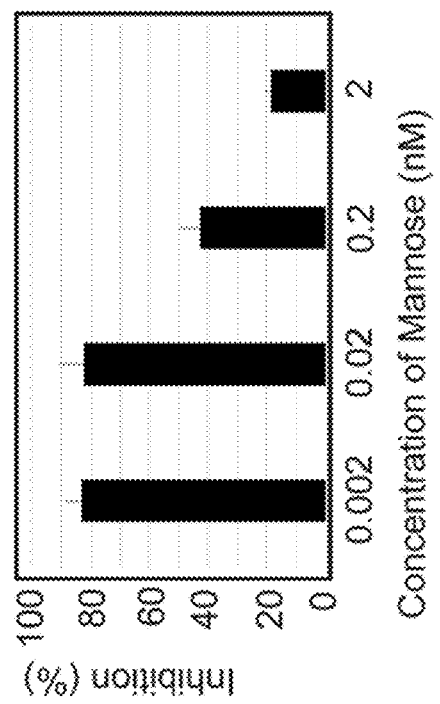
In FIG. 14A, Gp120 was bound to a Biacore chip surface and MoMo30 was allowed to flow across the chip at concentrations from 1 nM to 100 nM. Binding was monitored by changes in surface plasmon resonance.

The glycans on gp120 comprise a mixture of high mannose glycans and complex-type mannose glycans. To determine the effect of adding mannose in the context of MoMo30 binding to HIV-1NL4-3, HIV-1NL4-3 was incubated with MoMo30 (2 nM) in the presence of mannose concentrations from 0 to 2 nM (FIG. 14A). The results of this experiment showed that inhibition of HIV by MoMo30 was entirely abolished by the presence of mannose at a concentration of 2 nM, which is a 1:1 molar ratio with MoMo30, thereby suggesting a single binding site in gp120 (FIG. 14A).

Figure 14B:
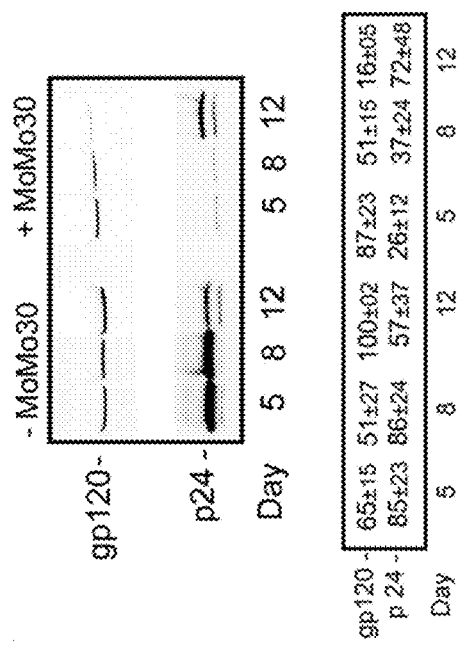
FIG. 14B shows that exposure of HIV-1 to MoMo30 reduces its reactivity with the glycan specific mAb 2G12. Virus was harvested at days 5, 8, and 12 and concentrated by centrifugation at 125,000×g through a 30% sucrose cushion. The pellet was subjected to SDS-PAGE and an immunoblot was done using anti-gp120 glycosyl specific antibody 2G12 and p24 mouse antibody.

The monoclonal antibody 2G12 has been previously shown to react with specific high mannose glycans on the surface of gp120 (Punja Z K et al. (1993) J Nematol 25:526-40; Sahai A S et al. (1993) FEMS Microbiology Reviews 11:317-338), most likely N295 and N332 (Scanlan C N et al., (2002) J. Virol. 76:7306-7321). To determine the effect of MoMo30 on reactivity with the antibody 2G12, Jurkat cells were infected with HIV-1NL4-3 in the presence or absence of 1 nM MoMo30. Virus was harvested on days 5, 8, and 12 after initial exposure and the resulting particles were subjected to immunoblot analysis using the mAb 2G12 (FIG. 14B). The results of this experiment showed that exposing HIV-1 to MoMo30 appears to reduce reactivity over time with the glycan specific mAb 2G12. This is consistent with the observation that MoMo30 binds to glycan residues on the surface of gp120 and supports the conclusion that carbohydrate residues become inaccessible as a result of the binding.

Example 13. MoMo30 Binds to Other Viruses

Figures 15, 16:
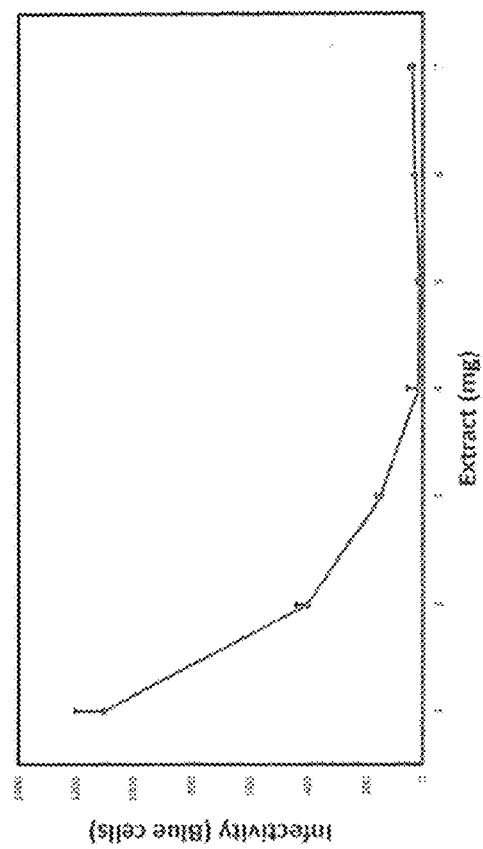
FIG. 15 shows inhibition of simian immunodeficiency virus (SIV-mac239) infectivity by MoMo30 cell extracts.
FIG. 16 shows inhibition of Ebola virus (Zaire strain) infectivity in HeLa or HFF cells by MoMo30 cell extracts.

To determine whether the antimicrobial properties of the active agent in the plant extracts are specific for HIV or could be extended to other viruses as a broad-spectrum antimicrobial agent, a MAGI cell infectivity assay was performed in simian immunodeficiency virus (SIV) infected cells, the results of which are shown in FIG. 15. Additionally, EBOV assays were carried out in Ebola virus infected cells treated with several different independently obtained MoMo30 extracts (A-E). Infectivity was determined by immunofluorescence using anti-EBOV antibodies. As shown in FIG. 16, each of the MoMo30 extracts was shown to exhibit anti-EBOV activity in both Hela and HFF cell lines as indicated by the EC50 (concentration required to obtain a 50% effect). For all extracts, the potency values were slightly better in Hela cells than in HFF. The safety index (SI) was low for extracts A and C in Hela cells.

Figure 17:
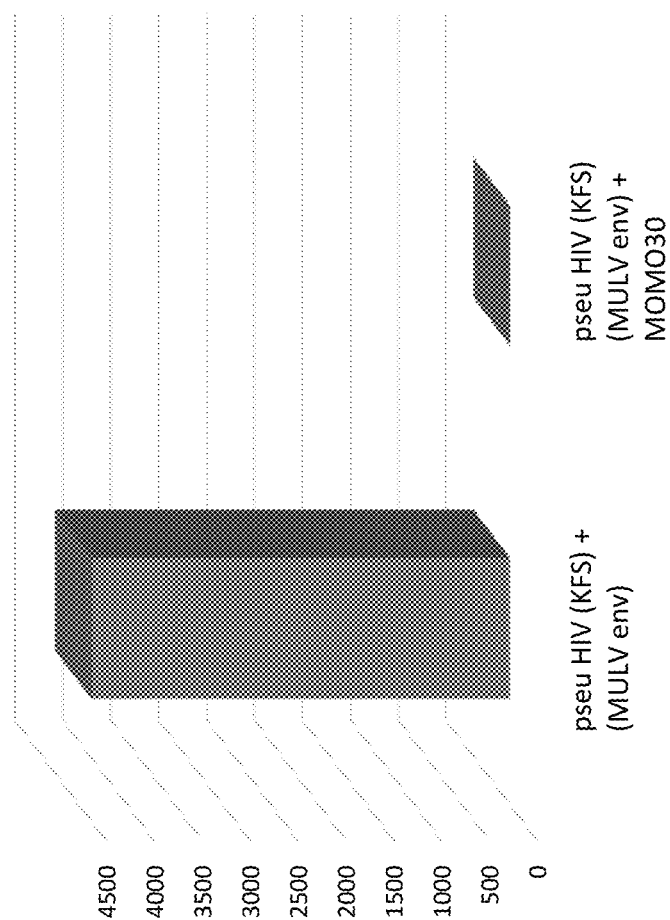
FIG. 17 shows that an HIV-1 pseudotyped with the aMLV envelope protein is sensitive to MoMo30 inhibition. An env deleted HIV-1 strain (KFS) pseudotyped to contain the MuMLV envelope glycoprotein was tested for infectivity in the absence (left) or presence (right) of MoMo30.

As an extension of this analysis, an envelope (env) deleted HIV-1 strain (KFS) pseudotyped to contain the MuMLV envelope glycoprotein was tested for infectivity in the absence (left) or presence (right) of MoMo30 (FIG. 17). The results of this assay showed that an HIV-1 pseudotyped with the aMLV envelope protein is sensitive to MoMo30 inhibition, suggesting that the antiviral properties of MoMo30 broadly extend to a variety of enveloped viruses via glycosylated surface envelopes. Taken together, these results are consistent with the active agent having broad-spectrum antimicrobial properties.

Figure 2A:
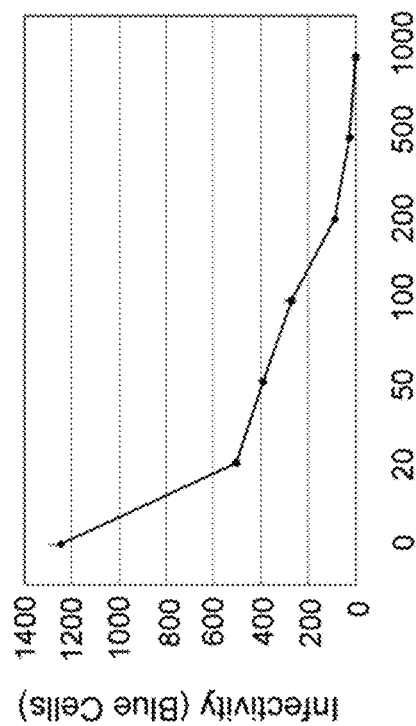
FIG. 2A shows that water soluble extracts from dried leaves extracts of *Momordica balsamina* contain an anti-HIV activity. The water-soluble extracts were tested at concentrations from 0 to 1000 μg/ml and scored for infectivity using a MAGI assay.
Figure 2B:
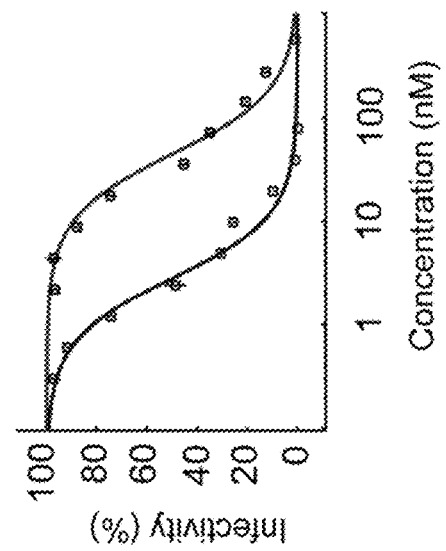
FIG. 2B shows an IC50 determination of inhibitory activity against HIV-$1_{NL43}$ by exposing 1 ng of HIV-$1_{NL43}$ to concentrations of MoMo30 from 1 to 100 nM and determining the percent infectivity (or inhibition) by MAGI assay. The IC50 value was determined by curve-fitting using Dr. Fit software. The top curve shows MoMo30 inhibition. The bottom curve shows a comparison to the commercially available HIV inhibitor, Enfuvirtide.
Figure 18:
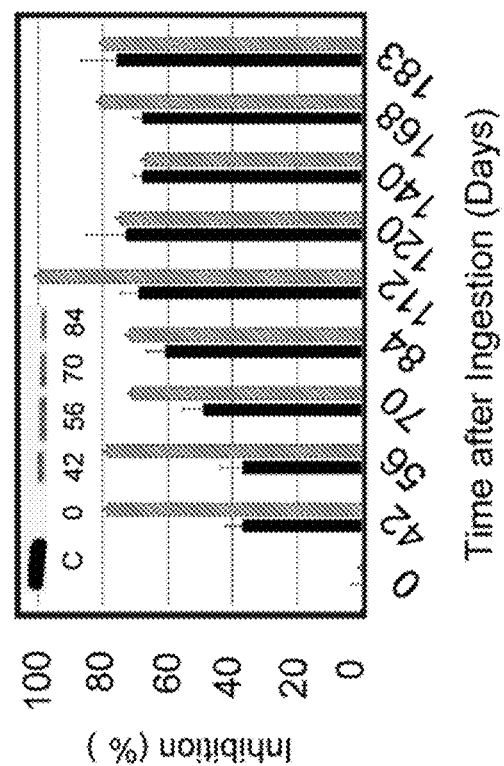
FIG. 18 shows adsorption of MoMo30 to the serum of Rhesus macaques. Two macaques were given herbal therapy in the same regimen as that given in the field (adjusted for weight). Three microliters of serum was tested by the MAGI assay (in triplicate) for antiviral effects at times from 0 to 183 days. The inset shows a western blot using N-terminal MoMo30 ab and 15 µl the sample in crosshatched bars.

Example 14. Orally Provided MoMo30 can Accumulate Stably in the Bloodstream of a Non-Human Primate To determine MoMo30 bioavailability in the bloodstream, *M. balsamina* extracts of the medicinal plants were administered to two Rhesus macaques by mouth for six months. MAGI infectivity assays and Western blots were carried out to confirm the presence of MoMo30 in the serum of treated animals (FIG. 18). Serum was tested from 0 to 183 days after ingestion. Neither of the animals exhibited inhibitory activity in their serum prior to ingestion of the plant extract. However sera from both possessed significant amounts of antiviral activity by 42 days post-ingestion (FIG. 2C). A Western blot was carried out using the anti-MoMo30 antibody described herein. A representative Western blot of serum from the animal is represented by the cross-hatched bars is shown as an inset to FIG. 18. Neither animal had detectable protein present in their serum before ingestion.

Example 15. MoMo30 is not Toxic to MAGI Cells at Therapeutic Levels

Figure 19:
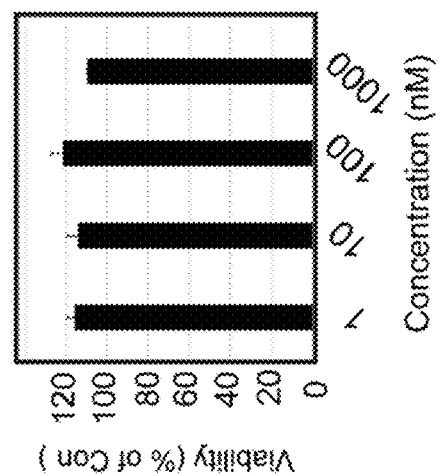
FIG. 19 shows the results of an MTT assay demonstrating a lack of cellular toxicity by MoMo30 protein at concentrations between 1 to 1000 nm.

To confirm the absence of toxicity at the cellular level, the effect of various MoMo30 concentrations (1 to 1000 nM) on MAGI cells was evaluated. Specifically, a cellular viability (MTT) assay measuring a cell's metabolic activity was carried out in which metabolic activity is reduced if the compound is toxic. As shown in FIG. 19, the treated cells showed no toxic effect at concentrations needed to inhibit HIV infection.

Example 16. MoMo30 Causes Hemagglutination

Figure 20A:
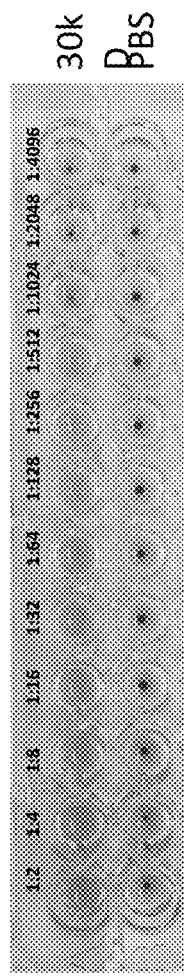
FIG. 20A shows that MoMo30 causes hemagglutination. Purified MoMo30 was tested for its ability to agglutinate sheep red blood cells (RBCs). As shown in panel A, the stock solution at a dilution of 1:512 was found to cause hemagglutination.

The observation that MoMo30 appears to bind sugar groups in a range of viral envelopes suggests that it has properties reminiscent of lectins. Inasmuch as lectins have often been found to exhibit hemagglutinin activity, it was of interest to investigate whether MoMo30 exhibits hemagglutinin activity too. FIG. 20A shows the results of this analysis. In this case, purified MoMo30 protein was tested for its ability to agglutinate sheep red blood cells (RBCs). As shown in panel A, a 30 mg/ml stock solution at a dilution of 1:512 was found to cause hemagglutination, consistent with lectin-like activity.

Example 17. MoMo30 Stimulates the Activation and Proliferation of T Cells

Figure 20B:
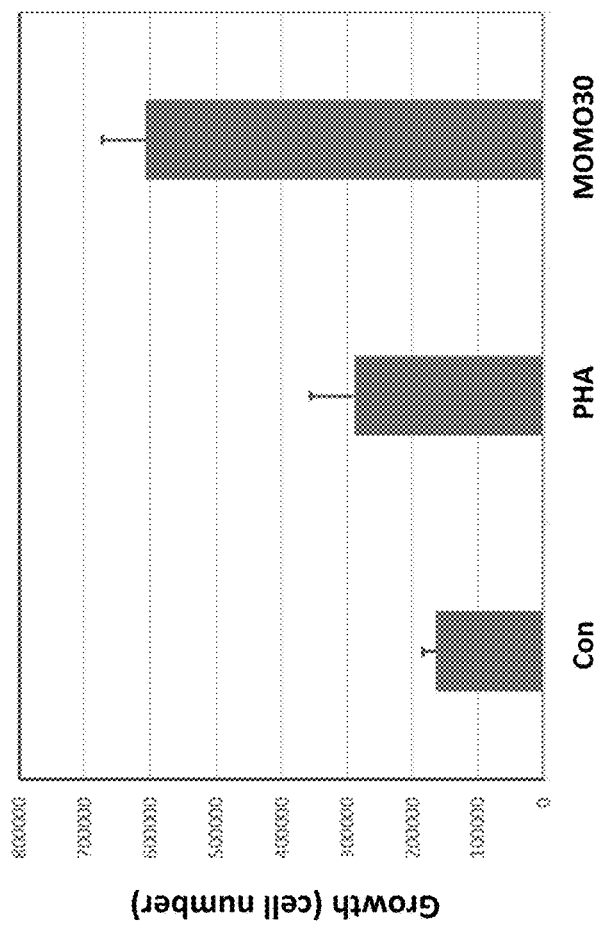
FIG. 20B shows that MoMo30 stimulates T cell growth. In each experiment, a fixed number of Jurkat cells was treated (left to right) with either PBS (control, Con), phytohemagglutinin A (PHA) or an equal amount of MoMo30.

Inasmuch as lectins are known to function as T cell mitogens, such as phytohemagglutinin A (PHA), it was of interest to examine whether MoMo30 can stimulate the activation and proliferation of T cells. Thus, a T cell activation assay was performed in which a fixed number of Jurkat cells was treated (left to right) with PBS (neg. control, Con), PHA (pos. control), or MoMo30 (FIG. 20B). The results of this assay showed that MoMo30 similarly stimulates the activation and proliferation of T cells.

Example 18. Clinical Study of HIV Patients Treated with a MoMo30 Herbal Tea

To examine the therapeutic efficacy of the MoMo30 protein, HIV-infected patients (n=61) were orally administered a combination of Extracts A-E daily for a period of 6 months during which no other anti-retroviral agents (ARVs) were administered. The extracts were administered in the form of an herbal tea. During this 6 month treatment period, the patients' viral loads (FIG. 21A) and CD4+ lymphocyte counts (FIG. 21B) were monitored. The results of this analysis showed that the average viral load was significantly reduced (FIG. 21A), while the CD4+ cell counts increased over this same period (FIG. 21B). A follow-up done over 10 years later (180 months) showed that some of the treated patients are healthy and exhibit undetectable or extremely low HIV virus levels (FIG. 21A).

Table 1 shows individual patient data evaluating viral loads and CD4+ cell counts in the follow-up patients compared to healthy, uninfected control subjects, where NP=Not performed (specimen clotted) and ND=Not detected <20 copies/ml.

TABLE 1

| Patient Number | % CD4+ cells/total lymphocytes | No. CD4+ cells/ml | No. total lymphocytes/ml | Viral Load (<20 copies) |
| --- | --- | --- | --- | --- |
| Uninfected Control Subjects | | | | |
| 1 | 26 | 422 | 1630 | ND |
| 2 | 53 | 539 | 1019 | ND |
| 3 | 23 | 175 | 762 | ND |
| 4 | 50 | 116 | 230 | ND |
| 5 | 28 | 211 | 761 | ND |
| 6 | 21 | 374 | 1797 | ND |
| 7 | 32 | 139 | 434 | ND |
| 8 | 45 | 185 | 414 | ND |
| 9 | 28 | 82 | 298 | ND |
| 10 | 13 | 206 | 1634 | ND |
| 11 | 37 | 565 | 1518 | ND |
| 12 | 49 | 106 | 215 | ND |
| 13 | NP | NP | NP | ND |
| Control Avg | 34 | 260 | 893 | |
| Follow-Up Patients 10 Years After Treatment | | | | |
| 14 | 21 | 95 | 444 | ND |
| 15 | 36 | 61 | 170 | ND |
| 16 | 47 | 73 | 154 | ND |
| 17 | 16 | 146 | 895 | 3360 |
| 18 | 24 | 78 | 322 | ND |
| 19 | 33 | 969 | 2909 | 20 |
| 20 | 21 | 180 | 855 | ND |
| 21 | 32 | 95 | 294 | 3600 |
| 22 | 14 | 110 | 768 | ND |
| 23 | 29 | 314 | 1094 | ND |
| 24 | 32 | 283 | 892 | ND |
| 25 | 29 | 649 | 2253 | ND |
| 26 | 13 | 112 | 897 | ND |
| Patient Avg | 27 | 243 | 919 | |

The results of the follow-up study showed that the treated patients showed similar CD4 and viral load profiles compared to the uninfected control subjects.

Figure 22:
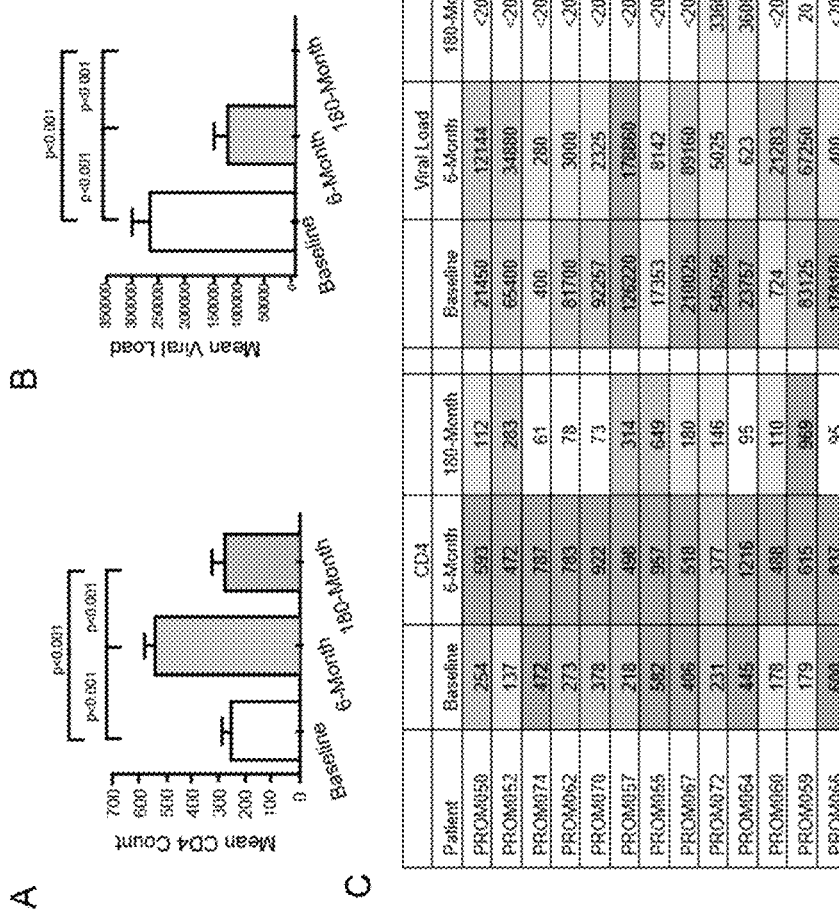
FIG. 22, panels A and B further show the results of the clinical study depicted in FIGS. 21A-21B where an increase in CD4+ lymphocytes of about 50% was observed following 6 months of treatment with the (FIG. 22, panel A), and a decrease of 60% of the patients' mean HIV viral loads was observed following a 6-months post-treatment (FIG. 22, panel B), which typically decreased to undetectable levels after 180 months (FIG. 22, panel B).

FIG. 22, panels A and B further show the results of the clinical study above, further documenting an increase in CD4+ lymphocytes of about 50% following 6 months of treatment with MoMo30 plant extract (FIG. 22, panel A), and a decrease of 60% of the patients' mean HIV viral loads following a 6-months post-treatment (FIG. 22, panel B), and in most cases decreased to undetectable levels after 180 months (FIG. 22, panel B).

In FIG. 22, panel C, a subset of the original patients (n=13) were re-tested at 180 months. The results of this analysis showed that CD4 counts in most of the re-tested patients returned to near baseline levels. In addition, viral loads in most of these re-tested patients had decreased to undetectable (<20 copies/ml) levels at 180 months post-treatment.

Example 19. Analysis of Neutralizing Antibody Production

Antisera from the subset of original patients (n=13) in FIG. 22C were further evaluated for production of neutralizing antibodies in an HIV neutralizing antibody assay as previously described (Simek et al., J. Virol., 83 (14): 7337-7348 July 2009). Multiple assay controls were set up to monitor each plate in a run and to allow for comparison of runs over time. The two types of controls included: (1) a control virus panel tested with all samples (sera, plasma, antibodies, etc.) and (2) an antibody control. The control virus panel includes the neutralization sensitive lab strain env, HIV-1N1.4-3; a less sensitive primary isolate env, JRCSF; and a specificity control env, amphotropic murine leukemia virus (aMLV) envelope. aMLV was used as a specificity control, because it is a non-HIV envelope and has not been found to be inhibitable by antibodies to HIV. Any inhibition of aMLV by plasma would be attributed to non-specific factors. The antibody control included a broadly neutralizing HIV+ plasma present on all control assay plates.

Figure 23:
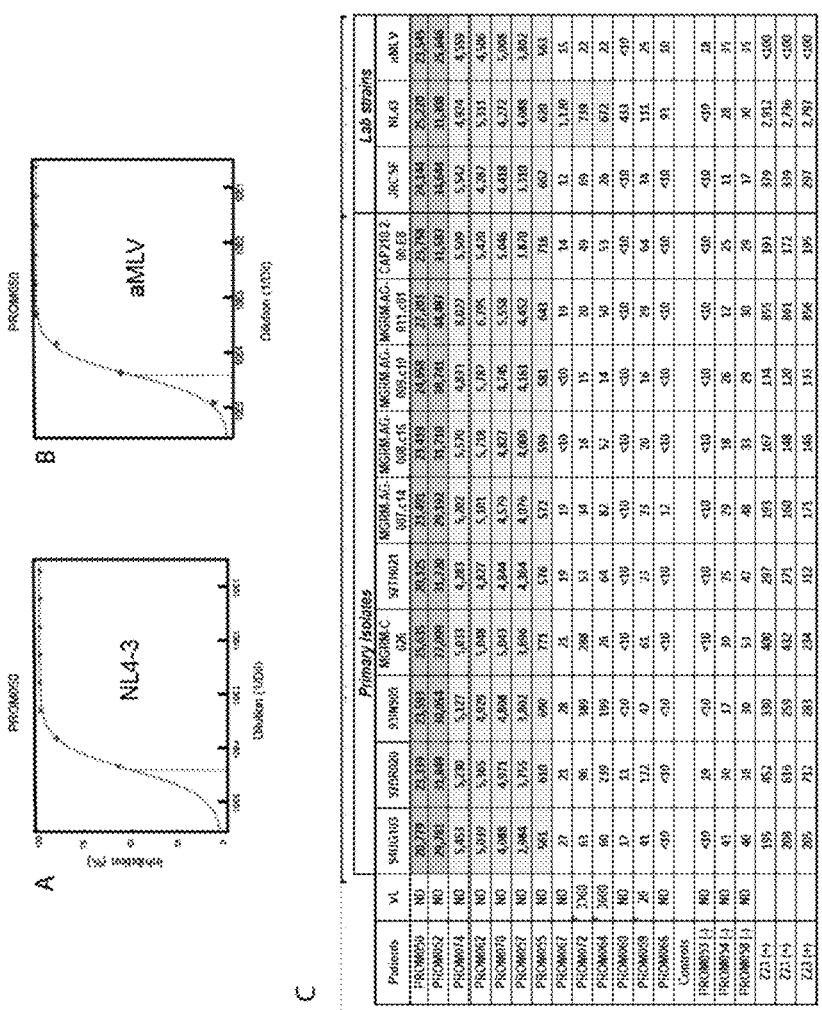
FIG. 23, panels A and B show that the 13 re-tested patients in FIG. 22, panel C produced neutralizing antibodies.

FIG. 23, panels A-C summarize the results of the HIV neutralizing antibody assay using antisera obtained from the 13 re-tested patients at 180 months post-treatment. FIG. 23, panels A and B show the results of the patient PROM050 serum being tested in a MAGI indicator cell assay for neutralizing activity against HIV-1 pseudotyped with an HIV-1NL4-3 env or an aMLV env, respectively. FIG. 23, panel C shows a table depicting antibody titers from the 13 re-tested patients at 180 months post-treatment against each of an HIV-1 pseudotyped with an HIV-1 envelope from one or 10 primary strains or one of 3 lab strains of HIV-1, as indicated. In this case, the serum from each of these 13 patients was tested against 13 different isolates of HIV-1 in 5 different clades. The table in FIG. 23, panel C summarizes reciprocal dilutions of the inhibitory dose to induce 50% reduction in replication of virus (ID 50) as measured in a MAGI indicator cell assay. Darker shaded areas depict higher titers, while the lighter shaded areas depict lower titers.

Seven of these individuals had high titers of antibody against all of the isolates. Six of the patients had lower levels of antibody. All of the patients had significant levels of neutralizing antibodies against the common lab strain, HIV-1NL4-3. Not wishing to be bound by theory, the results suggest that binding of MoMo30 to glycosyl groups of gp120 exerts pressure for selection of mutant viruses having fewer glycosyl groups so the virus will be less susceptible to MoMo30. Thus, viruses with fewer sugars will be more antigenic and allow the host to mount a neutralizing ab response.

The follow up patients were tested for neutralizing ab at 180 months. More than half of them show high levels of ab that can neutralize over a dozen strains of HIV-1. The pseudotyped strains were used to test different primary envelope proteins. MuMLV env was used as a negative control, since there was no expectation for subjects being infected with this mouse virus. However, half of the patients also had an antibody that could neutralize that control, suggesting a broadly cross-reactive antibody. These results suggest that neutralizing antibodies raised in response to MoMo30 are responsible for the long-term control of HIV infection.

Figure 24:
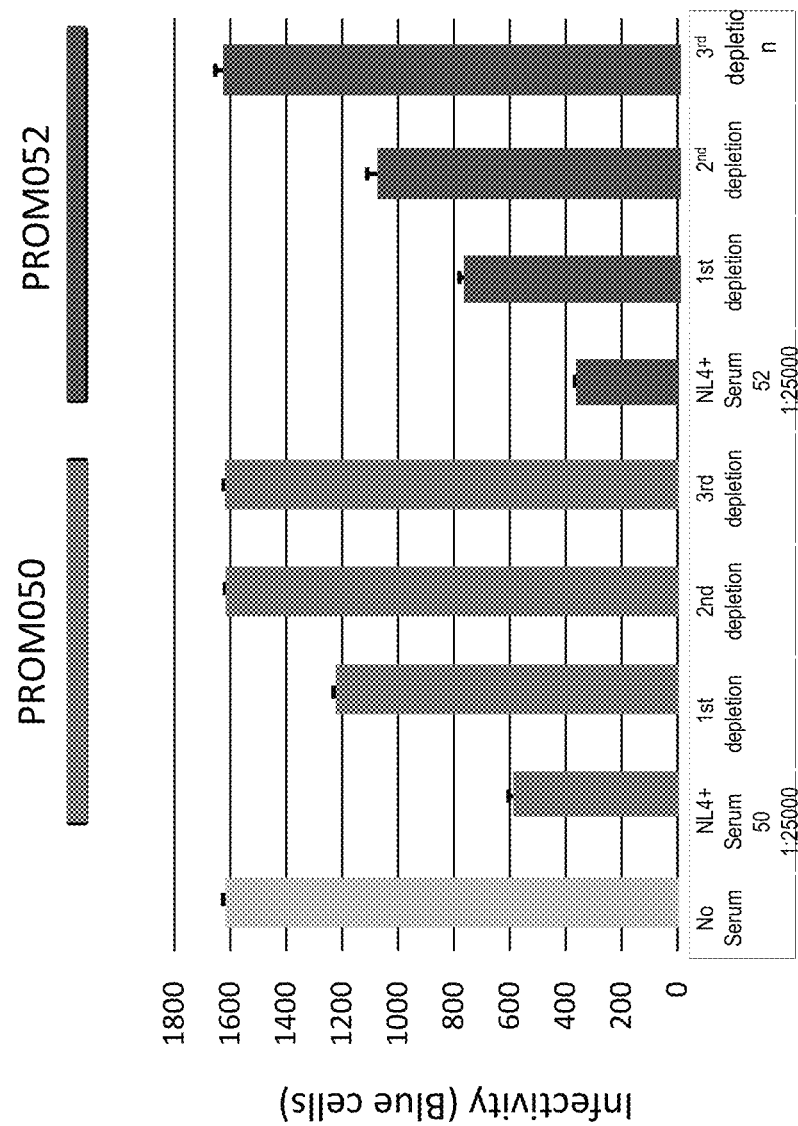
FIG. 24 shows the results of an analysis in which serum from two patients (PROM050 and PROM052) treated with MoMo30 extracts were tested for neutralizing activity against HIVNL4-3 following 3 successive rounds of Protein A/G adsorption. Following adsorption, neutralizing activity was completely depleted.

FIG. 24 shows that the neutralizing activity of serum from two patients (PROM050 and PROM052) treated with MoMo30 is completely eliminated following 3 successive rounds of Protein A/G adsorption. Additionally, these results confirm that the inhibitory activity was solely attributed to antibodies rather than an effect caused by the use of other anti-retroviral agents.

The above description is for the purpose of teaching the person of ordinary skill in the art how to practice the present invention, and it is not intended to detail all those obvious modifications and variations. While various embodiments have been described above, it should be understood that such disclosures have been presented by way of example only and are not limiting. Thus, the breadth and scope of the subject compositions and methods should not be limited by any of the above-described exemplary embodiments and should be defined only in accordance with the following claims and their equivalents, which should be understood to cover obvious modifications and variations which are readily apparent to a person of ordinary skill in the art upon reading the description. Further, the claims are intended to cover the components and steps in any sequence which is effective to meet the objectives there intended, unless the context specifically indicates the contrary.

What is claimed is:

1. A method for preventing a microbial infection in a subject, comprising administering to the subject a nutraceutical composition comprising an antimicrobial hevamine A-related protein comprising an amino acid sequence at least 95% identical to SEQ ID NO: 3 or SEQ ID NO: 4, and at least one nutraceutically acceptable carrier.

2. The method of claim 1, wherein the microbial infection is caused by a virus, wherein the virus is HIV, influenza Type 1 virus, SARS-COV-2, SARS-COV-2 or MERS-COV.

3. The method of claim 1, wherein nutraceutical composition is administered to the subject orally, intravenously or intramuscularly.

* * * * *